(12) United States Patent
Freyne et al.

(10) Patent No.: US 9,688,691 B2
(45) Date of Patent: *Jun. 27, 2017

(54) MACROCYCLIC QUINAZOLE DERIVATIVES AND THEIR USE AS MTKI

(71) Applicant: Janssen Pharmaceutica NV, Beerse (BE)

(72) Inventors: Eddy Jean Edgard Freyne, Rumst (BE); Marc Willems, Oud-Turnhout (BE); Peter Ten Holte, Beerse (BE); Alexandra Papanikos, Berchem (BE); Werner Constant Johan Embrechts, Oud-Turnhout (BE); Pierre Henri Storck, Rouen (FR); Virginie Sophie Poncelet, Le Manoir sur Seine (FR)

(73) Assignee: Janssen Pharmaceutica NV, Beerse (BE)

( * ) Notice: Subject to any disclaimer, the term of this patent is extended or adjusted under 35 U.S.C. 154(b) by 33 days.

This patent is subject to a terminal disclaimer.

(21) Appl. No.: 14/285,008

(22) Filed: May 22, 2014

(65) Prior Publication Data

US 2014/0256714 A1  Sep. 11, 2014

Related U.S. Application Data

(63) Continuation of application No. 11/720,693, filed as application No. PCT/EP2005/056609 on Dec. 8, 2005, now abandoned.

(Continued)

(30) Foreign Application Priority Data

Dec. 8, 2004  (EP) ................................. 04106383

(51) Int. Cl.
  C07D 498/06  (2006.01)
  C07D 498/04  (2006.01)
  C07D 498/08  (2006.01)

(52) U.S. Cl.
  CPC ......... *C07D 498/06* (2013.01); *C07D 498/08* (2013.01)

(58) Field of Classification Search
  None
  See application file for complete search history.

(56) References Cited

U.S. PATENT DOCUMENTS

| | | |
|---|---|---|
| 4,067,726 A | 1/1978 | Sasse et al. |
| 4,160,836 A | 7/1979 | Vandenberk et al. |

(Continued)

FOREIGN PATENT DOCUMENTS

| | | |
|---|---|---|
| GB | 807899 | 1/1959 |
| GB | 1 465 451 | 2/1977 |

(Continued)

OTHER PUBLICATIONS

Abe et al., "Fyn kinases-mediated phosphorylation of NMDA receptor NR2B subunit at Tyr1472 is essential for maintenance of neuropathic pain", *Eur J Neurosci*, 2005; 22:1445-1454.

(Continued)

*Primary Examiner* — Noble Jarrell

(57) ABSTRACT

The present invention concerns the compounds of formula

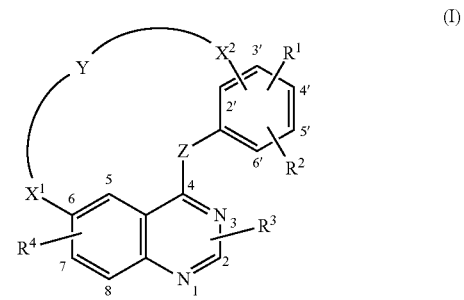

(I)

the N-oxide forms, the pharmaceutically acceptable addition salts and the stereochemically isomeric forms thereof, wherein Z represents NH; Y represents —$C_{3-9}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-2}$alkyl-$NR^{21}$—$H_2$—CO—NH—$C_{1-3}$alkyl- or —$C_{1-2}$ alkyl-$NR^{23}$—CO—$CR^{16}R^{17}$—NH—;

$X^1$ represents O or —O—$C_{1-2}$alkyl-; $X^2$ represents a direct bond, $C_{1-2}$alkyl, —CO—$C_{1-2}$alkyl or $NR^{12}$—$C_{1-2}$alkyl;

$R^1$ represents hydrogen or halo; $R^2$ represents halo, acetylene or $Het^1$ $R^3$ represents hydrogen or cyano; $R^4$ represents $Ar^4$—$C_{1-4}$alkyloxy-, $C_{1-4}$alkyloxy- or $C_{1-4}$alkyloxy substituted with one or where possible two or more substituents selected from $Het^2$, $NR^7R^8$, hydroxy and $C_{1-4}$alkyloxy—$C_{1-4}$alkyloxy-;

$R^7$ represents hydrogen or $C_{1-4}$alkyl; $R^8$ represents $C_{1-4}$alkyl substituted with $NR^{25}R^{26}$ or $C_{1-4}$alkylsulfonyl;

$R^{12}$ represents hydrogen or $C_{1-4}$alkyl-; $R^{13}$ represents $Ar^6$-sulfonyl or $C_{1-6}$alkyloxycarbonyl optionally substituted with phenyl;

$R^{16}$ and $R^{17}$ represents hydrogen, $C_{1-4}$alkyl or $R^{16}$ and $R^{17}$ taken together with the carbon atom to which they are attached from a $C_{3-6}$cycloalkyl;

$R^{23}$ represents $C_{1-4}$alkyl and $R^{23}$ represents hydrogen when $R^{16}$ and $R^{17}$ taken together with the carbon atom to which they are attached from a $C_{3-6}$cycloalkyl;

$R^{25}$, $R^{26}$, $R^{27}$ and $R^{28}$ each independently represent hydrogen or $C_{1-4}$alkylcarbonyl;

$Het^1$ represents 2-bora-1,3-dioxolanyl; $Het^2$ represents piperidinyl, piperazinyl, morpholinyl, thiomorpholinyl or (Continued)

1,1-dioxothiomorpholinyl wherein said $Het^2$ is optionally substituted with $C_{1-4}$alkyloxycarbonyl or $NR^{27}R^{28}$—$C_{1-4}$ alkyl;

$Ar^4$ and $Ar^5$ represents phenyl; $Ar^6$ represents phenyl optionally substituted with nitro.

25 Claims, No Drawings

Related U.S. Application Data

(60) Provisional application No. 60/634,228, filed on Dec. 8, 2004.

(56) References Cited

U.S. PATENT DOCUMENTS

| | | | |
|---|---|---|---|
| 4,442,278 | A | 4/1984 | Giants |
| 5,679,683 | A | 10/1997 | Bridges et al. |
| 5,721,237 | A | 2/1998 | Myers et al. |
| 5,770,599 | A | 6/1998 | Gibson |
| 5,821,240 | A | 10/1998 | Himmelsbach et al. |
| 6,002,008 | A | 12/1999 | Wissner et al. |
| 6,265,410 | B1 | 7/2001 | Bridges et al. |
| 6,288,082 | B1 | 9/2001 | Wissner et al. |
| 6,344,459 | B1 | 2/2002 | Bridges et al. |
| 6,414,148 | B1 | 7/2002 | Thomas et al. |
| 6,521,620 | B1 | 2/2003 | Bridges et al. |
| 6,602,863 | B1 | 8/2003 | Bridges et al. |
| 6,794,395 | B1 | 9/2004 | Roth et al. |
| 7,067,507 | B2 | 6/2006 | Pulley et al. |
| 7,312,225 | B2 | 12/2007 | Luecking et al. |
| 7,648,975 | B2 | 1/2010 | Freyne et al. |
| 7,655,642 | B2 | 2/2010 | Freyne et al. |
| 7,799,772 | B2 | 9/2010 | Freyne et al. |
| RE42,353 | E | 5/2011 | Thomas et al. |
| 8,934,768 | B2 * | 1/2015 | Bottari ............ H04J 14/02 398/25 |
| 2002/0173646 | A1 | 11/2002 | Thomas et al. |
| 2003/0087908 | A1 | 5/2003 | Guens-Meyer et al. |
| 2003/0186987 | A1 | 10/2003 | Bridges et al. |
| 2004/0048880 | A1 | 3/2004 | Himmelsbach et al. |
| 2004/0116388 | A1 | 6/2004 | Armistead et al. |
| 2005/0009867 | A1 | 1/2005 | Hennequin |
| 2005/0250797 | A1 | 11/2005 | Hennequin et al. |
| 2007/0078132 | A1 | 4/2007 | Freyne et al. |
| 2009/0075999 | A1 | 3/2009 | Blanchard et al. |
| 2010/0029627 | A1 | 2/2010 | Papanikos et al. |
| 2010/0069424 | A1 | 3/2010 | Freyne et al. |
| 2010/0105668 | A1 | 4/2010 | Freyne et al. |
| 2010/0152174 | A1 | 6/2010 | Freyne et al. |
| 2010/0160310 | A1 | 6/2010 | Freyne et al. |
| 2010/0190786 | A1 | 7/2010 | Diels et al. |
| 2010/0204197 | A1 | 8/2010 | Diels et al. |
| 2010/0222574 | A1 | 9/2010 | Rombouts et al. |
| 2011/0009404 | A1 | 1/2011 | Buijnsters et al. |

FOREIGN PATENT DOCUMENTS

| | | |
|---|---|---|
| GB | 1 542 514 | 3/1979 |
| WO | WO 95/19774 A1 | 7/1995 |
| WO | WO 95/19970 A1 | 7/1995 |
| WO | WO-96/07657 A1 | 3/1996 |
| WO | WO 96/09294 A1 | 3/1996 |
| WO | WO 96/13529 A1 | 5/1996 |
| WO | WO 96/33980 | 10/1996 |
| WO | WO-96/33980 A1 | 10/1996 |
| WO | WO 96/39145 A1 | 12/1996 |
| WO | WO 97/32880 A1 | 9/1997 |
| WO | WO 97/38983 A1 | 10/1997 |
| WO | WO 98/13354 A1 | 4/1998 |
| WO | WO 98/43960 A1 | 10/1998 |
| WO | WO-99/33792 A2 | 7/1999 |
| WO | WO-99/33793 A2 | 7/1999 |
| WO | WO-99/33795 A1 | 7/1999 |
| WO | WO-99/33815 A1 | 7/1999 |
| WO | WO-00/18761 A1 | 4/2000 |
| WO | WO 00/20402 | 4/2000 |
| WO | WO 00/55159 A2 | 9/2000 |
| WO | WO 01/16130 A1 | 3/2001 |
| WO | WO 02/20479 A1 | 3/2002 |
| WO | WO 02/083654 A1 | 10/2002 |
| WO | WO-02/083654 A1 | 10/2002 |
| WO | WO-03/072062 A2 | 9/2003 |
| WO | WO 03/082290 A1 | 10/2003 |
| WO | WO 2004/009562 A1 | 1/2004 |
| WO | WO-2004/014899 A1 | 2/2004 |
| WO | WO 2004/026829 A2 | 4/2004 |
| WO | WO-2004/026881 A1 | 4/2004 |
| WO | WO 2004/037814 A1 | 5/2004 |
| WO | WO-2004/043936 A1 | 5/2004 |
| WO | WO-2004/074224 A1 | 9/2004 |
| WO | WO 2004/078682 A2 | 9/2004 |
| WO | WO 2004/105765 A1 | 12/2004 |
| WO | WO 2004/004732 A1 | 1/2005 |
| WO | WO 2005/058318 A1 | 6/2005 |
| WO | WO 2005/058913 A1 | 6/2005 |
| WO | WO 2006/061415 A1 | 6/2006 |
| WO | WO 2006/061417 | 6/2006 |
| WO | WO 2007/003525 A2 | 1/2007 |
| WO | WO 2007/058267 A1 | 5/2007 |
| WO | WO-2007/058627 A1 | 5/2007 |
| WO | WO 2007/058628 A1 | 5/2007 |
| WO | WO 2008/006884 A2 | 1/2008 |
| WO | WO-2008/049902 A2 | 5/2008 |
| WO | WO 2008/155421 A2 | 12/2008 |
| WO | WO 2009/016132 A1 | 2/2009 |
| WO | WO 2009/112439 A1 | 9/2009 |

OTHER PUBLICATIONS

Anderson, "The process of structure-based drug design", *Chem Biol.*, 2003; 10:787-797.

Bagrov et al., N-[Hydroxy(amino)alkyl]amides of Amino(nitro)benzoic Acids, *Russian Journal of Organic Chemistry*, 36(5):674-678, 2000.

Barr et al. "Polo-Like Kinases and the Orchestration of Cell Division", *Molecular Cell Biology, Nature Reviews*, 2004; 5:429-440.

Bettencourt-Dias, et al. "SAK/PLK4 is Required for Centriole Duplication and Flagella Development", *Current Biology*, 2005; 15:2199-2207.

Bolen et al., "Nonreceptor tyrosine protein kinases", *Oncogene*, 1993; 8:2025-2031.

Boyce et al., "Requirement of $pp60^{c-src}$ Expression for Osteoclasts to Form Ruffled Borders and Resorb Bone in Mice" *J. Clin. Invest.*, 1992; 90:1622-1627.

Bradshaw, "Cell transformation: the role of oncogenes and factors" *Mutagenesis*, 1986; 1:91-97.

Brown et al., "FlashPlate™ Technology—Principles and Characteristics of Flashplate Scintillation Counting", High Throughput Screening, The Discovery of Bioactive Substances, 1997; 317-328.

Brown et al., "Regulation, substrates and functions of src", *Biochimica et Biophysica Acta*, 1996; 1287:121-149.

Brunton et al., "A role for epidermal growth factor receptor, c-Src and focal adhesion kinase in an in vitro model for the progression of colon cancer", *Oncogene*, 1997; 14:283-293.

Burke, Protein-Tyrosine Kinase Inhibitors, *Drugs of the Future*; 17(2):119-131, 1992.

Burns, et al. "Silencing of the Novel p53 Target Gene Sank/Plk2 Leads to Mitotic Catastrophe in Paclitaxel (Taxol)-Exposed Cells", *Molecular and Cellular Biology*, 2003; 23:5556-5571.

Calderwood et al., "Pyrrolo[2,3-d]pyrimidines Containing Diverse N-7 Substituents as Potent Inhibitors of Lck", *Bioorganic & Medicinal Chemistry Letters*, 2002; 12:1683-1686.

Cardiello et al., "Epidermal Growth Factor Receptor Tyrosine Kinase Inhibitors in Late Stage Clinical Trials", *Oncologic, Endocrine & Metabolic, Expert Opinion*, 2003; 8:501-514.

(56) References Cited

OTHER PUBLICATIONS

Cartwright et al., "Activation of the pp60$^{c\text{-}src}$ protein kinase in an early event in colonic carcinogenesis", *Proc. Natl. Acad. Sci.*, 1990; 87:558-562.
Carvajal et al., "Aurora Kinases: New Targets for Cancer Therapy", *Clinical Cancer Research*, 2006; 12:6869-6875.
Castedo et al., "Cell death by mitotic catastrophe: a molecular definition", *Oncogene*, 2004; 23:2825-2837.
Coghlan et al., "Selective small molecule inhibitors of glycogen synthase kinase-3 modulate glycogen metabolism and gene transcription", *Chemistry & Biology*, 2000; 7:793-803.
Cohen et al., "The renaissance of GSK3", *Nature Reviews: Molecular Cell Biology*, 2001; 2:769-776.
Collins et al., The Chemotherapy of Schistosomiasis. Part IV. Some Ethers of 4-Amino-2-methoxyphenol, *Journal of the Chemical Society*, 1863-1879, 1961.
Cook et al., "Scintillation Proximity Enzyme Assay. A Rapid and Novel Assay Technique Applied to HIV Proteinase", *Structure and Function of the Aspartic Proteinases*, 1991: 525-528.
Courtneidge et al., "Protein tyrosine kinases, with emphasis on the Src family" *Semin. Cancer Biol.*, 1994; 5:239-246.
Cross et al., "Selective small-molecule inhibitors of glycogen synthase kinase-3 activity protect primary neurons from death", *Journal of Neurochemistry*, 2001; 77:94-102.
Dai et al., Tyrosine Kinase Etk/BMX is Up-Regulated in Human Prostate Cancer and Its Overexpression Induces Prostate Intraepithelial Neoplasia in Mouse, Cancer Research, 66:8058-8064, 2006.
Database XP 2300248, Abstract (2001).
Database XP 2300249, Abstract (2000).
Database XP 2300250, Abstract (1994).
Davies, et al, Specificity and Mechanism of Action of Some Commonly Used Protein Kinase Inhibitors, *Biochem J.*, 351:95-105, 2000.
Delia et al., Fused Pyrimidines Part Four: Miscellaneous Fused Pyrimidines, in *The Chemistry of Heterocyclic Compounds, A Series of Monographs* (Interscience), 261-305, 1992.
Druker, et al., Lessons Learned From the Development of an Abl Tyrosine Kinase Inhibitor for Chronic Myelogenous Leukemia, *The Journal of Clinical Investigations*, 105(1):3-7, 2000.
Dumont et al. "Cardiovascular Failure in Mouse Embryos Deficient in VEGF Receptor-3", *Science*, 1998; 282:946-949.
Elder, et al., Overexpression of Transforming Growth Factor α in Psoriatic Epidermis, *Science*, 243:811-814, 1989.
EMBI et al., "Glycogen Synthase Kinase-3 from Rabbit Skeletal Muscle Separation from Cyclic-AMP-Dependent Protein Kinase and Phosporylase Kinase", *Eur. J. Biochem.*, 1980; 107:519-527.
Fanning et al., "Elevated Expression of pp60$^{c\text{-}src}$ in Low Grade Human Bladder Carcinomas" *Cancer Research*, 1992; 52:1457-1462.
Fode et al. "Sak, a Murine Protein-Serine/Threonine Kinase that is Related to the Drosophila Polo Kinase and Involved in Cell Proliferation", *Proc. Natl. Acad. Sci.*, 1994; 9: 6388-6392.
Furuta et al, "Molecular Design of Glutathione-Derived Biochemical Probes Targeting the GS-X Pump", Tetrahedron, 1999; 55:7529-7540.
Furuta et al, Molecular Design of Glutathione-Derived Biochemical Probes Targeting the GS-X Pump, *Tetrahedron*, 55(24):7529-7540, 1999.
Gennaro et al., Table of Contents, Remington's Pharmaceutical Sciences, *18th Ed., Mack Publishing Company*, 1990.
Greene, et al., Protective Groups in Organic Synthesis, *Wiley-Interscience*, 1999.
Hanks et al., "Signaling through focal adhesion kinase", *BioEssays*, 1997; 19:137-145.
He et al., "Suppression of Tumor Lymphangiogenesis and Lymph Node Metastasis by Blocking Vascular Endothelial Growth Factor Receptor 3 Signaling", *Journal of the National Cancer Institute*, 2002; 94:819-824.
Hennequin et al., Novel-4 Anilinoquinazolines with C-7 Basic Side Chains: Design and Structure Activity Relationship of a Series of Potent, Orally Active, VEGF Receptor Tyrosine Kinase Inhibitors, *Journal of Medicinal Chemistry*, 45(6):1300-1312, 2002.
U.S. Appl. No. 10/558,007 Non-Final Office Action dated Apr. 28, 2008, 5 pages.
U.S. Appl. No. 10/558,007 Non-Final Office Action dated Nov. 25, 2008, 5 pages.
U.S. Appl. No. 10/596,509 Non-Final Office Action dated Nov. 26, 2008, 6 pages.
U.S. Appl. No. 11/720,681 Non-Final Office Action dated Mar. 3, 2011, 6 pages.
U.S. Appl. No. 11/720,681 Non-Final Office Action dated Sep. 14, 2010, 7 pages.
U.S. Appl. No. 11/875,288 Final Office Action dated Sep. 24, 2009, 8 pages.
U.S. Appl. No. 11/875,288 Non-Final Office Action dated Apr. 15, 2009, 8 pages.
U.S. Appl. No. 11/993,237 Non-Final Office Action dated Dec. 10, 2010, 7 pages.
U.S. Appl. No. 11/993,237 Final Office Action dated Jul. 21, 2011, 5 pages.
U.S. Appl. No. 12/373,404 Final Office Action dated Jun. 28, 2011, 47 pages.
U.S. Appl. No. 12/373,404 Non-Final Office Action dated Oct. 27, 2010, 12 pages.
U.S. Appl. No. 12/624,637 Non-Final Office Action dated Feb. 2, 2012, 5 pages.
U.S. Appl. No. 12/670,670 Final Office Action dated Mar. 9, 2012, 5 pages.
U.S. Appl. No. 12/670,670 Non-Final Office Action dated Nov. 9, 2011, 10 pages.
International Search Report from PCT/EP2004/005621, dated Oct. 27, 2004.
International Search Report from PCT/EP2004/053497, dated Apr. 12, 2005.
International Search Report from PCT/EP2004/053501, dated Apr. 28, 2005.
International Search Report from PCT/EP2005/056606, dated Apr. 3, 2006.
International Search Report from PCT/EP2005/056609, dated May 26, 2006.
International Search Report from PCT/EP2006/063555, dated Feb. 21, 2008.
International Search Report from PCT/EP2007/061499, dated Jul. 30, 2008.
International Search Report from PCT/EP2008/059833, dated Oct. 23, 2008.
International Search Report from PCT/EP2009/052692, dated Jun. 9, 2009.
Jankowski et al., "Oncogenes and onco-suppressor gene in adenocarcinoma of the oesophagus", *Gut*, 1992; 33:1033-1038.
Kaidanovich et al. "The role of glycogen synthase kinase-3 in insulin resistance and Type 2 diabetes", *Expert Opinion on Therapeutic Targets*, 2002; 6:555-561.
Kaipainen et al. "Expression of the fms-Like Tyrosine Kinase 4 Gene Becomes Restricted to Lymphatic Endothelium During Development", *Pro. Natl. Acad. Sci.*, 1995; 92:3566-70.
Karkkainen et al. "Lymphatic Endothelial Regulation, Lymphoedema, and Lymph Node Metastasis", *Cell & Developmental Biology*, 2002; 13:9-18.
Karn et al. "Human SAK Related to the PLK/polo Family of Cell Cycle Kinases Shows High mRNA Expression in testis", *Oncology Reports*, 1997; 5:505-510. (Abstract only).
Kawato et al., Novel Pepitdomimetics of the Antifungal Cyclic Peptide Rhodopeptin: Synthesis of Mimetics and Their Antifungal Activity, *Organic Letters*, 3(22):3451-3454, 2001.
Klinghoffer et al., "Src family kinases are required for integrin but not PDGFR signal transduction", *EMBO Journal*, 1999; 18:2459-2471.
Kuo, et al., Synthesis and Identification of [1,3,5]Triazine-pyridine Biheteroaryl as a Novel Series of Potent Cyclin-Dependent Kinase Inhibitors, *J. Med. Chem.*, 48 (14):4535-4546, 2005.

(56) References Cited

OTHER PUBLICATIONS

Kypta, "GSK-3 inhibitors and their potential in the treatment of Alzheimer's disease", *Expert Opinion on Therapeutic Patents*, 2005; 15:1315-1331.
Larson et al., "Chapter 13. New Approaches to Antitumor Therapy", *Ann. Reports in Med. Chem.*, 1989; 24:11-128.
Lauffenburger et al., "Cell Migration: A Physically Integrated Molecular Process", *Cell*, 1996; 84:359-369.
Li, et al., "SAK, A New Polo-Like Kinase, is Transcriptionally Repressed by p53 and Induces Apoptosis upon RNAi Silencing", *Neoplasia*, 2005; 7: 312-323.
Liotta et al. "Tumor Invasion and Metastases: Biochemical Mechanisms", *Cancer Treatment and Research*, 1988; 40 223-238.
Lutz et al., "Overexpression and Activation of the Tyrosine Kinase Src in Human Pancreatic Carcinoma", *Biochem. and Biophys. Res. Comm.*, 1998; 243:503-508.
MacKay et al., "A phase II trial of the Src kinase inhibitor AZD0530 in patients with metastatic or locally advanced gastric or gastroesophageal junction (GEJ) adenocarcinoma: A trial of the PMH phase II consortium", 2010 ASCO Annual Meeting, *J Clin Oncol* 28(suppl): abstract e14544.
Makinen et al., "Inhibition of Lymphangiogenesis with Resulting Lymphedema in Transgenic Mice Expressing Soluble VEGF Receptor-3", *Nature Medicine*, 2001; 7:199-205.
Mao et al., "Activation of c-Src by receptor tyrosine kinases in human colon cancer cells with high metastatic potential", *Oncongene*, 1997; 15:3083-3090.
March, J., "Advanced Organic Chemistry, Reactions, Mechanisms, and Structure", Third Edition, pp. 1036-1039 (1985).
Mazurenko et al., "Expression of $pp^{60c-src}$ in human small cell and non-small cell lung carcinomas", *European Journal of Cancer*, 1992; 28:372-377.
McOmie, J.F.W., Protective Groups in Organic Chemistry, Editor J.F.W., Plenum Press (1973)(Table of Contents).
Morin, From Oncogene to Drug: Development of Small Molecule Tyrosine Kinase Inhibitors as Anti-Tumor and Anti-Angiogenic Agents, *Oncogene*, 19:6574-6583, 2000.
Murphy et al., Intramolecular Termination of Radical-Polar Crossover Reactions, *Journal of the Chemical Society Perkin Transactions 1*, 15:2331-2339, 1998.
Muthuswamy et al., "Activation of Src family kinases in Neu-induced mammary tumors correlates with their asociation with distinct sets of tyrosine phosphorylated proteins in vivo", *Oncogene*, 1995; 11:1801-1810.
Nagamatsu, et al., General Syntheses of 1-Alkyltoxoflavin and 8-Alkylfervenulin Derivatives of Biological Significance by the Regioselective Alkylation of Reumycin Derivatives and the Rates of Transalkylation From 1-Alkyltoxoflavins Into Nucleophiles, *J. Chem. Soc., Perkin Trans. 1*, 130-137, 2001.
Nagamatsu, et al., Syntheses of 3-Substituted 1-Methyl-6-Phenylprimido[5,4-e]-1,2,4-Triazine-5,7(1H,6H)-Diones (6-Phenyl Analogs of Toxoflavin) and Their 4-Oxides, and Evaluation of Antimicrobial Activity of Toxoflavins and Their Analogs, *Chem. Pharm. Bull*, 41(2):362-368, 1993.
Nicolson et al., "Cancer Metastasis: Tumor Cell and Host Organ Properties Important in Metastasis to Specific Secondary Sites", *Biochimica et Biophysica Acta*, 1988; 948: 175-224.
Norman, "Emerging Fundamental Themes in Modern Medicinal Chemistry", *Drug News Perspect*, 2001; vol. 14: 242-247.
Ny et al., "A Genetic *Xenopus laevis* Tadpole Model to Study Lymphangiogenesis", *Nature Medicine*, 2005; 11:998-1004.
Owens et al., "The catalytic activity of the Src family kinases is required to disrupt cadherin-dependent cell-cell contacts", *Molecular Biology of the Cell*, 2000; 11:51-64.
Palmer et al., Tyrosine Kinase Initors. II. Soluble Analogues of Pyrrolo- and Pyrazoloquinazolines as Epidermal Growth Factor Receptor Inhibitors: Synthesis, Biological Evaluation, and Modeling of the Mode of Binding, *Journal of Medicinal Chemistry*, 40(10):1519-1529, 1997.
Parsons et al., "Src family protein tyrosine kinases: cooperating with growth factor and adhesion signaling pathways", *Current Opinion in Cell Biology*, 1997; 9:187-192.
Pleixats et al., "The Search for New Biochemical Photoprobes. The Nucleophilic Photosubstitution of 2-Fluoro-4-Nitronisole", *Tetrahedron*, 1989; 45: 7817-7826.
Prichard et al., "The prevention of breast cancer," *British Journal of Surgery*, 2003; 90:772-783.
Rusnak et al., "The characterization of novel, dual ErbB-2/EGFR, tyrosine kinase inhibitors: potential therapy for cancer", *Cancer Research*, 2001; 61: 7196-7203.
Saito et al., Fyn: A Novel Molecular Target in Prostate Cancer, *Cancer*, 116(7):1629-1637; 2010.
Schlaepfer et al., "Signaling through focal adhesion kinase" *Progress in Biophysics and Molecular Biology*, 1999; 71:435-478.
Shawver, et al., Smart Drugs: Tyrosine Kinase Inhibitors in Cancer Therapy, *Cancer Cell*, 1:117-123, 2002.
Skobe et al. "Induction of Tumor Lymphangiogenesis by VEGF-C Promotes Breast Cancer Metastasis", *Nature Medicine*, 2001; 7: 192-198.
Spankuch-Schmitt et al., "Downregulaton of Human Polo-Like Kinase Activity by Antisense Oligonucleotides Induces Growth Inhibitor in Cancer Cells", *Oncogene*, 2002; 21: 3162-3171.
Stacker et al., "The Role of Tumor Lymphangiogenesis in Metastatic Spread", *FASEB J.*, 2002; 9:922-934.
Table of Contents, *Chemical Reviews*, 96(8), 1996.
Thiel, "Structure-aided drug design's next generation", 2004; *Nature Biotechnol* 22: 513-519.
Ullrich et al., "Signal transduction by receptors with tyrosine kinase acti.,vity" *Cell*, 1990; 61:203-212.
Underiner et al., "Development of Vascular Endothelial Growth Factor Receptor (VEGFT) Kinase Inhibitors as Anti-Angiogenic Agents in Cancer Therapy", *Current Medicinal Chemistry*, 2004; 11: 731-745.
Verbeek et al., "Overexpression of c-Src enhances cell-matrix adhesion and cell migration in PDGF-stimulated NIH3T3 fibroblasts" *Exp. Cell Res.*, 1999; 248(2):531-537.
Von Pawel, "Gefitinib (Iressa, ZD1839): a novel targeted approach for the treatment of solid tumors," *Bull. Cancer*, 2004; 91(5):E70-E76.
Wang et al., "Cell Cycle Arrest and Apoptosis Induced by Human Polo-Like Kinase 3 is Mediated through Perturbation of Microtubule Integrity", *Molecular and Cellular Biology*, 2002: 22:3450-3459.
Wedge et al. "ZD6474 Inhibits Vascular Endothelial Growth Factor Signaling, Angiogenesis, and Tumor Growth Following Oral Administration", *Cancer Research*, 2002; vol. 62: 4645-55.
Wiener et al., "Decreased Src tyrosine kinase activity inhibits malignant human ovarian cancer tumor growth in a nude mouse model" *Clin. Cancer Res.*, 1999; 5:2164-2170.
Wilks, "Protein tyrosine kinase growth factor receptors and their ligands in development, differentiation, and cancer" *Adv. Cancer Res.*, 1993; 60:43-73.
Wissner et al., "4-Anilino-6,7-dialkoxyquinoline-3-carbonitrile Inhibitors of Epidermal Growth Factor Receptor Kinase and Their Bioisosteric Relationship to the 4-Anilino-6,7-dialkoxyquinazoline Inhibitors", *Journal of Medicinal Chemistry*, 2000, 43: 3244-3256.
Wright et al., "Anilinoquinazoline Inhibitors of Fructose 1,6-Bisphosphate Bind at a Nove Allosteric Site: Synthesis, in vitro Characterizations, and X-ray Crystallography", *J. Med. Chem.*, 2002; 45: 3865-3877.
Yang et al., "Inhibition of Epidermal Growth Factore Receptor Tyrosine Kinase by Chalcone Derivatives," *Biochimica et Biophysica Acta*, 2001; 1550: 144-152.
Yarden et al., "Growth factor receptor tyrosine kinases" *Ann. Rev. Biochem.*, 1988; 57:443478.
Yoneda et al., "Herbimycin A, a pp60c-src tyrosine kinase inhibitor, inhibits osteoclastic bone resorption in vitro and hypercalcemia in vivo" *J. Clin. Invest.*, 1993; 91:2791-2795.
Yuan et al. "Efficient Internalization of the Polo-Box of Polo-Like Kinase 1 Fused to an Antennapedia Peptide Results in Inhibition of Cancer Cell Proliferation", *Cancer Research*, 2002; 62:4186-4190.

(56) References Cited

OTHER PUBLICATIONS

Zeneca Ltd., "4-Anilinoquinazoline Derivatives", *Expert Opinion on Therapeutic Patents*, 1998; 8: 475-478.
Zeneca Ltd., 4-Anilinoquinazoline Derivatives, Expert Opinion of Therapeutic Patents, 8(4):475-478, 1998.
Zetter et al., "The Cellular Basis of Site-Specific Tumor Metastasis", *N. Engl. J. Med.*, 1990; 322: 605-12.
Patani, G.A., et al., "Bioisosterism: A Rational Approach in Drug Design", Chem. Rev., vol. 96, No. 8, pp. 3147-3176 (1996).
Kumazawa, T., et al., "(E)-4-{2-[[3-(Indol-5-yl)-1-oxo-2-butenyl]amino]phenoxy}butyric Acid Derivatives: A New Class of Steroid 5α-Reductase Inhibitors in the Rat Prostate", J. Med. Chem., vol. 38, No. 15, pp. 2887-2892 (1995).
Seth, P.P., et al., "Efficient solution phase synthesis of 2-(N-acyl)-aminobenzimidazoles", Tetrahedron Letters, vol. 43, pp. 7303-7306 (2002).
Japanese Office Action dated Jan. 25, 2011 citing WO00/20402.
Beilstein Registry No. 7203413—Morita, S., et al., "An Efficient Synthesis of a Key Intermediate towards (S)-(-)-Nadifloxacin", Tetrahedron: Asymmetry, vol. 6, No. 1, pp. 245-254 (1995).
Beilstein Registry No. 3298195 (1928;1974).
Beilstein Registry No. 3269895 (1928;1974).
Beilstein Registry No. 2972092 (1972-1999).
Beilstein Registry No. 2719201—Jolidon, S., et al., "101. Untersuchungen über aromatische Amino-Claisen-umalagerungen", Helvetica Chimica Acta, vol. 60, Fasc. 3, pp. 977-1032 (1977).
Beilstein Registry No. 2840450—Nagasaka, T. et al., "Synthesis of 4-Substituted Indole Derivatives", Heterocycles, vol. 8, pp. 371-376 (1977).
Beilstein Registry No. 9261432—Hajipour, A.R., et al., "Tetramethylammonium Dichloroiodate: An Efficient and Environmentally Friendly Iodination Reagent for Iodination of Aromatic Compounds under Mild and Solvent-Free Conditions", J. Org. Chem., vol. 67, No. 24, pp. 8622-8624 (2002).
Beilstein Registry No. 8835246—Mertens, J., et al., "Synthesis and $Cu_{1+}$ Assisted Radiosynthesis of 2-Radioiodophloretinic Acid, A Potential Glut Tracer", J. Laelled Cpd. Radiopharm, vol. 44, pp. S951-S953 (2001).
Beilstein Registry No. 3281452 (1882).
Beilstein Registry No. 7023897—Shoshani, I., et al., "Synthesis of Iodo-Aryl-azido Adenosine Analogs As Affinity Ligands For Adenylyl Cyclase", Nucleosides & Nucleotides, vol. 13, No. 9, pp. 1977-1989 (1994).
Expert Opinion on Therapeutic Patents, Ashley Publications, vol. 8, No. 4, pp. 475-478 (1998).
Beilstein Registry No. 2655569—Faulkner, J.K., et al., "Fungal Detoxication. Part VIII. Metabolism of Substituted 4-Phenoxy-butyric Acids by Aspergillus niger", Journal of Chemical Society (C), pp. 884-886 (1996).
Beilstein Registry No. 8492853—Wang, S., et al., "Development of a Compound-Specific ELISA for Flufenoxuron and an Improved Class-Specific Assay for Benzoylphenylurea Insect Growth Regulators", J. Agric. Food Chem., vol. 47, No. 8, pp. 3416-3424 (1999).
Beilstein Registry No. 9332009—Cartoni, A., et al., "NMR-Spectroscopic, computational and mass-spectrometric investigations on the cis/trans analogues of 2,3,4-trihydronaphthalene-1-one", Tetrahedron, vol. 59, No. 8, pp. 1309-1316 (2003).

\* cited by examiner

SEQUENCE LISTING

<160> NUMBER OF SEQ ID NOS: 3

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Ala Ile Tyr Ala Ala Pro Phe Ala Lys Lys Lys
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Val Glu Lys Ile Gly Glu Gly Thr Tyr Gly Val Val Tyr Lys
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Lys Lys Ser Pro Gly Glu Tyr Val Asn Ile Glu Phe Gly
1               5                   10

MACROCYCLIC QUINAZOLE DERIVATIVES AND THEIR USE AS MTKI

CROSS REFERENCE TO RELATED APPLICATIONS

This application is a continuation of U.S. patent application Ser. No. 11/720,693, filed Jun. 1, 2007, pending; which is the national stage of PCT Application No. PCT/EP2005/056609, filed 8 Dec. 2004, which claims priority from European Patent Application No. 04106383.5, filed 8 Dec. 2004, and U.S. Application No. 60/634228, filed 8 Dec. 2004, the entire disclosures of which are hereby incorporated in their entirely.

The human genome encompasses some 2,000 proteins that utilize adenosine 5'-triphosphate (ATP) in one way or another and some 500 of these encode for protein kinases, i.e the protein-tyrosine and protein-serine/threonine kinases, that share a catalytic domain conserved in sequence and structure but which are notably different in how their catalysis is regulated. Substrate phosphorylation by these enzymes is nature's predominant molecular way of organizing cellular signal transduction and regulating biochemical processes in general. It is not surprising, therefore, that abnormal phosphorylation of cellular proteins is a hallmark of disease and that there is a growing interest in the use of kinase inhibitors as drugs for therapeutic intervention in many disease states such as cancer, diabetes, inflammation and arthritis.

It is an object of the present invention to provide such kinase inhibitors, that are quinazoline derived macrocycles, hereinafter also referred to as multi targeting kinase inhibitors (MTKI), found to possess anti-proliferative activity, such as anti-cancer activity and which are accordingly useful in methods of treatment of the human or animal body, for example in the manufacture of medicaments for use in hyper proliferative disorders such as atherosclerosis, restenosis and cancer. The invention also relates to processes for the manufacture of said quinazoline derivatives, to pharmaceutical compositions containing them and to their use in the manufacture of medicaments of use in the production of anti-proliferative effect.

In particular, the compounds of the present invention were found to inhibit tyrosine kinase enzymes, also called tyrosine kinases. Tyrosine kinases are a class of enzymes, which catalyse the transfer of the terminal phosphate of adenosine triphosphate to the phenolic hydroxy-group of a tyrosine residue present in the target protein. It is known, that several oncogenes, involved in the transformation of a cell into a malignant tumour cell, encode tyrosine kinase enzymes including certain growth factor receptors such as EGF, FGF, IGF-1R, IR, PDGF and VEGF. This family of receptor tyrosine kinases and in particular the EGF family of receptor tyrosine kinases are frequently present in common human cancers such as breast cancer, non-small cell lung cancers including adenocarcinomas and squamous cell cancer of the lung, bladder cancer, oesophageal cancer, gastrointestinal cancer such as colon, rectal or stomach cancer, cancer of the prostate, leukaemia and ovarian, bronchial or pancreatic cancer, which are examples of cell proliferation disorders.

Accordingly, it has been recognised that the selective inhibition of tyrosine kinases will be of value in the treatment of cell proliferation related disorders. Support for this view is provided by the development of Herceptin® (Trastuzumab) and Gleevec™ (imatinib mesylate) the first examples of target based cancer drugs. Herceptin® (Trastuzumab) is targeted against Her2/neu, a receptor tyrosine kinase found to be amplified up to 100-fold in about 30% of patients with invasive breast cancer. In clinical trials Herceptin® (Trastuzumab) proved to have anti-tumour activity against breast cancer (Review by L. K. Shawer et al, "Smart Drugs: Tyrosine kinase inhibitors in cancer therapy", 2002, Cancer Cell Vol. 1, 117), and accordingly provided the proof of principle for therapy targeted to receptor tyrosine kinases. The second example, Gleevec™ (imatinib mesylate), is targeted against the abelson tyrosine kinase (BcR-Abl), a constitutively active cytoplasmic tyrosine kinase present in virtually all patients with chronic myelogenous leukaemia (CML) and 15% to 30% of adult patients with acute lymphoblastic leukaemia. In clinical trials Gleevec™ (imatinib mesylate) showed a spectacular efficacy with minimal side effects that led to an approval within 3 months of submission. The speed of passage of this agent through clinical trials and regulatory review has become a case study in rapid drug development (Drucker B. J. & Lydon N., "Lessons learned from the development of an Abl tyrosine kinase inhibitor for chronic myelogenous leukaemia.", 2000, J. Clin. Invest. 105, 3).

Further support is given by the demonstration that EGF receptor tyrosine kinase inhibitors, specifically attenuates the growth in athymic nude mice of transplanted carcinomas such as human mammary carcinoma or human squamous cell carcinoma (Review by T. R. Burke Jr., Drugs of the Future, 1992, 17, 119). As a consequence, to treat different cancers there has been considerable interest in the development of drugs that target the EGFR receptor. For example, several antibodies that bind to the extra-cellular domain of EGFR are undergoing clinical trials, including Erbitux™ (also called C225, Cetuximab), which was developed by Imclone Systems and is in Phase III clinical trials for the treatment of several cancers. Also, several promising orally active drugs that are potent and relatively specific inhibitors of the EGFR tyrosine kinase are now well advanced in clinical trials. The AstraZeneca compound ZD1839, which is now called IRESSA® and approved for the treatment of advanced non-small-cell lung cancer, and the OSI/Genentech/Roche compound OSI-774, which is now called Tarceva™ (erlotinib), have shown marked efficacy against several cancers in human clinical trials (Morin M. J., "From oncogene to drug: development of small molecule tyrosine kinase inhibitors as anti-tumour and anti-angiogenic agents, 2000, Oncogene 19, 6574).

In addition to the above, EGF receptor tyrosine kinases are shown to be implicated in non-malignant proliferative disorders such as psoriasis (Elder et al., Science, 1989, 243; 811). It is therefore expected that inhibitors of EGF type receptor tyrosine kinases will be useful in the treatment of non-malignant diseases of excessive cellular proliferation such as psoriasis, benign prostatic hypertrophy, atherosclerosis and restenosis.

It is disclosed in International Patent Application WO96/33980 and in J. Med. Chem, 2002, 45, 3865 that certain 4 anilino substituted quinazoline derivatives may be useful as inhibitors of tyrosine kinase and in particular of the EGF type receptor tyrosine kinases. Unexpectedly it was found that Quinazoline derivatives of the present formula (I) that are different in structure show to have tyrosine kinase inhibitory activity.

It is accordingly an object of the present invention to provide further tyrosine kinase inhibitors useful in the manufacture of medicaments in the treatment of cell proliferative related disorders.

This invention concerns compounds of formula (I)

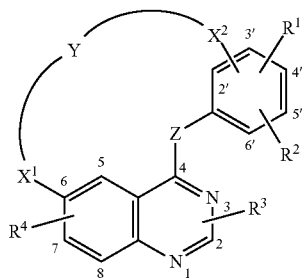

the N-oxide forms, the pharmaceutically acceptable addition salts and the stereochemically isomeric forms thereof, wherein Z represents NH;

Y represents —$C_{3-9}$alkyl-, —$C_{2-9}$alkenyl-, —$C_{1-5}$alkyl-oxy-$C_{1-5}$alkyl-, —$C_{1-5}$alkyl-NR$^{13}$—$C_{1-5}$alkyl-, —$C_{1-5}$alkyl-NR$^{14}$—CO—$C_{1-5}$alkyl-, —$C_{1-6}$alkyl-NH—CO—, —NH—CO—$C_{1-6}$alkyl-, —CO—$C_{1-7}$alkyl-, —$C_{1-7}$alkyl-CO—, $C_{1-6}$alkyl-CO—$C_{1-6}$alkyl, —$C_{1-2}$alkyl-NR$^{23}$—CO—CR$^{16}$R$^{17}$—NH—, —$C_{1-2}$alkyl-CO—NH—CR$^{18}$R$^{19}$—CO—, —$C_{1-2}$alkyl-CO—NR$^{20}$—$C_{1-3}$alkyl-CO—, —$C_{1-2}$alkyl-NR$^{21}$—CH$_2$—CO—NH—$C_{1-3}$alkyl-, NR$^{22}$—CO—$C_{1-3}$alkyl-NH—, —$C_{1-3}$alkyl-NH—CO-Het$^{20}$-, $C_{1-2}$alkyl-CO-Het$^{21}$-CO—, or -Het$^{22}$-CH$_2$—CO—NH—$C_{1-3}$alkyl-;

X$^1$ represents O, —O—$C_{1-2}$alkyl-, —O—N═CH—, NR$^{11}$ or —NR$^{11}$—$C_{1-2}$alkyl-; in a particular embodiment X$^1$ represents O, —O—$C_{1-2}$alkyl- or NR$^{11}$—$C_{1-2}$alkyl;

X$^2$ represents a direct bond, $C_{1-2}$alkyl, O, —O—$C_{1-2}$alkyl-, CO, —CO—$C_{1-2}$alkyl-, —O—N═CH—, NR$^{12}$ or NR$^{12}$—$C_{1-2}$alkyl-; in a particular embodiment X$^2$ represents a direct bond, —O—, —O—$C_{1-2}$alkyl, —CO—$C_{1-2}$alkyl- or NR$^{12}$—$C_{1-2}$alkyl-;

R$^1$ represents hydrogen, cyano, halo or hydroxy, preferably halo;

R$^2$ represents hydrogen, cyano, halo, hydroxy, hydroxycarbonyl-, $C_{1-4}$alkyloxycarbonyl-, Het$^{16}$-carbonyl-, $C_{1-4}$alkyl-, $C_{2-6}$alkynyl-, Ar$^5$, Het$^1$ or dihydroxyborane;

R$^3$ represents hydrogen, cyano, halo, hydroxy, formyl, $C_{1-6}$alkoxy-, $C_{1-6}$alkyl-, $C_{1-6}$alkoxy-substituted with halo, or R$^3$ represents $C_{1-4}$alkyl substituted with one or where possible two or more substituents selected from hydroxy or halo;

R$^4$ represents Ar$^4$—$C_{1-4}$alkyloxy-, $C_{1-4}$alkyloxy- or R$^4$ represents $C_{1-4}$alkyloxy substituted with one or where possible two or more substituents selected from hydroxy-, halo, $C_{1-4}$alkyloxy-, $C_{1-4}$alkyloxy-$C_{1-4}$alkyloxy-, NR$^{37}$R$^{38}$-carbonyloxy-, Het$^5$-carbonyloxy-, NR$^7$R$^8$, NR$^9$R$^{10}$-carbonyl-, Het$^3$-carbonyl-, Het$^{13}$-oxy- or Het$^2$-;

R$^7$ represents hydrogen, hydroxy-$C_{1-4}$alkyl- or $C_{1-4}$alkyl;

R$^8$ represents $C_{3-6}$cycloalkyl; Het$^6$-carbonyl-; Het$^7$-aminocarbonyl-; Het$^8$; Het$^9$-oxycarbonyl-; Het$^{10}$-sulfonyl-; $C_{1-4}$alkyloxycarbonyl; mono- or di($C_{1-4}$alkyl)aminocarbonyl-; mono- or di($C_{1-4}$alkyl)aminocarbonyl substituted with $C_{1-4}$alkylsulfonyl-; or
$C_{1-4}$alkylcarbonyl optionally substituted with one or more substituents selected from $C_{1-4}$alkylsulfonyl, hydroxy- and $C_{1-4}$alkyloxy-; or
R$^8$ represents $C_{1-4}$alkyl substituted with one or more substituents selected from $C_{1-4}$alkylsulfonyl-, NR$^{25}$R$^{26}$, aminocarbonyloxy-, $C_{1-4}$alkylcarbonyloxy-, aminocarbonyl-, hydroxy-$C_{1-4}$alkyloxy-, $C_{1-4}$alkyloxy-$C_{1-4}$alkyloxy-, and Het$^{11}$;

R$^9$ represents hydrogen or $C_{1-4}$alkyl-;

R$^{10}$ represents Het$^4$ or $C_{1-4}$alkyl-substituted with $C_{1-4}$alkylsulfonyl-;

R$^{11}$ represents hydrogen, $C_{1-4}$alkyl- or $C_{1-4}$alkyl-oxy-carbonyl-;

R$^{12}$ represents hydrogen, $C_{1-4}$alkyl-, $C_{1-6}$alkyloxycarbonyl- or $C_{1-6}$alkyloxycarbonyl-substituted with phenyl;

R$^{13}$ represents hydrogen, Het$^{14}$-$C_{1-4}$alkyl, $C_{1-6}$alkyloxycarbonyl optionally substituted with phenyl or R$^{13}$ represents Ar$^6$-sulfonyl or Het$^{24}$-$C_{1-4}$alkylcarbonyl; in particular morpholinyl-$C_{1-4}$alkyl;

R$^{14}$ and R$^{15}$ are each independently selected from hydrogen, $C_{1-4}$alkyl, Het$^{15}$-$C_{1-4}$alkyl- or $C_{1-4}$alkyloxyC$_{1-4}$alkyl-;

R$^{16}$ and R$^{17}$ each independently represents hydrogen, $C_{1-4}$alkyl or $C_{1-4}$alkyl substituted with hydroxy-, $C_{3-6}$cycloalkyl or phenyl; or R$^{16}$ and R$^{17}$ taken together with the carbon atom to which they are attached form a $C_{3-6}$cycloalkyl;

R$^{18}$ represents hydrogen or $C_{1-4}$alkyl optionally substituted with hydroxy or phenyl;

R$^{19}$ represents hydrogen or $C_{1-4}$alkyl, in particular hydrogen or methyl, even more particular hydrogen;

R$^{20}$ represents hydrogen or $C_{1-4}$alkyl, in particular hydrogen or methyl;

R$^{21}$ represents hydrogen, $C_{1-4}$alkyl, Het$^{23}$-$C_{1-4}$alkylcarbonyl- or
R$^{21}$ represents mono- or di($C_{1-4}$alkyl)amino-$C_{1-4}$alkylcarbonyl- optionally substituted with hydroxy, pyrimidinyl, dimethylamine or $C_{1-4}$alkyloxy;

R$^{22}$ represents hydrogen or $C_{1-4}$alkyl optionally substituted with hydroxy or $C_{1-4}$alkyloxy;

R$^{23}$ represents $C_{1-4}$alkyl optionally substituted with hydroxy-, $C_{1-4}$alkyloxy- or Het$^{25}$; R$^{23}$ may also represent hydrogen when R$^{16}$ and R$^{17}$ taken together with the carbon atom to which they are attached form a $C_{3-6}$cycloalkyl;

R$^{25}$ and R$^{26}$ each independently represent hydrogen, $C_{1-4}$alkyl, $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-, in particular R$^{25}$ and R$^{26}$ each independently represent hydrogen, $C_{1-4}$alkyl, $C_{1-4}$alkylsulfonyl-, aminocarbonyl-, mono- or di($C_{1-4}$alkyl)aminocarbonyl- or $C_{1-4}$alkylcarbonyl-;

R$^{27}$ and R$^{28}$ each independently represent hydrogen, $C_{1-4}$alkyl, $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-; or for those compounds of formula (I) wherein Het$^2$ represents a heterocycle selected from morpholinyl, piperazinyl, piperidinyl pyrrolidinyl or thiomorpholinyl substituted with NR$^{27}$R$^{28}$—$C_{1-4}$alkyl said R$^{27}$ and R$^{28}$ each independently represent $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

R$^{29}$ and R$^{30}$ each independently represent hydrogen, aminosulfonyl, aminocarbonyl, mono- or di($C_{1-4}$alkyl)aminocarbonyl-, mono- or di($C_{1-4}$alkyl)aminosulfonyl-, or $C_{1-4}$alkyl- optionally substituted with one or more substituents selected from $NR^{31}R^{32}$, $C_{1-4}$alkylsulfonyl, aminocarbonyloxy-, hydroxy-, $C_{1-4}$alkyloxy-, aminocarbonyl- and mono- or di($C_{1-4}$alkyl)aminocarbonyl-, or $C_{1-4}$alkyloxycarbonyl optionally substituted with one or more substituents selected from hydroxy, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-;

$R^{31}$ and $R^{32}$ each independently represent hydrogen, $C_{1-4}$alkyl, $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

$R^{33}$ represents hydrogen or $C_{1-4}$alkyl;

$R^{34}$ represents $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

$R^{35}$ represents hydrogen or $C_{1-4}$alkyl;

$R^{36}$ represents $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

$R^{37}$ and $R^{38}$ each independently represent hydrogen, $C_{1-4}$alkyl, $C_{1-4}$alkylsulfonyl-, $Het^{12}$ or $C_{1-4}$alkyl substituted with one or more substituents selected from $C_{1-4}$alkylsulfonyl-, hydroxy- and $C_{1-4}$alkyloxy-;

$R^{39}$ and $R^{40}$ each independently represent aminosulfonyl, aminocarbonyl, mono- or di($C_{1-4}$alkyl)aminocarbonyl-, mono- or di($C_{1-4}$alkyl)aminosulfonyl-, or $C_{1-4}$alkyl-substituted with one or more substituents selected from $NR^{31}R^{32}$, $C_{1-4}$alkylsulfonyl, aminocarbonyloxy-, hydroxy-, $C_{1-4}$alkyloxy-, aminocarbonyl- and mono- or di($C_{1-4}$alkyl)aminocarbonyl-, or $C_{1-4}$alkyloxycarbonyl optionally substituted with one or more substituents selected from hydroxy-, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-;

$Het^1$ represents thiazolyl or 2-bora-1,3-dioxolanyl wherein said $Het^1$ is optionally substituted with one or where possible two, three, four or more substituents selected from amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-, mono- or di($C_{1-4}$ alkyl)amino- or amino-carbonyl-;

$Het^2$ represents a heterocycle selected from tetrahydropyranyl, tetrahydrofuranyl, furanyl, 1,1-dioxothiomorpholinyl, piperazininonyl, tetrahydro-1,1-dioxido-2H-thiopyranyl, piperidinonyl, azetidinyl or 2-azetidinonyl wherein said $Het^2$ is optionally substituted with one or where possible two or more substituents selected from hydroxy, amino, $NR^{29}R^{30}$, aminocarbonyl, mono- or di($C_{1-4}$alkyl) aminocarbonyl, $C_{1-4}$alkylsulfonyl or $C_{1-4}$alkyl- optionally substituted with one or more substituents selected from $NR^{27}R^{28}$, $C_{1-4}$alkylsulfonyl, aminocarbonyloxy-, aminocarbonyl- and mono- or di($C_{1-4}$alkyl)aminocarbonyl-, or $C_{1-4}$alkyloxy- optionally substituted with $C_{1-4}$alkyloxy-, or $C_{1-4}$alkyloxycarbonyl optionally substituted with one or more substituents selected from hydroxy, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-; or $Het^2$ represents a heterocycle selected from morpholinyl, piperazinyl, piperidinyl, pyrrolidinyl, thiomorpholinyl or 1,1-dioxothiomorpholinyl wherein said $Het^2$ is optionally substituted with one or where possible two or more substituents selected from $C_{1-4}$alkyl- optionally substituted with one or more substituents selected from $NR^{27}R^{28}$, $C_{1-4}$alkylsulfonyl, aminocarbonyloxy-, aminocarbonyl- and mono- or di($C_{1-4}$alkyl)aminocarbonyl-, or $C_{1-4}$alkyloxy- optionally substituted with $C_{1-4}$alkyloxy-, or $C_{1-4}$alkyloxycarbonyl optionally substituted with one or more substituents selected from hydroxy, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-;

$Het^3$ represents a heterocycle selected from tetrahydropyranyl, tetrahydrofuranyl, furanyl, 1,1-dioxothiomorpholinyl, piperazininonyl, tetrahydro-1,1-dioxido-2H-thiopyranyl, piperidinyl, azetidinyl or 2-azetidinonyl wherein said $Het^3$ is optionally substituted with one or where possible two or more substituents hydroxy-, amino, $C_{1-4}$alkyl-, $C_{3-6}$cycloalkyl-$C_{1-4}$alkyl-, aminosulfonyl-, mono- or di($C_{1-4}$alkyl)aminosulfonyl-, amino-$C_{1-4}$alkyl-, Mono- or di($C_{1-4}$alkyl)amino-$C_{1-4}$alkyl, $NR^{35}R^{36}$, $C_{1-4}$alkyl-sulfonyl-$C_{1-4}$alkyl- or $C_{1-4}$alkyloxy- optionally substituted with $C_{1-4}$alkyloxy- or hydroxy; or $Het^3$ represents a heterocycle selected from morpholinyl, piperazinyl, piperidinyl, furanyl or pyrrolidinyl wherein said $Het^3$ is substituted with one or where possible two or more substituents selected from $NR^{35}R^{36}$, $C_{1-4}$alkyl-sulfonyl-$C_{1-4}$alkyl- or $C_{1-4}$alkyloxy- optionally substituted with $C_{1-4}$alkyloxy- or hydroxy;

$Het^4$ represents a heterocycle selected from morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said $Het^4$ is substituted with one or where possible two or more substituents selected from $C_{1-4}$alkyl-sulfonyl-$C_{1-4}$alkyl-, $C_{1-4}$alkyloxy- optionally substituted with $C_{1-4}$alkyloxy- or hydroxy;

$Het^5$ represents a heterocycle selected from furanyl, piperazinyl, 1,1-dioxothiomorpholinyl, piperazininonyl, piperidinyl, tetrahydro-1,1-dioxido-2H-thiopyranyl, piperidinonyl, morpholinyl or pyrrolidinyl wherein said $Het^5$ is optionally substituted with hydroxy, amino, mono- or di($C_{1-4}$alkyl)-amino-, $C_{1-4}$alkyl, $Het^6$ and $Het^7$ each independently represents a heterocycle selected from piperazinyl, piperidinyl or pyrrolidinyl wherein said heterocycles are optionally substituted with one or more substituents selected from hydroxy-, amino, hydroxy-$C_{1-4}$alkyl-, $C_{1-4}$alkyloxy-$C_{1-4}$alkyl- and $C_{1-4}$alkyl-;

$Het^8$ represents a heterocycle selected from tetrahydropyranyl, tetrahydrofuranyl, 1,1-dioxothiomorpholinyl, piperazininonyl, tetrahydro-1,1-dioxido-2H-thiopyranyl, piperidinonyl, azetidinyl or 2-azetidinonyl wherein said $Het^8$ is optionally substituted with aminosulfonyl, aminocarbonyl, mono- or di($C_{1-4}$alkyl)aminocarbonyl-, mono- or di($C_{1-4}$ alkyl)aminosulfonyl-, or $C_{1-4}$alkyl- optionally substituted with one or more substituents selected from amino, mono- or di($C_{1-4}$alkyl)amino-, $NR^{33}R^{34}$, C$_{1-4}$alkylsulfonyl, aminocarbonyloxy-, hydroxy-, C$_{1-4}$alkyloxy-, aminocarbonyl- and mono- or di(C$_{1-4}$alkyl)aminocarbonyl-, or C$_{1-4}$alkyloxycarbonyl optionally substituted with one or more substituents selected from hydroxy, C$_{1-4}$alkyloxy- and C$_{1-4}$alkylsulfonyl-, or C$_{1-4}$alkylcarbonyl optionally substituted with one or more substituents selected from hydroxy, C$_{1-4}$alkyloxy- and C$_{1-4}$alkylsulfonyl-; or Het$^8$ represents a heterocycle selected from furanyl, piperidinyl or piperazinyl wherein said Het$^8$ is substituted with aminocarbonyl, mono- or di(C$_{1-4}$alkyl)aminocarbonyl-, mono- or di(C$_{1-4}$alkyl)aminosulfonyl-, or C$_{1-4}$alkyl- substituted with one or more substituents selected from NR$^{33}$R$^{34}$, C$_{1-4}$alkylsulfonyl, aminocarbonyloxy-, hydroxy-, C$_{1-4}$alkyloxy-, aminocarbonyl- and mono- or di(C$_{1-4}$alkyl)aminocarbonyl-, or C$_{1-4}$alkyloxycarbonyl optionally substituted with one or more substituents selected from hydroxy, C$_{1-4}$alkyloxy- and C$_{1-4}$alkylsulfonyl-, or C$_{1-4}$alkylcarbonyl optionally substituted with one or more substituents selected from hydroxy, C$_{1-4}$alkyloxy- and C$_{1-4}$alkylsulfonyl-;

Het$^9$ and Het$^{10}$ each independently represents a heterocycle selected from piperazinyl, piperidinyl or pyrrolidinyl wherein said heterocycles are optionally substituted with one or more substituents selected from hydroxy-, amino, hydroxy-C$_{1-4}$alkyl-, C$_{1-4}$alkyloxy-C$_{1-4}$alkyl- and C$_{1-4}$alkyl-;

Het$^{11}$ represents 2-imidazolidinonyl- or

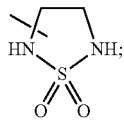

Het$^{12}$ represents a heterocycle selected from morpholinyl, piperazinyl, piperidinyl or pyrrolidinyl wherein said Het$^{12}$ is optionally substituted with one or where possible two or more substituents selected from hydroxy, amino or C$_{1-4}$alkyl-;

Het$^{13}$ represents a heterocycle selected from furanyl, piperazinyl, 1,1-dioxothiomorpholinyl, piperazininonyl, piperidinyl, tetrahydro-1,1-dioxido-2H-thiopyranyl, piperidinonyl, morpholinyl, piperazinyl or pyrrolidinyl;

Het$^{14}$ and Het$^{15}$ each independently represent a heterocycle selected from morpholinyl, piperazinyl, piperidinyl or pyrrolidinyl wherein said Het$^{14}$ and Het$^{15}$ are optionally substituted with one or where possible two or more substituents selected from hydroxy, amino or C$_{1-4}$alkyl;

Het$^{16}$ represents a heterocycle selected from piperidinyl or pyrrolidinyl;

Het$^{20}$ represents pyrrolidinyl, 2-pyrrolidinonyl, piperidinyl or hydroxy-pyrrolidinyl, preferably pyrrolidinyl or hydroxy-pyrrolidinyl;

Het$^{21}$ represents pyrrolidinyl or hydroxy-pyrrolidinyl;

Het$^{22}$ represents pyrrolidinyl, piperazinyl or piperidinyl;

Het$^{23}$ and Het$^{25}$ each independently represents a heterocycle selected from morpholinyl, pyrrolidinyl, piperazinyl or piperidinyl wherein said Het$^{23}$ is optionally substituted with one or where possible two or more substituents selected from C$_{1-4}$alkyl, C$_{3-6}$cycloalkyl, hydroxy-C$_{1-4}$alkyl-, C$_{1-4}$alkyloxyC$_{1-4}$alkyl or polyhydroxy-C$_{1-4}$ alkyl-;

Het$^{24}$ represents morpholinyl, pyrrolidinyl, piperazinyl or piperidinyl;

Ar$^4$, Ar$^5$ or Ar$^6$ each independently represent phenyl optionally substituted with nitro, cyano, C$_{1-4}$alkylsulfonyl-, C$_{1-4}$alkylsulfonylamino-, aminosulfonylamino-, hydroxy-C$_{1-4}$alkyl, aminosulfonyl-, hydroxy-, C$_{1-4}$alkyloxy- or C$_{1-4}$alkyl, preferably Ar$^4$ or Ar$^5$ each independently represent phenyl optionally substituted with cyano;

further characterised in that either

Y represents —C$_{1-2}$alkyl-NR$^{23}$—CO—CR$^{16}$R$^{17}$—NH—;

Het$^1$ represents 2-bora-1,3-dioxolanyl optionally substituted with one or where possible two, three, four or more substituents selected from amino, C$_{1-4}$alkyl, hydroxy-C$_{1-4}$alkyl-, phenyl, phenyl-C$_{1-4}$alkyl-, C$_{1-4}$alkyl-oxy-C$_{1-4}$alkyl-, mono- or di(C$_{1-4}$alkyl)amino- or amino-carbonyl-;

R$^{13}$ represents C$_{1-6}$alkyloxycarbonyl optionally substituted with phenyl or R$^{13}$ represents Ar$^6$-sulfonyl or Het$^{24}$-C$_{1-4}$alkylcarbonyl; or R$^4$ represents C$_{1-4}$alkyloxy substituted with at least one substituent selected from C$_{1-4}$alkyloxy-C$_{1-4}$alkyloxy-, NR$^{37}$R$^{38}$-carbonyloxy-, Het$^5$-carbonyloxy-, NR$^7$R$^8$, NR$^9$R$^{10}$-carbonyl-, Het$^3$-carbonyl-, Het$^{13}$-oxy- or Het$^2$-; wherein R$^8$ represents Het$^7$-aminocarbonyl-; Het$^9$-oxycarbonyl-; Het$^{10}$-sulfonyl-;

C$_{1-4}$alkyloxycarbonyl; mono- or di(C$_{1-4}$alkyl)aminocarbonyl-; mono- or di(C$_{1-4}$alkyl)aminocarbonyl substituted with C$_{1-4}$alkylsulfonyl-; or C$_{1-4}$alkylcarbonyl optionally substituted with one or more substituents selected from C$_{1-4}$alkylsulfonyl, hydroxy- and C$_{1-4}$alkyloxy-; or R$^8$ represents C$_{1-4}$alkyl substituted with one or more substituents selected from hydroxy C$_{1-4}$alkylsulfonyl-, NR$^{25}$R$^{26}$, aminocarbonyloxy-, C$_{1-4}$alkylcarbonyloxy-, aminocarbonyl-, C$_{1-4}$alkyloxy-C$_{1-4}$alkyloxy-, and Het$^{11}$;

Het$^{13}$ represents C$_{1-6}$alkyloxycarbonyl optionally substituted with phenyl or R$^{13}$ represents Ar$^6$-sulfonyl or Het$^{24}$-C$_{1-4}$alkylcarbonyl; in particular morpholinyl-C$_{1-4}$alkyl; and Het$^2$ represents a heterocycle selected from morpholinyl, piperazinyl, piperidinyl, pyrrolidinyl or thiomorpholinyl said Het$^2$ substituted with one or where possible two or more substituents selected from C$_{1-4}$alkyl- substituted with one or more substituents selected from NR$^{27}$R$^{28}$, C$_{1-4}$alkylsulfonyl, aminocarbonyloxy-, aminocarbonyl- and mono- or di(C$_{1-4}$ alkyl)aminocarbonyl-; or C$_{1-4}$alkyloxy- optionally substituted with C$_{1-4}$alkyloxy-; or C$_{1-4}$alkyloxycarbonyl optionally substituted with one or more substituents selected from hydroxy, C$_{1-4}$alkyloxy- and C$_{1-4}$alkylsulfonyl-;

or C$_{1-4}$alkylcarbonyl optionally substituted with one or more substituents selected from hydroxy-, C$_{1-4}$alkyloxy- and C$_{1-4}$alkylsulfonyl-;

or Het$^2$ represents 1,1-dioxothiomorpholinyl optionally substituted with C$_{1-4}$alkyl- optionally substituted with one or more substituents selected from NR$^{27}$R$^{28}$, C$_{1-4}$alkylsulfonyl, aminocarbonyloxy-, aminocarbonyl- and mono- or di(C$_{1-4}$alkyl)aminocarbonyl-; or C$_{1-4}$alkyloxy- optionally substituted with C$_{1-4}$alkyloxy-; or $C_{1-4}$alkyloxycarbonyl optionally substituted with one or more substituents selected from hydroxy, $C_{1-4}$alkyloxy- and $C_{1-4}$alkylsulfonyl-;

or $C_{1-4}$alkylcarbonyl optionally substituted with one or more substituents selected from hydroxy-, $C_{1-4}$alkyloxy- and $C_{1-4}$alkylsulfonyl-.

As used in the foregoing definitions and hereinafter, halo is generic to fluoro, chloro, bromo and iodo;

$C_{1-2}$alkyl defines methyl or ethyl;

$C_{1-3}$alkyl defines straight and branched chain saturated hydrocarbon radicals having from 1 to 3 carbon atoms such as, for example, methyl, ethyl, propyl and the like;

$C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like;

$C_{1-5}$alkyl defines straight and branched chain saturated hydrocarbon radicals having from 1 to 5 carbon atoms such as, for example, methyl, ethyl, propyl, butyl, pentyl, 1-methylbutyl, 2,2-dimethylpropyl, 2,2-dimethylethyl and the like;

$C_{1-6}$alkyl is meant to include $C_{1-5}$alkyl and the higher homologues thereof having 6 carbon atoms such as, for example hexyl, 1,2-dimethylbutyl, 2-methylpentyl and the like;

$C_{1-7}$alkyl is meant to include $C_{1-6}$alkyl and the higher homologues thereof having 7 carbon atoms such as, for example 1,2,3-dimethylbutyl, 1,2-methylpentyl and the like;

$C_{3-9}$alkyl defines straight and branched chain saturated hydrocarbon radicals having from 3 to 9 carbon atoms such as propyl, butyl, pentyl, hexyl, heptyl, octyl, nonyl and the like;

$C_{2-4}$alkenyl defines straight and branched chain hydrocarbon radicals containing one double bond and having from 2 to 4 carbon atoms such as, for example vinyl, 2-propenyl, 3-butenyl, 2-butenyl and the like;

$C_{3-9}$alkenyl defines straight and branched chain hydrocarbon radicals containing one double bond and having from 3 to 9 carbon atoms such as, for example 2-propenyl, 3-butenyl, 2-butenyl, 2-pentenyl, 3-pentenyl, 3-methyl-2-butenyl, 3-hexenyl and the like;

$C_{2-6}$alkynyl defines straight and branched chain hydrocarbon radicals containing one triple bond and having from 2 to 6 carbon atoms such as, for example, 2-propynyl, 3-butynyl, 2-butynyl, 2-pentynyl, 3-pentynyl, 3-methyl-2-butynyl, 3-hexynyl and the like;

$C_{3-6}$cycloalkyl is generic to cyclopropyl, cyclobutyl, cyclopentyl and cyclohexyl;

$C_{1-4}$alkyloxy defines straight or branched saturated hydrocarbon radicals such as methoxy, ethoxy, propyloxy, butyloxy, 1-methylethyloxy, 2-methylpropyloxy and the like;

$C_{1-6}$alkyloxy is meant to include $C_{1-4}$alkyloxy and the higher homologues such as methoxy, ethoxy, propyloxy, butyloxy, 1-methylethyloxy, 2-methylpropyloxy and the like;

polyhydroxy-$C_{1-4}$alkyl is generic to a $C_{1-4}$alkyl as defined hereinbefore, having two, three or where possible more hydroxy substituents, such as for example trifluoromethyl.

As used in the foregoing definitions and hereinafter, the term formyl refers to a radical of formula —CH(=O). When $X^1$ represents the divalent radical —O—N=CH—, said radical is attached with the carbon atom to the $R^3$, $R^4$ bearing cyclic moiety of the compounds of formula (I) and when $X^2$ represents the divalent radical —O—N=CH—, said radical is attached with the carbon atom to the $R^1$, $R^2$ bearing phenyl moiety of the compounds of formula (I).

The heterocycles as mentioned in the above definitions and hereinafter, are meant to include all possible isomeric forms thereof, for instance pyrrolyl also includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 1,3,4-oxadiazolyl; thiadiazolyl includes 1,2,3-thiadiazolyl, 1,2,4-thiadiazolyl, 1,2,5-thiadiazolyl and 1,3,4-thiadiazolyl; pyranyl includes 2H-pyranyl and 4H-pyranyl.

Further, the heterocycles as mentioned in the above definitions and hereinafter may be attached to the remainder of the molecule of formula (I) through any ring carbon or heteroatom as appropriate. Thus, for example, when the heterocycle is imidazolyl, it may be a 1-imidazolyl, 2-imidazolyl, 3-imidazolyl, 4-imidazolyl and 5-imidazolyl; when it is thiazolyl, it may be 2-thiazolyl, 4-thiazolyl and 5-thiazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl; when it is benzothiazolyl, it may be 2-benzothiazolyl, 4-benzothiazolyl, 5-benzothiazolyl, 6-benzothiazolyl and 7-benzothiazolyl.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are meant to comprise the therapeutically active non-toxic base addition salt forms which the compounds of formula (I) are able to form. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine.

Conversely said salt forms can be converted by treatment with an appropriate base or acid into the free acid or base form.

The term addition salt as used hereinabove also comprises the solvates which the compounds of formula (I) as well as the salts thereof, are able to form. Such solvates are for example hydrates, alcoholates and the like.

The term stereochemically isomeric forms as used hereinbefore defines the possible different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

The N-oxide forms of the compounds of formula (I) are meant to comprise those compounds of formula (I) wherein one or several nitrogen atoms are oxidized to the so-called N-oxide.

A first group of compounds according to the present invention consists of those compounds of formula (I) wherein one or more of the following restrictions apply;

Z represents NH;

Y represents —$C_{3-9}$alkyl-, —$C_{2-9}$alkenyl-, —$C_{1-5}$alkyl-oxy-$C_{1-5}$alkyl-, —$C_{1-5}$alkyl-NR$^{13}$—$C_{1-5}$alkyl-, —$C_{1-5}$alkyl-NR$^{14}$—CO—$C_{1-5}$alkyl-, —$C_{1-6}$alkyl-NH—CO—, —NH—CO—$C_{1-6}$alkyl-, —CO—$C_{1-7}$alkyl-, —$C_{1-7}$alkyl-CO—, $C_{1-6}$alkyl-CO—$C_{1-6}$alkyl, —$C_{1-2}$alkyl-NR$^{23}$—CO—CR$^{16}$R$^{17}$—NH—, —$C_{1-2}$alkyl-CO—NH—CR$^{18}$R$^{19}$—CO—, —$C_{1-2}$alkyl-CO—NR$^{20}$—$C_{1-3}$alkyl-CO—, —$C_{1-2}$alkyl-NR$^{21}$—CH$_2$—CO—NH—$C_{1-3}$alkyl-, —NR$^{22}$—CO—$C_{1-3}$alkyl-NH—, —$C_{1-3}$alkyl-NH—CO-Het$^{20}$-, $C_{1-2}$alkyl-CO-Het$^{21}$-CO—, or -Het$^{22}$-CH$_2$—CO—NH—$C_{1-3}$alkyl-;

X$^1$ represents O, —O—$C_{1-2}$alkyl-, —O—N=CH—, NR$^{11}$ or —NR$^{11}$—$C_{1-2}$alkyl-; in a particular embodiment X$^1$ represents O, —O—$C_{1-2}$alkyl- or NR$^{11}$—$C_{1-2}$alkyl-;

X$^2$ represents a direct bond, $C_{1-2}$alkyl, O, —O—$C_{1-2}$alkyl-, CO, —CO—$C_{1-2}$alkyl-, —O—N=CH—, NR$^{12}$ or NR$^{12}$—$C_{1-2}$alkyl-; in a particular embodiment X$^2$ represents a direct bond, —O—, —O—$C_{1-2}$alkyl, —CO—$C_{1-2}$alkyl- or NR$^{12}$—$C_{1-2}$alkyl-;

R$^1$ represents hydrogen, cyano, halo or hydroxy, preferably halo;

R$^2$ represents hydrogen, cyano, halo, hydroxy, hydroxycarbonyl-, $C_{1-4}$alkyloxycarbonyl-, Het$^{16}$-carbonyl-, $C_{1-4}$alkyl-, $C_{2-6}$alkynyl-, Ar$^5$, Het$^1$ or dihydroxyborane;

R$^3$ represents hydrogen, cyano, halo, hydroxy, formyl, $C_{1-6}$alkoxy-, $C_{1-6}$alkyl-, $C_{1-6}$alkoxy- substituted with halo, or R$^3$ represents $C_{1-4}$alkyl substituted with one or where possible two or more substituents selected from hydroxy or halo;

R$^4$ represents Ar$^4$-$C_{1-4}$alkyloxy-, $C_{1-4}$alkyloxy- or R$^4$ represents $C_{1-4}$alkyloxy substituted with one or where possible two or more substituents selected from hydroxy-, halo, $C_{1-4}$alkyloxy-, $C_{1-4}$alkyloxy-$C_{1-4}$alkyloxy-, NR$^{37}$R$^{38}$-carbonyloxy-, Het$^5$-carbonyloxy-, NR$^7$R$^8$, NR$^9$R$^{10}$-carbonyl-, Het$^3$-carbonyl-, Het$^{13}$-oxy- or Het$^2$-;

R$^7$ represents hydrogen or $C_{1-4}$alkyl;

R$^8$ represents $C_{3-6}$cycloalkyl, Het$^6$-carbonyl-, Het$^7$-aminocarbonyl-, Het$^8$, Het$^9$-oxycarbonyl-, Het$^{10}$-sulfonyl-, mono- or di($C_{1-4}$alkyl)aminocarbonyl-, mono- or di($C_{1-4}$alkyl)aminocarbonyl substituted with $C_{1-4}$alkylsulfonyl-, or $C_{1-4}$alkylcarbonyl optionally substituted with one or more substituents selected from $C_{1-4}$alkylsulfonyl, hydroxy- and $C_{1-4}$alkyloxy-, or R$^8$ represents $C_{1-4}$alkyl substituted with one or more substituents selected from $C_{1-4}$alkylsulfonyl-, NR$^{25}$R$^{26}$, aminocarbonyloxy-, aminocarbonyl-, $C_{1-4}$alyloxy-$C_{1-4}$alkyloxy-, and Het$^{11}$;

R$^9$ represents hydrogen or $C_{1-4}$alkyl-;

R$^{10}$ represents Het$^4$ or $C_{1-4}$alkyl- substituted with $C_{1-4}$alkylsulfonyl-;

R$^{11}$ represents hydrogen, $C_{1-4}$alkyl- or $C_{1-4}$alkyl-oxy-carbonyl-;

R$^{12}$ represents hydrogen, $C_{1-4}$alkyl-, $C_{1-6}$alkyloxycarbonyl- or $C_{1-6}$alkyloxycarbonyl-substituted with phenyl;

R$^{13}$ represents hydrogen, Het$^{14}$-$C_{1-4}$alkyl, $C_{1-6}$alkyloxycarbonyl optionally substituted with phenyl or R$^{13}$ represents Ar$^6$-sulfonyl or Het$^{24}$-$C_{1-4}$alkylcarbonyl; in particular morpholinyl-$C_{1-4}$alkyl;

R$^{14}$ and R$^{15}$ are each independently selected from hydrogen, $C_{1-4}$alkyl, Het$^{15}$-$C_{1-4}$alkyl- or $C_{1-4}$alkyloxy$C_{1-4}$alkyl-;

R$^{16}$ and R$^{17}$ each independently represents hydrogen, $C_{1-4}$alkyl or $C_{1-4}$alkyl substituted with hydroxy- or phenyl; or R$^{16}$ and R$^{17}$ taken together with the carbon atom to which they are attached form a $C_{3-6}$cycloalkyl;

R$^{18}$ represents hydrogen or $C_{1-4}$alkyl optionally substituted with hydroxy or phenyl;

R$^{19}$ represents hydrogen or $C_{1-4}$alkyl, in particular hydrogen or methyl, even more particular hydrogen;

R$^{20}$ represents hydrogen or $C_{1-4}$alkyl, in particular hydrogen or methyl;

R$^{21}$ represents hydrogen, $C_{1-4}$alkyl, Het$^{23}$-$C_{1-4}$alkylcarbonyl- or
R$^{21}$ represents mono- or di($C_{1-4}$alkyl)amino-$C_{1-4}$alkylcarbonyl- optionally substituted with hydroxy, pyrimidinyl, dimethylamine or $C_{1-4}$alkyloxy;

R$^{22}$ represents hydrogen or $C_{1-4}$alkyl optionally substituted with hydroxy or $C_{1-4}$alkyloxy;

R$^{23}$ represents $C_{1-4}$alkyl optionally substituted with hydroxy-, $C_{1-4}$alkyloxy- or Het$^{23}$; R$^{23}$ may also represent hydrogen when R$^{16}$ and R$^{17}$ taken together with the carbon atom to which they are attached form a $C_{3-6}$cycloalkyl;

R$^{25}$ and R$^{26}$ each independently represent hydrogen, $C_{1-4}$alkyl, $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-, in particular R$^{25}$ and R$^{26}$ each independently represent hydrogen, $C_{1-4}$alkyl, $C_{1-4}$alkylsulfonyl-, aminocarbonyl-, mono- or di($C_{1-4}$alkyl)aminocarbonyl- or $C_{1-4}$alkylcarbonyl-;

R$^{27}$ and R$^{28}$ each independently represent hydrogen, $C_{1-4}$alkyl, $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

R$^{29}$ and R$^{30}$ each independently represent hydrogen, aminosulfonyl, aminocarbonyl, mono- or di($C_{1-4}$alkyl)aminocarbonyl-, mono- or di($C_{1-4}$alkyl)aminosulfonyl-, or $C_{1-4}$alkyl- optionally substituted with one or more substituents selected from NR$^{31}$R$^{32}$, $C_{1-4}$alkylsulfonyl, aminocarbonyloxy-, hydroxy-, $C_{1-4}$alkyloxy-, aminocarbonyl- and mono- or di($C_{1-4}$alkyl)aminocarbonyl-, or $C_{1-4}$alkyloxycarbonyl optionally substituted with one or more substituents selected from hydroxy, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-;

R$^{31}$ and R$^{32}$ each independently represent hydrogen, $C_{1-4}$alkyl, $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

R$^{33}$ represents hydrogen or $C_{1-4}$alkyl;

R$^{34}$ represents $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

$R^{35}$ represents hydrogen or $C_{1-4}$alkyl;

$R^{36}$ represents $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

$R^{37}$ and $R^{38}$ each independently represent hydrogen, $C_{1-4}$alkyl, $C_{1-4}$alkylsulfonyl-, Het$^{12}$ or $C_{1-4}$alkyl substituted with one or more substituents selected from $C_{1-4}$alkylsulfonyl-, hydroxy- and $C_{1-4}$alkyloxy-;

$R^{39}$ and $R^{40}$ each independently represent aminosulfonyl, aminocarbonyl, mono- or di($C_{1-4}$alkyl)aminocarbonyl-, mono- or di($C_{1-4}$alkyl)aminosulfonyl-, or $C_{1-4}$alkyl- substituted with one or more substituents selected from $NR^{31}R^{32}$, $C_{1-4}$alkylsulfonyl, aminocarbonyloxy-, hydroxy-, $C_{1-4}$alkyloxy-, aminocarbonyl- and mono- or di($C_{1-4}$alkyl)aminocarbonyl-, or $C_{1-4}$alkyloxycarbonyl optionally substituted with one or more substituents selected from hydroxy, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-;

Het$^{1}$ represents thiazolyl or 2-bora-1,3-dioxolanyl wherein said Het$^{1}$ is optionally substituted with one or where possible two, three, four or more substituents selected from amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-, mono- or di($C_{1-4}$ alkyl)amino- or amino-carbonyl-;

Het$^{2}$ represents a heterocycle selected from tetrahydropyranyl, tetrahydrofuranyl, furanyl, 1,1-dioxothiomorpholinyl, piperazininonyl, tetrahydro-1,1-dioxido-2H-thiopyranyl, piperidinonyl, azetidinyl or 2-azetidinonyl wherein said Het$^{2}$ is optionally substituted with one or where possible two or more substituents selected from hydroxy, amino, $NR^{29}R^{30}$, aminocarbonyl, mono- or di($C_{1-4}$alkyl)aminocarbonyl, $C_{1-4}$alkylsulfonyl or $C_{1-4}$alkyl- optionally substituted with one or more substituents selected from $NR^{27}R^{28}$, $C_{1-4}$alkylsulfonyl, aminocarbonyloxy-, aminocarbonyl- and mono- or di($C_{1-4}$alkyl)aminocarbonyl-, or $C_{1-4}$alkyloxy- optionally substituted with $C_{1-4}$alkyloxy-, or $C_{1-4}$alkyloxycarbonyl optionally substituted with one or more substituents selected from hydroxy, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-; or Het$^{2}$ represents a heterocycle selected from morpholinyl, piperazinyl, piperidinyl or pyrrolidinyl wherein said morpholinyl, piperazinyl, piperidinyl or pyrrolidinyl are optionally substituted with one or where possible two or more substituents selected from $C_{1-4}$alkyl- optionally substituted with one or more substituents selected from $NR^{27}R^{28}$, $C_{1-4}$alkylsulfonyl, aminocarbonyloxy-, aminocarbonyl- and mono- or di($C_{1-4}$alkyl)aminocarbonyl-, or $C_{1-4}$alkyloxy- optionally substituted with $C_{1-4}$alkyloxy-, or $C_{1-4}$alkyloxycarbonyl optionally substituted with one or more substituents selected from hydroxy, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-;

Het$^{3}$ represents a heterocycle selected from tetrahydropyranyl, tetrahydrofuranyl, furanyl, 1,1-dioxothiomorpholinyl, piperazininonyl, tetrahydro-1,1-dioxido-2H-thiopyranyl, piperidinonyl, azetidinyl or 2-azetidinonyl wherein said Het$^{3}$ is optionally substituted with one or where possible two or more substituents hydroxy-, amino, $C_{1-4}$alkyl-, $C_{3-6}$cycloalkyl-$C_{1-4}$alkyl-, aminosulfonyl-, mono- or di($C_{1-4}$alkyl)aminosulfonyl-, amino-$C_{1-4}$alkyl-, Mono- or di($C_{1-4}$alkyl)amino-$C_{1-4}$alkyl, $NR^{35}R^{36}$, $C_{1-4}$alkyl-sulfonyl-$C_{1-4}$alkyl- or $C_{1-4}$alkyloxy- optionally substituted with $C_{1-4}$alkyloxy- or hydroxy; or Het$^{3}$ represents a heterocycle selected from morpholinyl, piperazinyl, piperidinyl or pyrrolidinyl wherein said Het$^{3}$ is optionally substituted with one or where possible two or more substituents selected from $NR^{35}R^{36}$, $C_{1-4}$alkyl-sulfonyl-$C_{1-4}$alkyl- or $C_{1-4}$alkyloxy- optionally substituted with $C_{1-4}$alkyloxy- or hydroxy;

Het$^{4}$ represents a heterocycle selected from morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said Het$^{4}$ is substituted with one or where possible two or more substituents selected from $C_{1-4}$alkyl-sulfonyl-$C_{1-4}$alkyl-, $C_{1-4}$alkyloxy- optionally substituted with $C_{1-4}$alkyloxy- or hydroxy;

Het$^{5}$ represents a heterocycle selected from furanyl, piperazinyl, 1,1-dioxothiomorpholinyl, piperazininonyl, piperidinyl, tetrahydro-1,1-dioxido-2H-thiopyranyl, piperidinonyl, morpholinyl or pyrrolidinyl wherein said Het$^{5}$ is optionally substituted with hydroxy, amino, mono- or di($C_{1-4}$alkyl)-amino-, $C_{1-4}$alkyl, Het$^{6}$ and Het$^{7}$ each independently represents a heterocycle selected from piperazinyl, piperidinyl or pyrrolidinyl wherein said heterocycles are optionally substituted with one or more substituents selected from hydroxy-, amino-, hydroxy-$C_{1-4}$alkyl-, $C_{1-4}$alkyloxy-$C_{1-4}$alkyl- and $C_{1-4}$alkyl-;

Het$^{8}$ represents a heterocycle selected from tetrahydropyranyl, tetrahydrofuranyl, 1,1-dioxothiomorpholinyl, piperazininonyl, tetrahydro-1,1-dioxido-2H-thiopyranyl, piperidinonyl, azetidinyl or 2-azetidinonyl wherein said Het$^{8}$ is optionally substituted with aminosulfonyl, aminocarbonyl, mono- or di($C_{1-4}$alkyl)aminocarbonyl-, mono- or di($C_{1-4}$alkyl)aminosulfonyl-, or $C_{1-4}$alkyl- optionally substituted with one or more substituents selected from amino, mono- or di($C_{1-4}$alkyl)amino-, $NR^{33}R^{34}$, $C_{1-4}$alkylsulfonyl, aminocarbonyloxy-, hydroxy-, $C_{1-4}$alkyloxy-, aminocarbonyl- and mono- or di($C_{1-4}$alkyl)aminocarbonyl-, or $C_{1-4}$alkyloxycarbonyl optionally substituted with one or more substituents selected from hydroxy-, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-; or Het$^{8}$ represents a heterocycle selected from furanyl, piperidinyl or piperazinyl wherein said Het$^{8}$ is substituted with aminocarbonyl, mono- or di($C_{1-4}$alkyl)aminocarbonyl-, mono- or di($C_{1-4}$alkyl)aminosulfonyl-, or $C_{1-4}$alkyl- substituted with one or more substituents selected from $NR^{33}R^{34}$, $C_{1-4}$alkylsulfonyl, aminocarbonyloxy-, hydroxy-, $C_{1-4}$alkyloxy-, aminocarbonyl- and mono- or di($C_{1-4}$alkyl)aminocarbonyl-, or $C_{1-4}$alkyloxycarbonyl optionally substituted with one or more substituents selected from hydroxy-, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-;

$Het^9$ and $Het^{10}$ each independently represents a heterocycle selected from piperazinyl, piperidinyl or pyrrolidinyl wherein said heterocycles are optionally substituted with one or more substituents selected from hydroxy-, amino, hydroxy-$C_{1-4}$alkyl-, $C_{1-4}$alkyloxy-$C_{1-4}$alkyl- and $C_{1-4}$alkyl-;

$Het^{11}$ represents 2-imidazolidinonyl- or

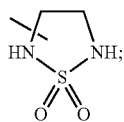

$Het^{12}$ represents a heterocycle selected from morpholinyl, piperazinyl, piperidinyl or pyrrolidinyl wherein said $Het^{12}$ is optionally substituted with one or where possible two or more substituents selected from hydroxy-, amino or $C_{1-4}$alkyl-;

$Het^{13}$ represents a heterocycle selected from furanyl, piperazinyl, 1,1-dioxothiomorpholinyl, piperazininonyl, piperidinyl, tetrahydro-1,1-dioxido-2H-thiopyranyl, piperidinonyl, morpholinyl, piperazinyl or pyrrolidinyl $Het^{16}$ represents a heterocycle selected from piperidinyl or pyrrolidinyl;

$Het^{20}$ represents pyrrolidinyl, 2-pyrrolidinonyl, piperidinyl or hydroxy-pyrrolidinyl, preferably pyrrolidinyl or hydroxy-pyrrolidinyl;

$Het^{21}$ represents pyrrolidinyl or hydroxy-pyrrolidinyl;

$Het^{22}$ represents pyrrolidinyl, piperazinyl or piperidinyl;

$Het^{23}$ represents a heterocycle selected from morpholinyl, pyrrolidinyl, piperazinyl or piperidinyl wherein said $Het^{23}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Ar^4$, $Ar^5$ or $Ar^6$ each independently represent phenyl optionally substituted with nitro, cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl, preferably $Ar^4$ or $Ar^5$ each independently represent phenyl optionally substituted with cyano;

further characterised in that either

Y represents —$C_{1-2}$alkyl-$NR^{23}$—CO—$CR^{16}R^{17}$—NH—;

$Het^1$ represents 2-bora-1,3-dioxolanyl optionally substituted with one or where possible two, three, four or more substituents selected from amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-, mono- or di($C_{1-4}$alkyl) amino- or amino-carbonyl-;

$R^{13}$ represents $C_{1-6}$alkyloxycarbonyl optionally substituted with phenyl or $R^{13}$ represents $Ar^6$-sulfonyl or $Het^{24}$-$C_{1-4}$alkylcarbonyl; or $R^4$ represents $C_{1-4}$alkyloxy substituted with at least one substituent selected from $C_{1-4}$alkyloxy-$C_{1-4}$alkyloxy-, $NR^{37}R^{38}$-carbonyloxy-, $Het^5$-carbonyloxy-, $NR^7R^8$, $NR^9R^{10}$-carbonyl-, $Het^3$-carbonyl-, $Het^{13}$-oxy- or $Het^2$-.

Another group of compounds according to the present invention consists of those compounds of formula (I) wherein one or more of the following restrictions apply;

Z represents NH;

Y represents —$C_{3-9}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-6}$alkyl-CO—NH—, —$C_{1-6}$alkyl-NH—CO—, —$C_{1-2}$alkyl-$NR^{23}$—CO—$CR^{16}R^{17}$—NH—, —$C_{1-2}$alkyl-$NR^{21}$—$CH_2$—CO—NH—$C_{1-3}$alkyl or $C_{1-3}$alkyl-NH—CO-$Het^{20}$-; in particular Y represents —$C_{3-9}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-6}$alkyl-CO—NH—, —$C_{1-6}$alkyl-NH—CO—, —$C_{1-2}$alkyl-$NR^{23}$—CO—$CR^{16}R^{17}$—NH— or $C_{1-3}$alkyl-NH—CO-$Het^{20}$-

$X^1$ represents a direct bond, O, —O—$C_{1-2}$alkyl-, $NR^{11}$, or —$NR^{11}$—$C_{1-2}$alkyl-;

$X^2$ represents a direct bond, —$C_{1-2}$alkyl-, CO—$C_{1-2}$alkyl or $NR^{12}$—$C_{1-2}$alkyl-; in particular $X^2$ represents a direct bond, —$C_{1-2}$alkyl- or $NR^{12}$—$C_{1-2}$alkyl-;

$R^1$ represents hydrogen, cyano, halo or hydroxy;

$R^2$ represents hydrogen, halo, cyano, $C_{2-6}$alkynyl, hydroxy, hydroxycarbonyl, $C_{1-4}$alkyloxycarbonyl- or $Het^1$; in particular $R^2$ represents hydrogen, halo, cyano, acetylene (—C≡CH), hydroxy, hydroxycarbonyl, $C_{1-4}$alkyloxycarbonyl- or $Het^1$; more in particular $R^2$ represents hydrogen, halo, cyano, hydroxy, hydroxycarbonyl, $C_{1-4}$alkyloxycarbonyl- or $Het^1$ $R^3$ represents hydrogen, cyano, halo, hydroxy, formyl, $C_{1-6}$alkyloxy or $C_{1-6}$alkyloxy-substituted with halo;

$R^4$ represents $Ar^4$—$C_{1-4}$alkyloxy, $C_{1-4}$alkyloxy-, or $C_{1-4}$alkyloxy- substituted with one or where possible two or more substituents selected from hydroxy, $C_{1-4}$alkyloxy-, $C_{1-4}$alkyloxy-$C_{1-4}$alkyloxy, $NR^7R^8$ or $Het^2$; in particular $R^4$ represents $Ar^4$—$C_{1-4}$alkyloxy, $C_{1-4}$alkyloxy-, or $C_{1-4}$alkyloxy- substituted with one or where possible two or more substituents selected from $C_{1-4}$alkyloxy-, $C_{1-4}$alkyloxy-$C_{1-4}$alkyloxy or $NR^7R^8$ $R^7$ represents hydrogen, hydroxy$C_{1-4}$alkyl- or $C_{1-4}$alkyl;

$R^8$ represents $C_{1-4}$alkyloxycarbonyl or $C_{1-4}$alkyl- substituted with one or more substituents selected from $C_{1-4}$alkylsulfonyl-, $C_{1-4}$alkylcarbonyloxy or $NR^{25}R^{26}$; in particular $R^8$ represents $C_{1-4}$alkyl- substituted with one or more substituents selected from $C_{1-4}$alkylsulfonyl- or $NR^{25}R^{26}$;

$R^{11}$ represents hydrogen, $C_{1-4}$alkyloxycarbonyl or $C_{1-4}$alkyl; in particular $R^{11}$ represents hydrogen or $C_{1-4}$alkyl;

$R^{12}$ represents hydrogen or $C_{1-4}$alkyl;

$R^{13}$ represents $C_{1-6}$alkyloxycarbonyl optionally substituted with phenyl or $R^{13}$ represents $Ar^6$-sulfonyl or $Het^{24}$-$C_{1-4}$alkylcarbonyl;

$R^{14}$ and $R^{15}$ each independently represent hydrogen or $C_{1-4}$alkyl; in particular $R^{14}$ and $R^{15}$ each independently represent hydrogen;

$R^{16}$ and $R^{17}$ each independently represent hydrogen or $C_{1-4}$alkyl optionally substituted with $C_{3-6}$cycloalkyl or $R^{16}$ and $R^{17}$ taken together with the carbon atom to which they are attached form a $C_{3-6}$cycloalkyl; in a particular embodiment $R^{16}$ and $R^{17}$ taken together with the carbon atom to which they are attached form a $C_{3-6}$cycloalkyl;

$R^{21}$ represents hydrogen or $C_{1-4}$alkyloxycarbonyl; in particular $R^{21}$ represents $C_{1-4}$alkyloxycarbonyl $R^{23}$ represents $C_{1-4}$alkyl optionally substituted with hydroxy-, $C_{1-4}$alkyloxy- or $Het^{25}$; $R^{23}$ may also represent hydrogen when $R^{16}$ and $R^{17}$ taken together with the carbon atom to which they are attached form a $C_{3-6}$cycloalkyl;

$R^{25}$ and $R^{26}$ each independently represent hydrogen, $C_{1-4}$alkyl, $C_{1-4}$alkylsulfonyl, $C_{1-4}$alkyloxycarbonyl or $C_{1-4}$alkylcarbonyl; in particular $R^{25}$ and $R^{26}$ each independently represents hydrogen or $C_{1-4}$alkylcarbonyl;

$R^{27}$ and $R^{28}$ each independently represent hydrogen, $C_{1-4}$alkyl, $C_{1-4}$alkylsulfonyl, $C_{1-4}$alkyloxycarbonyl or $C_{1-4}$alkylcarbonyl; in particular $R^{27}$ and $R^{28}$ each independently represent hydrogen or $C_{1-4}$alkylcarbonyl;

$Het^1$ represents 2-bora-1,3-dioxolanyl- optionally substituted with one or where possible two, three, four or more substituents selected from amino, $C_{1-4}$alkyl, hydroxy-$C_{1-4}$alkyl-, phenyl, phenyl-$C_{1-4}$alkyl, $C_{1-4}$alkyloxy$C_{1-4}$alkyl-, mono- or di($C_{1-4}$alkyl)amino- or aminocarbonyl-;

$Het^2$ represents 1,1-dioxothiomorpholinyl optionally substituted with $C_{1-4}$alkyloxycarbonyl or $C_{1-4}$alkyl-$NR^{27}R^{28}$; or $Het^2$ represents piperidinyl or piperazinyl substituted with $C_{1-4}$alkyloxycarbonyl or —$C_{1-4}$alkyl-$NR^{27}R^{28}$;

$Het^{20}$ represents pyrrolidinyl, 2-pyrrolidinonyl, piperidinyl or hydroxy-pyrrolidinyl; in particular $Het^{20}$ represents pyrrolidinyl, piperidinyl or hydroxy-pyrrolidinyl; more in particular $Het^{20}$ represents pyrrolidinyl;

$Het^{25}$ represents a heterocycle selected from morpholinyl or piperazinyl wherein said heterocycle is optionally substituted with $C_{1-4}$alkyl, hydroxy-$C_{1-4}$alkyl, $C_{1-4}$alkyloxy-$C_{1-4}$ alkyl or polyhydroxy-$C_{1-4}$alkyl; or $Ar^4$, $Ar^5$ or $Ar^6$ each independently represents phenyl optionally substituted with nitro, cyano, hydroxy, hydroxy$C_{1-4}$alkyl, $C_{1-4}$alkyl or $C_{1-4}$alkyloxy;

further characterised in that either
Y represents —$C_{1-2}$alkyl-$NR^{23}$—CO—$CR^{16}R^{17}$—NH—; or
$R^4$ represents $C_{1-4}$alkyloxy substituted with at least one substituent selected from $C_{1-4}$alkyloxy-$C_{1-4}$alkyloxy-, $NR^7R^8$ or $Het^2$.

Another group of compounds according to the present invention consists of those compounds of formula (I) wherein one or more of the following restrictions apply;

Z represents NH;
Y represents —$C_{3-9}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-6}$alkyl-CO—NH—, —$C_{1-6}$alkyl-NH—CO—, —$C_{1-2}$alkyl-$NR^{23}$—CO—$CR^{16}R^{17}$—NH—, —$C_{1-2}$alkyl-$NR^{21}$—$CH_2$—CO—NH—$C_{1-3}$alkyl or $C_{1-3}$alkyl-NH—CO-$Het^{20}$-; in particular Y represents —$C_{3-9}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-6}$alkyl-CO—NH—, —$C_{1-6}$alkyl-NH—CO—, —$C_{1-2}$alkyl-$NR^{23}$—CO—$CR^{16}R^{17}$—NH— or $C_{1-3}$alkyl-NH—CO-$Het^{20}$-;

$X^1$ represents a direct bond, O, —O—$C_{1-2}$alkyl-, $NR^{11}$, or —$NR^{11}$—$C_{1-2}$alkyl-;

$X^2$ represents a direct bond, —$C_{1-2}$alkyl-, CO—$C_{1-2}$alkyl or $NR^{12}$—$C_{1-2}$alkyl-; in particular $X^2$ represents a direct bond, —$C_{1-2}$alkyl- or $NR^{12}$—$C_{1-2}$alkyl-;

$R^1$ represents hydrogen or halo;

$R^2$ represents hydrogen, halo, $C_{2-6}$alkynyl, cyano or $Het^1$; in particular $R^2$ represents hydrogen, halo, $C_{2-6}$alkynyl or $Het^1$; more in particular $R^2$ represents hydrogen, halo, acetylene or $Het^1$; or $R^2$ represents hydrogen, halo, cyano or $Het^1$;

$R^3$ represents hydrogen;

$R^4$ represents $Ar^4$-$C_{1-4}$alkyloxy, $C_{1-4}$alkyloxy-, or $C_{1-4}$alkyloxy- substituted with one or where possible two or more substituents selected from hydroxy, $C_{1-4}$alkyloxy-, $C_{1-4}$alkyloxy-$C_{1-4}$alkyloxy, $NR^7R^8$ or $Het^2$; in particular $R^4$ represents $Ar^4$-$C_{1-4}$alkyloxy, $C_{1-4}$alkyloxy-, or $C_{1-4}$alkyloxy- substituted with one or where possible two or more substituents selected from $C_{1-4}$alkyloxy-, $C_{1-4}$alkyloxy-$C_{1-4}$alkyloxy or $NR^7R^8$ $R^7$ represents hydrogen or $C_{1-4}$alkyl;

$R^8$ represents $C_{1-4}$alkyloxycarbonyl or $C_{1-4}$alkyl- substituted with one or more substituents selected from $C_{1-4}$alkylsulfonyl-, hydroxy, $C_{1-4}$alkylcarbonyloxy or $NR^{25}R^{26}$; in particular $R^8$ represents $C_{1-4}$alkyl- substituted with one or more substituents selected from $C_{1-4}$alkylsulfonyl- or $NR^{25}R^{26}$;

$R^{11}$ represents hydrogen or $C_{1-4}$alkyl;
$R^{12}$ represents hydrogen or $C_{1-4}$alkyl;
$R^{13}$ represents $Ar^6$-sulfonyl or $C_{1-6}$alkyloxycarbonyl optionally substituted with phenyl;
$R^{14}$ and $R^{15}$ represent hydrogen;
$R^{16}$ and $R^{17}$ each independently represent hydrogen or $C_{1-4}$alkyl optionally substituted with $C_{3-6}$cycloalkyl or $R^{16}$ and $R^{17}$ taken together with the carbon atom to which they are attached form a $C_{3-6}$cycloalkyl; in a particular embodiment $R^{16}$ and $R^{17}$ taken together with the carbon atom to which they are attached form a $C_{3-6}$cycloalkyl;
$R^{21}$ represents hydrogen or $C_{1-4}$alkyloxycarbonyl;
$R^{23}$ represents $C_{1-4}$alkyl optionally substituted with hydroxy-, $C_{1-4}$alkyloxy- or $Het^{25}$; $R^{23}$ may also represent hydrogen when $R^{16}$ and $R^{17}$ taken together with the carbon atom to which they are attached form a $C_{3-6}$cycloalkyl;
$R^{25}$ and $R^{26}$ each independently represent hydrogen or $C_{1-4}$alkylcarbonyl;
$R^{27}$ and $R^{28}$ each independently represent hydrogen or $C_{1-4}$alkylcarbonyl;
$Het^1$ represents 2-bora-1,3-dioxolanyl-;
$Het^2$ represents 1,1-dioxothiomorpholinyl, piperidinyl or piperazinyl wherein said $Het^2$ is optionally substituted with $C_{1-4}$alkyloxycarbonyl or —$C_{1-4}$alkyl-$NR^{27}R^{28}$;
$Het^{20}$ represents pyrrolidinyl;
$Het^{25}$ represents a heterocycle selected from morpholinyl or piperazinyl wherein said heterocycle is optionally substituted with $C_{1-4}$alkyl, hydroxy-$C_{1-4}$alkyl, $C_{1-4}$alkyloxy-$C_{1-4}$ alkyl or polyhydroxy-$C_{1-4}$alkyl;
$Ar^4$ represents phenyl;
$Ar^5$ represents phenyl; or
$Ar^6$ represents phenyl optionally substituted with nitro;
further characterised in that either
Y represents —$C_{1-2}$alkyl-$NR^{23}$—CO—$CR^{16}R^{17}$—NH—; or
$R^4$ represents $C_{1-4}$alkyloxy substituted with at least one substituent selected from $C_{1-4}$alkyloxy-$C_{1-4}$alkyloxy-, $NR^7R^8$ or $Het^2$; in particular $C_{1-4}$alkyloxy substituted with $C_{1-4}$alkyloxy-$C_{1-4}$alkyloxy- or $NR^7R^8$.

An interesting group of compounds consists of those compounds of formula (I) wherein one or more of the following restrictions apply:

Z represents NH;
Y represents —$C_{3-9}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-2}$alkyl-$NR^{21}$—$H_2$—CO—NH—$C_{1-3}$alkyl- or —$C_{1-2}$alkyl-$NR^{23}$—CO—$CR^{16}R^{17}$—NH—; in particular Y represents —$C_{3-9}$alkyl-, —$C_{1-5}$alkyl-$NR^{13}$—$C_{1-5}$alkyl- or —$C_{1-2}$alkyl-$NR^{23}$—CO—$CR^{16}R^{17}$—NH—

$X^1$ represents O or —O—$C_{1-2}$alkyl-; in particular $X^1$ represents O $X^2$ represents a direct bond, $C_{1-2}$alkyl, —CO—$C_{1-2}$alkyl or $NR^{12}$—$C_{1-2}$alkyl; in particular $X^2$ represents a direct bond or $NR^{12}$—$C_{1-2}$alkyl-;

$R^1$ represents hydrogen or halo; in particular $R^1$ represents hydrogen;

$R^2$ represents halo, $C_{2-6}$alkynyl, cyano or $Het^1$; in particular $R^2$ represents halo, acetylene or $Het^1$; more in particular $R^2$ represents halo or $Het^1$;

$R^3$ represents hydrogen;

$R^4$ represents $Ar^4$—$C_{1-4}$alkyloxy-, $C_{1-4}$alkyloxy- or $C_{1-4}$alkyloxy substituted with one or where possible two or more substituents selected from $Het^2$, $NR^7R^8$, hydroxy and $C_{1-4}$alkyloxy-$C_{1-4}$alkyloxy-; in particular $R^4$ represents $Ar^4$—$C_{1-4}$alkyloxy-, $C_{1-4}$alkyloxy- or $C_{1-4}$alkyloxy substituted with $C_{1-4}$alkyloxy-$C_{1-4}$alkyloxy-;

$R^7$ represents hydrogen or $C_{1-4}$alkyl;

$R^8$ represents $C_{1-4}$alkyl substituted with $NR^{25}R^{26}$ or $C_{1-4}$alkylsulfonyl;

$R^{12}$ represents hydrogen or $C_{1-4}$alkyl-;

$R^{13}$ represents $Ar^6$-sulfonyl or $C_{1-6}$alkyloxycarbonyl optionally substituted with phenyl;

$R^{16}$ and $R^{17}$ represents hydrogen, $C_{1-4}$alkyl or $R^{16}$ and $R^{17}$ taken together with the carbon atom to which they are attached from a $C_{3-6}$cycloalkyl;

$R^{23}$ represents hydrogen or $C_{1-4}$alkyl; in particular $R^{23}$ represents $C_{1-4}$alkyl and $R^{23}$ represents hydrogen when $R^{16}$ and $R^{17}$ taken together with the carbon atom to which they are attached from a $C_{3-6}$cycloalkyl;

$R^{25}$ and $R^{26}$ each independently represent hydrogen or $C_{1-4}$alkylcarbonyl;

$R^{27}$ and $R^{28}$ each independently represent hydrogen or $C_{1-4}$alkylcarbonyl;

$Het^1$ represents 2-bora-1,3-dioxolanyl;

$Het^2$ represents piperidinyl, piperazinyl, morpholinyl, thiomorpholinyl or 1,1-dioxothiomorpholinyl wherein said $Het^2$ is optionally substituted with $C_{1-4}$alkyloxycarbonyl or $NR^{27}R^{28}$—$C_{1-4}$alkyl; in particular $Het^2$ represents 1,1-dioxothiomorpholinyl; piperidinyl substituted with $C_{1-4}$alkyloxycarbonyl; or piperazinyl substituted with $C_{1-4}$alkyloxycarbonyl or $NR^{27}R^{28}$—$C_{1-4}$alkyl-;

$Ar^4$ represents phenyl;

$Ar^5$ represents phenyl; or $Ar^6$ represents phenyl optionally substituted with nitro.

An interesting group of compounds consists of those compounds of formula (I) wherein one or more of the following restrictions apply:

Z represents NH;

Y represents —$C_{3-9}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-2}$alkyl-$NR^{21}$—$CH_2$—CO—NH—$C_{1-3}$alkyl-, $C_{1-6}R^{17}$—CO— or —$C_{1-2}$alkyl-$NR^{23}$—CO—$CR^{16}R^{17}$—NH—; in particular Y represents —$C_{3-9}$alkyl-, $C_{1-6}$alkyl-NH—CO—$C_{1-5}$alkyl-$NR^{13}$—$C_{1-5}$alkyl-, —$C_{1-5}$alkyl-$NR^{14}$—CO—$C_{1-5}$alkyl-, or —$C_{1-2}$alkyl-$NR^{23}$—CO—$CR^{16}R^{17}$—NH—

$X^1$ represents O or —O—$C_{1-2}$alkyl-; in particular $X^1$ represents O $X^2$ represents a direct bond, $C_{1-2}$alkyl, —CO—$C_{1-2}$alkyl or $NR^{12}$—$C_{1-2}$alkyl; in particular $X^2$ represents —CO—$C_{1-2}$alkyl or $NR^{12}$—$C_{1-2}$alkyl-;

$R^1$ represents hydrogen, cyano or halo; in particular $R^1$ represents hydrogen or halo, more in particular $R^1$ represents hydrogen, fluoro or bromo;

$R^2$ represents halo, $C_{2-6}$alkynyl, cyano or $Het^1$; in particular $R^2$ represents halo, acetylene or $Het^1$; more in particular $R^2$ represents halo or $Het^1$;

$R^3$ represents hydrogen;

$R^4$ represents $Ar^4$-$C_{1-4}$alkyloxy-, $C_{1-4}$alkyloxy- or $C_{1-4}$alkyloxy substituted with one or where possible two or more substituents selected from $Het^2$, $NR^7R^8$, hydroxy and $C_{1-4}$alkyloxy-$C_{1-4}$alkyloxy-; in particular $R^4$ represents $Ar^4$-$C_{1-4}$alkyloxy-, $C_{1-4}$alkyloxy- or $C_{1-4}$alkyloxy substituted with one or where possible two or more substituents selected from $Het^2$, $NR^7R^8$ or hydroxy;

$R^7$ represents hydrogen, hydroxy-$C_{1-4}$alkyl- or $C_{1-4}$alkyl;

$R^8$ represents $C_{1-4}$alkylcarbonyl, $C_{1-4}$alkyloxycarbonyl or $C_{1-4}$alkyl substituted with hydroxy-$C_{1-4}$alkyloxy-, $NR^{25}R^{26}$, $C_{1-4}$alkylcarbonyloxy- or $C_{1-4}$alkylsulfonyl;

$R^{12}$ represents hydrogen or $C_{1-4}$alkyl-;

$R^{13}$ represents $Ar^6$-sulfonyl or $C_{1-6}$alkyloxycarbonyl optionally substituted with phenyl;

$R^{16}$ and $R^{17}$ each independently represents hydrogen, $C_{1-4}$alkyl or $R^{16}$ and $R^{17}$ taken together with the carbon atom to which they are attached from a $C_{3-6}$cycloalkyl;

$R^{23}$ represents $C_{1-4}$alkyl optionally substituted with $Het^{25}$;

$R^{23}$ may also represent hydrogen when $R^{16}$ and $R^{17}$ taken together with the carbon atom to which they are attached form a $C_{3-6}$cycloalkyl;

$R^{25}$ and $R^{26}$ each independently represent hydrogen or $C_{1-4}$alkylcarbonyl;

$R^{27}$ and $R^{28}$ each independently represent hydrogen or $C_{1-4}$alkylcarbonyl;

$Het^1$ represents 2-bora-1,3-dioxolanyl;

$Het^2$ represents piperidinyl, piperazinyl, morpholinyl, thiomorpholinyl or 1,1-dioxothiomorpholinyl wherein said $Het^2$ is optionally substituted with $C_{1-4}$alkyloxycarbonyl or $NR^{27}R^{28}$—$C_{1-4}$alkyl; in particular $Het^2$ represents 1,1-dioxothiomorpholinyl; piperidinyl substituted with $C_{1-4}$alkyloxycarbonyl; or piperazinyl substituted with $C_{1-4}$alkyloxycarbonyl or $NR^{27}R^{28}$—$C_{1-4}$alkyl-;

$Het^{25}$ represents morpholinyl;

$Ar^4$ represents phenyl;

$Ar^5$ represents phenyl; or $Ar^6$ represents phenyl optionally substituted with nitro.

A further interesting group of compounds consists of those compounds of formula (I) wherein one or more of the following restrictions apply:

Z represents NH; Y represents —$C_{3-9}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-2}$alkyl-$NR^{21}$—$H_2$—CO—NH—$C_{1-3}$alkyl- or $C_{1-2}$alkyl-$NR^{23}$—CO—$CR^{16}R^{17}$—NH—;

$X^1$ represents O or —O—$C_{1-2}$alkyl-; $X^2$ represents a direct bond, $C_{1-2}$alkyl, —CO—$C_{1-2}$alkyl or $NR^{12}$—$C_{1-2}$alkyl;

$R^1$ represents hydrogen or halo; $R^2$ represents halo, acetylene or $Het^1$ $R^3$ represents hydrogen or cyano; $R^4$ represents $Ar^4$-$C_{1-4}$alkyloxy-, $C_{1-4}$alkyloxy- or $C_{1-4}$alkyloxy substituted with one or where possible two or more substituents selected from $Het^2$, $NR^7R^8$, hydroxy and $C_{1-4}$alkyloxy-$C_{1-4}$alkyloxy-;

$R^7$ represents hydrogen or $C_{1-4}$alkyl; $R^8$ represents $C_{1-4}$alkyl substituted with $NR^{25}R^{26}$ or $C_{1-4}$alkylsulfonyl;

$R^{12}$ represents hydrogen or $C_{1-4}$alkyl-; $R^{13}$ represents $Ar^6$-sulfonyl or $C_{1-6}$alkyloxycarbonyl optionally substituted with phenyl;

$R^{16}$ and $R^{17}$ represents hydrogen, $C_{1-4}$alkyl or $R^{16}$ and $R^{17}$ taken together with the carbon atom to which they are attached from a $C_{3-6}$cycloalkyl;

$R^{23}$ represents $C_{1-4}$alkyl and $R^{23}$ represents hydrogen when $R^{16}$ and $R^{17}$ taken together with the carbon atom to which they are attached from a $C_{3-6}$cycloalkyl;

$R^{25}$, $R^{26}$, $R^{27}$ and $R^{28}$ each independently represent hydrogen or $C_{1-4}$alkylcarbonyl;

$Het^1$ represents 2-bora-1,3-dioxolanyl; $Het^2$ represents piperidinyl, piperazinyl, morpholinyl, thiomorpholinyl or 1,1-dioxothiomorpholinyl wherein said $Het^2$ is optionally substituted with $C_{1-4}$alkyloxycarbonyl or $NR^{27}R^{28}$—$C_{1-4}$alkyl;

Ar⁴ and Ar⁵ represents phenyl; Ar⁶ represents phenyl optionally substituted with nitro.

Other special group of compounds are:
those compounds of formula (I) wherein —X¹— represents —O—;
those compounds of formula (I) wherein —X¹— represents C$_{1-2}$alkyl;
those compounds of formula (I) wherein —X¹— represents —NR¹¹—, in particular —NH—;
those compounds of formula (I) wherein —X²— represents —NR¹²—C$_{1-2}$alkyl, in particular —N(CH$_3$)—C$_{1-2}$alkyl-;
those compounds of formula (I) wherein R¹ is fluoro, chloro or bromo;
those compounds of formula (I) wherein R² is fluoro, chloro or bromo;
those compounds of formula (I) wherein R² is Het¹, in particular 2-bora-1,3-dioxolanyl;
those compounds of formula (I) wherein R⁴ is at position 7 of the structure of formula (I).
those compounds of formula (I) wherein R⁴ represents C$_{1-4}$alkyloxy substituted with hydroxy and one substituent selected from NR⁷R⁸ or Het²-;
those compounds of formula (I) wherein R⁷ is hydrogen or methyl and R⁸ represents aminocarbonyl-C$_{1-4}$alkyl-, NR²⁵R²⁶, C$_{1-4}$alkylsulfonyl-C$_{1-4}$alkyl-, C$_{1-4}$alkylcarbonyloxy-C$_{1-4}$alkyl or Het¹¹-C$_{1-4}$alkyl-; in particular those compounds of formula (I) wherein R⁷ is hydrogen or methyl and R⁸ represents aminocarbonyl-C$_{1-4}$alkyl-, NR²⁵R²⁶, C$_{1-4}$alkylsulfonyl-C$_{1-4}$alkyl- or Het¹¹-C$_{1-4}$alkyl-
those compounds of formula (I) wherein Het² represent piperidinyl, 1,1-dioxothiomorpholinyl or piperazinyl and said Het² is optionally substituted with one or where possible two or more substituents selected from NR³⁹R⁴⁰, aminocarbonyl, mono- or di(C$_{1-4}$alkyl)aminocarbonyl or C$_{1-4}$alkylsulfonyl; in particular those compounds of formula (I) wherein Het² represent piperidinyl or piperazinyl and said Het² is optionally substituted with one or where possible two or more substituents selected from NR³⁹R⁴⁰, aminocarbonyl, mono- or di(C$_{1-4}$alkyl)aminocarbonyl or C$_{1-4}$alkylsulfonyl.

In a further embodiment of the present invention the X² substituent is at position 2', the R¹ substituent represents hydrogen or halo and is at position 4', the R² substituent represents halo and is at position 5', the R³ substituent is at position 2 and the R⁴ substituent at position 7 of the structure of formula (I). Alternatively, the X² substituent is at position 3', the R¹ substituent represents hydrogen or halo and is at position 4', the R² substituent represents halo and is at position 5', the R³ substituent is at position 2 and the R⁴ substituent at position 7 of the structure of formula (I).

The compounds of this invention can be prepared by any of several standard synthetic processes commonly used by those skilled in the art of organic chemistry and described for instance in the following references; "Heterocyclic Compounds"—Vol. 24 (part4) p 261-304 Fused pyrimidines, Wiley—Interscience; Chem. Pharm. Bull., Vol 41(2) 362-368 (1993); J. Chem. Soc., Perkin Trans. 1, 2001, 130-137.

As further exemplified in the experimental part of the description, a particular group of compounds are those compounds of formula (I) were —X¹—represents —O— hereinafter referred to as the compounds of formula (3). Said compounds are generally prepared starting from the known 6-acetoxy-4-chloro-7-methoxy quinazoline (II') which can be prepared from commercially available veratric acid and 4-hydroxy-3-methoxy benzoic acid, respectively.

Coupling of the latter with suitable substituted anilines (III') under standard conditions, for example stirred in 2-propanol at an elevated temperature ranging form 40-100° C. during 3-12 h, furnish the intermediate compounds (IV') (Scheme 1).

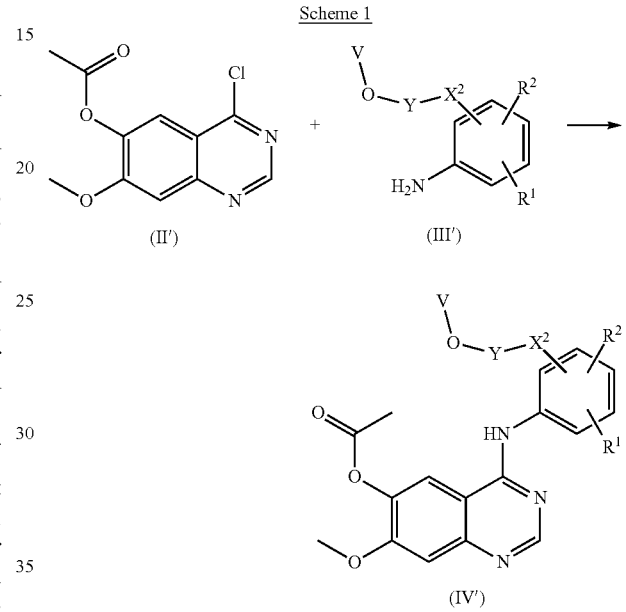

Scheme 1

V = hydrogen or a protective group such as for example, methylcarbonyl, t-butyl, methyl, ethyl, benzyl or trialkylsilyl groups
X², R¹ and R² are defined as for the compounds of formula (I)

Deprotection of the intermediates of formula (IV') as described in Protective Groups in Organic Synthesis by T. W. Greene and P. G. M. Wuts, 3$^{rd}$ edition, 1998 followed by ring closure under Mitsunobu conditions give the macrocyclic compounds (1) that are used as starting compounds in the synthesis of the final compounds of the present invention. (Scheme 2—wherein V is defined as hereinbefore).

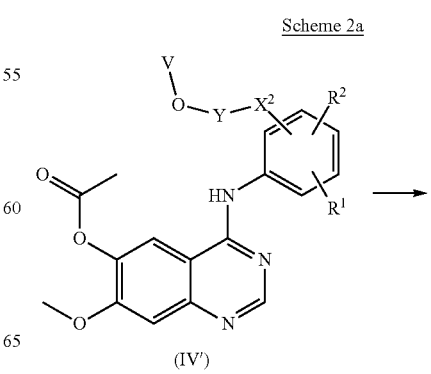

Scheme 2a

-continued

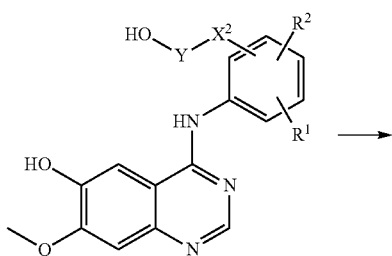

V = hydrogen or a protective group such as for example, methylcarbonyl, t-butyl, methyl, ethyl, benzyl or trialkylsilyl groups
$X^2$, $R^1$ and $R^2$ are defined as for the compounds of formula (I)

In brief, said macrocyclic compounds of formula (1) are demethylated using art known conditions such as for example provided in Schemes 3&4 hereinbelow, followed by an alkylation with an appropriate alcohol, such as for example described in Scheme 5 hereinafter.

Scheme 3:

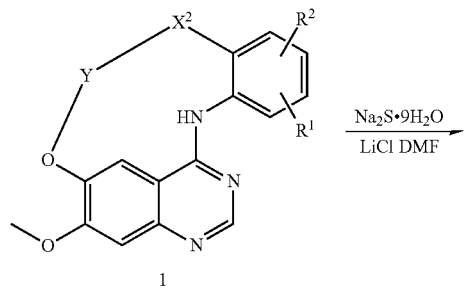

Quinazoline demethylation

A stirred suspension of 1 (1 equiv), LiCl (7 equiv.) and $Na_2S \cdot 9H_2O$ (7 equiv) in DMF, was heated under microwave conditions to 140° C. until completion (30 minutes). The reaction mixture was allowed to cool to ambient temperature and was then poured onto ice water. The mixture was filtered and the yellow precipitation was re-dissolved in DCM/MeOH (9:1) with some HCOOH and purified over silica gel filter (eluens: DCM/MeOH 9.5/0.5). The pure fractions were collected, evaporated and co-evaporated with toluene to give pure 2 (yield: 70%).

Scheme 4:

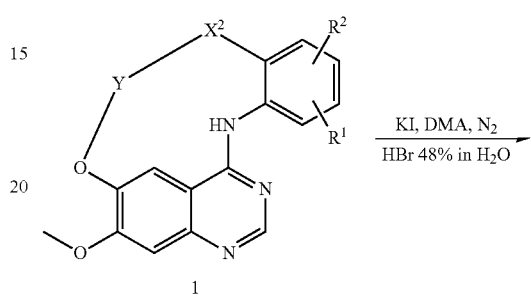

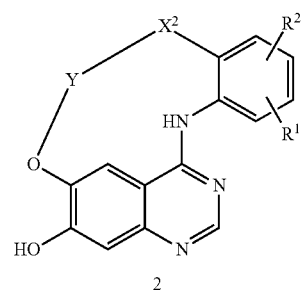

Quinazoline demethylation

To a stirred suspension of 1 (1 equiv) and KI (10 equiv) in DMA, was added HBr (48% in $H_2O$) while bubbling $N_2$ through the reaction mixture. The mixture was rapidly heated to 130° C. and stirred at this temperature until completion (±2 h). The reaction mixture was allowed to cool to 70° C. and poured onto ice/$H_2O$/$NH_3$. The mixture was filtered and the yellow precipitation was re-dissolved in THF/MeOH (2:1), concentrated and co-evaporated with toluene. Crystallization from 2-propanol afford pure 2 (yield: 42-78%).

Scheme 5

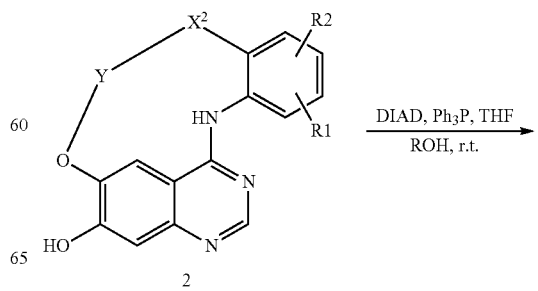

-continued

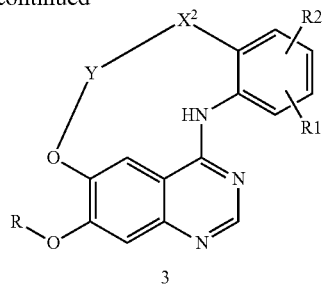

Quinazoline alkylation wherein R represents $Ar^4$—$C_{1-4}$alkyl-, $C_{1-4}$alkyl- or R represents $C_{1-4}$alkyl substituted with one or where possible two or more substituents selected from hydroxy, halo, $C_{1-4}$alkyloxy-, $C_{1-4}$alkyloxy-$C_{1-4}$alkyloxy-, $NR^7R^8$ or $Het^2$—. $Ar^4$, $Het^2$, $R^7$ and $R^8$ are defined as for the compounds of formula (I) hereinbefore.

To a stirred suspension of 2 (1 equiv), alcohol (8 equiv) and triphenylphosphine (2 equiv) in THF, DIAD (2 equiv) was added dropwise and the mixture was stirred at room temperature for 60 min. The reaction mixture was concentrated under reduced pressure, and the crude product was triturated from acetonitrile to afford pure 3.

For those compounds of formula (3) wherein $R^1$ or $R^2$ represent acetylene the following synthesis scheme (Scheme 6) is generally applied. In brief, the halogenated form of the compounds of formula (3) is acetylated using trimethylsilylacetylene followed by deprotection of the acetylene group to yield the compounds of general formula (5).

To a stirred solution of 3 (1 equiv) in pyrrolidine was added bis(triphenylphosphine)palladium(II)chloride (20 mol %) followed by CuI (cat). The reaction mixture was heated to 75° C. and trimethylsilylacetylene (2.5 equiv) was added. The mixture was stirred at this temperature until the reaction was essentially complete and was then filtered through a short pad of celite and concentrated to dryness. The residue was re-dissolved in EtOAc and was partitioned between EtOAc and water. The combined organic layers were concentrated under reduced pressure and the residue was treated with MP-TMT in acetonitrile overnight. It was then filtered, the resin was washed with acetonitrile followed by DCM and the filtrate was concentrated to afford 4.

Compound 4 and aqueous $K_2CO_3$ (sat.) in MeOH (1:1) were stirred at room temperature for 1 hour. The reaction mixture was concentrated under reduced pressure, the residue was re-dissolved in DCM and washed with water. The organic phase was separated, dried ($MgSO_4$) and concentrated under vaccuo. The residue was purified either by column chromatography or reverse phase HPLC to afford pure 5.

A particular group of compounds are those compounds of formula (3) wherein R represents $C_{1-4}$alkyl substituted with $NR^7R^8$ or $Het^2$ wherein said $Het^2$ is attached to the remainder of the molecule through the nitrogen atom. Said compounds of general formula (7) are generally made according to synthesis scheme 7 departing from the intermediate compounds of general formula (2).

Scheme 6

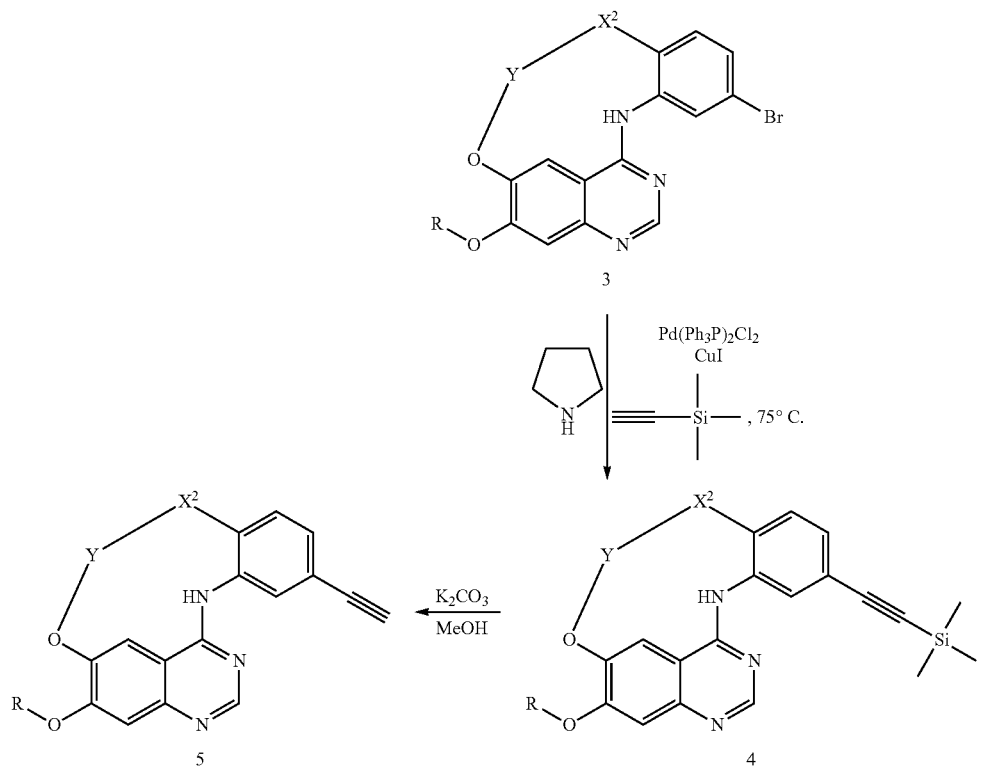

Incorporation of acetylene moiety wherein R is defined as in Scheme 5 hereinbefore

Scheme 7

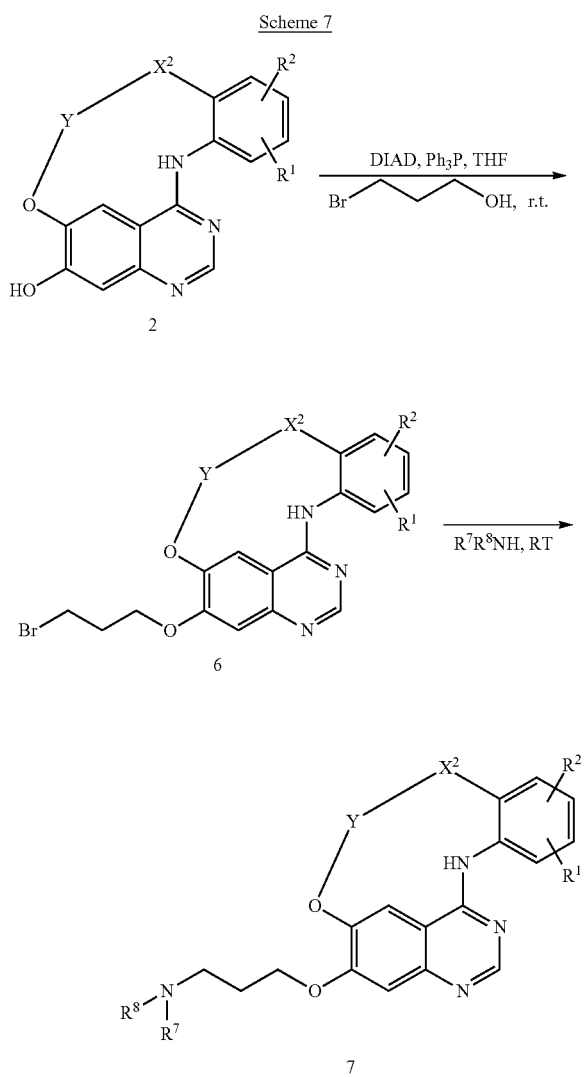

wherein R[7] and R[8] are defined as for the compounds of formula (I), or R[7] and R[8] taken together with the nitrogen atom to which they are attached from a heterocycle wherein said heterocycle is defined as Het[2] for the compounds of formula (I) hereinbefore.

To a stirred suspension of 2 (1 equiv), bromopropyl alcohol (2 equiv) and triphenylphosphine (2 equiv) in THF, DIAD (2 equiv) was added dropwise and the mixture was stirred at room temperature for 60 min. The reaction mixture was concentrated under vaccuo, and the crude product was triturated from acetonitrile to afford pure 6.

To a stirred suspension of 6 (1 equiv), in acetonitrile was added the amine (20 equiv) and the mixture was stirred at room temperature overnight. The reaction mixture was concentrated under vaccuo, and the crude product was triturated from acetonitrile to afford pure 7.

Alternatively to the above, and in particular for those compounds of formula (7) wherein the $C_{1-4}$alkyl moiety is further substituted with hydroxy-, said compounds are made using a nucleophilic addition reaction departing from the oxirane analog 3' (Scheme 8)

Scheme 8

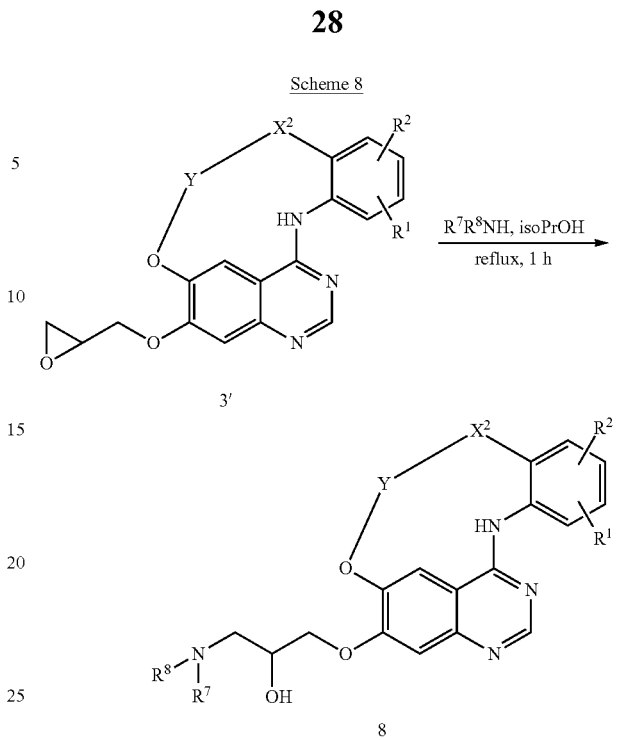

Wherein R[7] and R[8] are defined as for the compounds of formula (I), or R[7] and R[8] taken together with the nitrogen atom to which they are attached from a heterocycle wherein said heterocycle is defined as Het[2] for the compounds of formula (I) hereinbefore.

To a stirred suspension of 3' (1 equiv), in 2-propanol was added the amine (20 equiv) and the mixture was stirred at 70° C. for 2 hours. The reaction mixture was cooled, and the product crystallized from 2-propanol to afford pure 8.

Where necessary or desired, any one or more of the following further steps in any order may be performed:
(i) removing any remaining protecting group(s);
(ii) converting a compound of formula (I) or a protected form thereof into a further compound of formula (I) or a protected form thereof;
(iii) converting a compound of formula (I) or a protected form thereof into a N-oxide, a salt, a quaternary amine or a solvate of a compound of formula (I) or a protected form thereof;
(iv) converting a N-oxide, a salt, a quaternary amine or a solvate of a compound of formula (I) or a protected form thereof into a compound of formula (I) or a protected form thereof;
(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;
(vi) where the compound of formula (I) is obtained as a mixture of (R) and (S) enantiomers resolving the mixture to obtain the desired enantiomer.

Compounds of formula (I), N-oxides, addition salts, quaternary amines and stereochemical isomeric forms thereof can be converted into further compounds according to the invention using procedures known in the art.

It will be appreciated by those skilled in the art that in the processes described above the functional groups of intermediate compounds may need to be blocked by protecting groups.

Functional groups, which are desirable to protect, include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{(1-6)}$alkyl or benzyl esters.

The protection and deprotection of functional groups may take place before or after a reaction step.

Additionally, the N-atoms in compounds of formula (I) can be methylated by art-known methods using $CH_3$—I in a suitable solvent such as, for example 2-propanone, tetrahydrofuran or dimethylformamide.

The compounds of formula (I) can also be converted into each other following art-known procedures of functional group transformation of which some examples are mentioned hereinafter.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydro-carbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as fractional crystallization and chromatographic techniques, e.g. counter-current distribution, liquid chromatography and the like.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as fractional crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, fractional crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures.

As described in the experimental part hereinafter, the growth inhibitory effect and anti-tumour activity of the present compounds has been demonstrated in vitro, in enzymatic assays on the receptor tyrosine kinases such as for example EGFR, Abl, Fyn, FlT1, HcK or the Sar kinase family such as for example Lyn, Yes and cSRC. In an alternative assay, the growth inhibitory effect of the compounds was tested on a number of carcinamo cell lines, in particular in the ovarian carcinoma cell line SKOV3 and the squamous carcinoma cell line A431 using art known cytotoxicity assays such as MTT.

Accordingly, the present invention provides the compounds of formula (I) and their pharmaceutically acceptable N-oxides, addition salts, quaternary amines and stereochemically isomeric forms for use in therapy. More particular in the treatment or prevention of cell proliferation mediated diseases. The compounds of formula (I) and their pharmaceutically acceptable N-oxides, addition salts, quaternary amines and the stereochemically isomeric forms may hereinafter be referred to as compounds according to the invention.

Disorders for which the compounds according to the invention are particularly useful are atherosclerosis, restenosis, cancer and diabetic complications e.g. retinopathy.

In view of the utility of the compounds according to the invention, a method of treating a cell proliferative disorder such as atherosclerosis, restenosis and cancer is provided, the method comprising administering to an animal in need of such treatment, for example, a mammal including humans, suffering from a cell proliferative disorder, a therapeutically effective amount of a compound according to the present invention.

Said method comprising the systemic or topical administration of an effective amount of a compound according to the invention, to animals, including humans. One skilled in the art will recognize that a therapeutically effective amount of the EGFR inhibitors of the present invention is the amount sufficient to induce the growth inhibitory effect and that this amount varies inter alia, depending on the size, the type of the neoplasia, the concentration of the compound in the therapeutic formulation, and the condition of the patient. Generally, an amount of EGFR inhibitor to be administered as a therapeutic agent for treating cell proliferative disorder such as atherosclerosis, restenosis and cancer, will be determined on a case by case by an attending physician.

Generally, a suitable dose is one that results in a concentration of the EGFR inhibitor at the treatment site in the range of 0.5 nM to 200 µM, and more usually 5 nM to 10 µM. To obtain these treatment concentrations, a patient in need of treatment likely will be administered between 0.01 mg/kg to 300 mg/kg body weight, in particular from 10 mg/kg to 100 mg/kg body weight. As noted above, the above amounts may vary on a case-by-case basis. In these methods of treatment the compounds according to the invention are preferably formulated prior to admission. As described herein below, suitable pharmaceutical formulations are prepared by known procedures using well known and readily available ingredients.

Due to their high degree of selectivity as EGFR inhibitors, the compounds of formula (I) as defined above, are also useful to mark or identify the kinase domain within the receptor tyrosine kinase receptors. To this purpose, the compounds of the present invention can be labelled, in particular by replacing, partially or completely, one or more atoms in the molecule by their radioactive isotopes. Examples of interesting labelled compounds are those compounds having at least one halo which is a radioactive isotope of iodine, bromine or fluorine; or those compounds having at least one $^{11}$C-atom or tritium atom.

One particular group consists of those compounds of formula (I) wherein $R^1$ is a radioactive halogen atom. In principle, any compound of formula (I) containing a halogen atom is prone for radiolabelling by replacing the halogen atom by a suitable isotope. Suitable halogen radioisotopes to this purpose are radioactive iodides, e.g. $^{122}$I, $^{123}$I, $^{125}$I, $^{131}$I; radioactive bromides, e.g. $^{75}$Br, $^{76}$Br, $^{77}$Br and $^{82}$Br, and radioactive fluorides, e.g. $^{18}$F. The introduction of a radioactive halogen atom can be performed by a suitable exchange reaction or by using any one of the procedures as described hereinabove to prepare halogen derivatives of formula (I).

Another interesting form of radiolabelling is by substituting a carbon atom by a $^{11}$C-atom or the substitution of a hydrogen atom by a tritium atom.

Hence, said radiolabelled compounds of formula (I) can be used in a process of specifically marking receptor sites in biological material. Said process comprises the steps of (a) radiolabelling a compound of formula (I), (b) administering this radiolabelled compound to biological material and subsequently (c) detecting the emissions from the radiolabelled compound.

Alternatively the compounds are labeled with stable isotopes. In this form of labeling the naturally abundant isotopes of hydrogen, carbon and nitrogen ($^1$H, $^{12}$C and $^{14}$N) are replaced with stable isotopes of these elements ($^2$H [deuterium], $^{13}$C and $^{15}$N, respectively). Labeling with stable isotopes is used for two principal purposes:

Incorporation of stable isotopes into proteins, carbohydrates and nucleic acids facilitates their structural determination at the atomic level.

Metabolic studies exploiting the increased mass of compounds labeled with stable isotopes The term biological material is meant to comprise every kind of material which has a biological origin. More in particular this term refers to tissue samples, plasma or body fluids but also to animals, specially warm-blooded animals, or parts of animals such as organs.

When used in in vivo assays, the radiolabelled compounds are administered in an appropriate composition to an animal and the location of said radiolabelled compounds is detected using imaging techniques, such as, for instance, Single Photon Emission Computerized Tomography (SPECT) or Positron Emission Tomography (PET) and the like. In this manner the distribution to the particular receptor sites throughout the body can be detected and organs containing said receptor sites can be visualized by the imaging techniques mentioned hereinabove. This process of imaging an organ by administering a radiolabelled compound of formula (I) and detecting the emissions from the radioactive compound also constitutes a part of the present invention.

In yet a further aspect, the present invention provides the use of the compounds according to the invention in the manufacture of a medicament for treating any of the aforementioned cell proliferative disorders or indications.

The amount of a compound according to the present invention, also referred to here as the active ingredient, which is required to achieve a therapeutical effect will, of course, vary with the particular compound, the route of administration, the age and condition of the recipient, and the particular disorder or disease being treated. A suitable daily dose would be from 0.01 mg/kg to 300 mg/kg body weight, in particular from 10 mg/kg to 100 mg/kg body weight. A method of treatment may also include administering the active ingredient on a regimen of between one and four intakes per day.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical car-

EXPERIMENTAL PART

Hereinafter, the term 'THF' means tetrahydrofuran, 'DIPE' means diisopropyl ether, 'DMF' means N,N-dimethylformamide, 'NaBH(OAc)$_3$' means sodium triacetoxyborohydride, 'EtOAc' means ethyl acetate, 'EDCI' means N'-(ethylcarbonimidoyl)-N,N-dimethyl-1,3-propanediamine monohydrochloride, 'HOBT' means 1-hydroxy-1H-benzotriazole, 'CDI' means 1,1'-carbonylbis-1H-imidazole, 'DIPEA' means N-ethyl-N-(1-methylethyl)-2-propanamine, 'NaBH$_4$' means sodium tetrahydroborate(−1), 'DMA' means dimethylacetamide, 'DIAD' means bis(1-methylethyl) ester diazenedicarboxylic acid, 'HBTU' means 1-[bis(dimethylamino)methylene]-1H-Benzotriazoliumhexafluorophosphate(1-)3-oxide, 'HATU' means 1-[bis(dimethylamino)methylene]-1H-1,2,3-triazolo[4,5-b]pyridinium 3-oxide, hexafluorophosphate(1-), 'HOAT' means 3-hydroxy-3H-1,2,3-triazolo[4,5-b]pyridine A. Preparation of the Intermediates Example A1 a) Preparation of Intermediate (1)

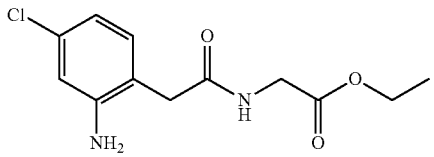 [SMILES: CCOC(=O)CNC(=O)Cc1ccc(Cl)cc1N]

A mixture of N-[[(4-chloro-2-nitrophenyl)acetyl]glycine ethyl ester (0.023 mol) in THF (250 ml) was hydrogenated with Pt/C (2.0 g) as a catalyst in the presence of a 4% thiophene solution in DIPE (1 ml). After uptake of H$_2$ (3 equiv.), the catalyst was filtered off and the filtrate was evaporated. The obtained residue was suspended in DIPE, then the suspension was stirred at boiling temperature, cooled and the desired product was collected by filtration, yielding 6.2 g (100%) of intermediate (1).

b) Preparation of Intermediate (2)

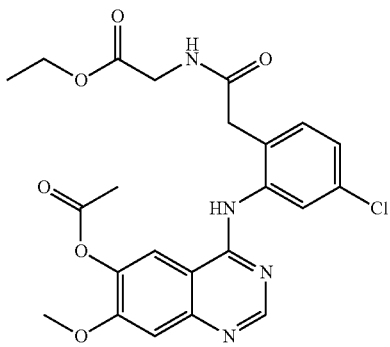 [SMILES: CCOC(=O)CNC(=O)Cc1ccc(Cl)cc1Nc1ncnc2cc(OC)c(OC(C)=O)cc12]

A mixture of 4-chloro-7-methoxy-6-quinazolinol acetate ester (0.00050 mol) and intermediate (1) (0.00050 mol) in 2-propanol (5 ml) was stirred for 16 hours in a pressure tube at 80° C. (oil bath temperature), then the reaction mixture was filtered and the filter residue was air-dried, yielding 0.165 g (67.7%) of intermediate (2).

c) Preparation of Intermediate (3)

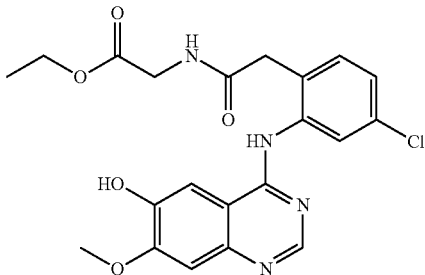 [SMILES: CCOC(=O)CNC(=O)Cc1ccc(Cl)cc1Nc1ncnc2cc(OC)c(O)cc12]

A mixture of intermediate (2) (0.0244 mol) in NH$_3$/CH$_3$OH (7N) (50 ml) and CH$_3$OH (100 ml) was stirred overnight at room temperature and then the solvent was evaporated (Genevac.) under reduced pressure and at room temperature. Finally, the obtained residue was dried (vac.) overnight at 60° C., yielding 8.2 g (75%) of intermediate (3).

d) Preparation of Intermediate (4)

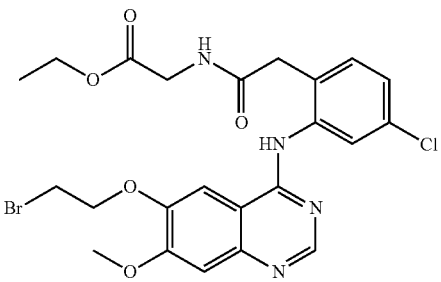 [SMILES: CCOC(=O)CNC(=O)Cc1ccc(Cl)cc1Nc1ncnc2cc(OC)c(OCCBr)cc12]

A mixture of intermediate (3) (0.0138 mol) and Cs$_2$CO$_3$ (0.0690 mol) in DMF (120 ml) was stirred for 30 minutes at room temperature, then 1,2-dibromoethane (0.117 mol) was added and the reaction mixture was stirred overnight at room temperature. The solvent was evaporated under reduced pressure and the residue was co-evaporated with toluene. The obtained residue was stirred in DIPE and the desired product was filtered off, yielding 6.93 g (91%) of intermediate (4).

e) Preparation of Intermediate (5)

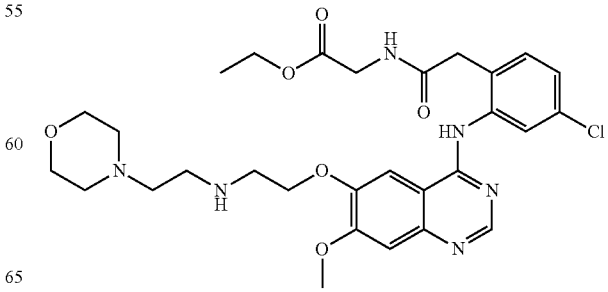

A mixture of intermediate (4) (0.00181 mol) and 4-morpholineethanamine (0.00907 mol) in ethanol (20 ml) was heated in a microwave oven for 90 minutes at 100° C. and then the reaction mixture was purified by reversed-phase high-performance liquid chromatography. The product fractions were collected and the solvent was evaporated, yielding 0.39 g (36%) of intermediate (5).

f) Preparation of Intermediate (6)

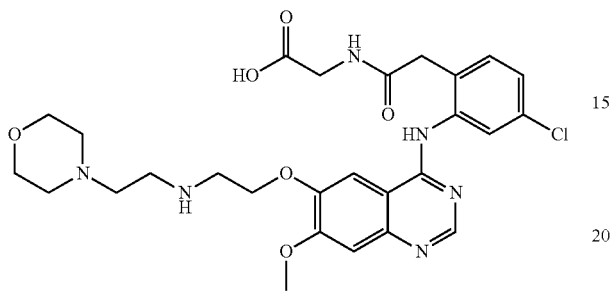

A mixture of intermediate (5) (0.00065 mol) and lithium hydroxide (0.0032 mol) in ethanol (20 ml) and H$_2$O (2 ml) was stirred for 2 hours at room temperature and then the solvent was evaporated under reduced pressure, yielding intermediate (6) (quantitative yield).

Example A2 a) Preparation of Intermediate (7)

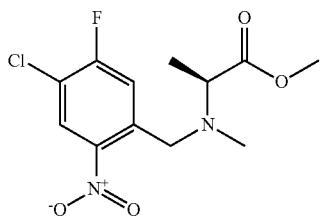

A mixture of 4-chloro-5-fluoro-2-nitrobenzaldehyde (0.0491 mol), N-methyl-L-alanine methyl ester hydrochloride (0.0589 mol) and titanium(4+) 2-propanol salt (0.0737 mol) in 1,2-dichloroethane (100 ml) was stirred at room temperature for 30 minutes. NaBH(OAc)$_3$ (0.0589 mol) was added. The mixture was stirred overnight, then diluted in CH$_2$Cl$_2$, quenched with aqueous (10%) K$_2$CO$_3$ and filtered. The organic layer was separated, dried (MgSO$_4$), filtered, and the solvent was evaporated to dryness, yielding 16.5 g (quantitative yield) of intermediate (7) (S-configuration).

b) Preparation of Intermediate (8)

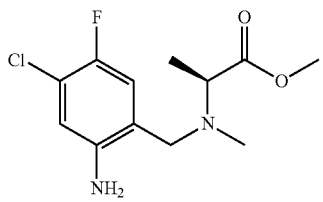 [SMILES: COC(=O)[C@H](C)N(C)Cc1cc(F)c(Cl)cc1N]

A mixture of intermediate (7) (0.0491 mol), Fe (0.246 mol) and NH$_4$Cl (0.491 mol) in THF/CH$_3$OH/H$_2$O (4/4/2; 500 ml) was stirred and refluxed overnight, then cooled to room temperature and filtered. The filtrate was diluted in CH$_2$Cl$_2$. The organic layer was separated, dried (MgSO$_4$), filtered and the solvent was evaporated to dryness, yielding 13 g (96%) of intermediate (8) (S-configuration).

c) Preparation of Intermediate (9)

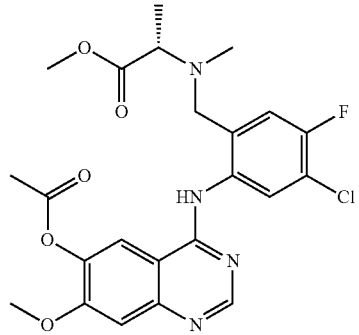 [SMILES: COC(=O)[C@H](C)N(C)Cc1cc(F)c(Cl)cc1Nc1ncnc2cc(OC)c(OC(C)=O)cc12]

A mixture of 4-chloro-7-methoxy-6-quinazolinol acetate ester (0.0162 mol) and intermediate (8) (0.0162 mol) in CH$_3$CN (150 ml) was stirred and refluxed for 4 hours, then cooled back to room temperature, the solvent was evaporated in vacuo and the residue was taken up in K$_2$CO$_3$ (aq.) (10%) and CH$_2$Cl$_2$. The organic layer was separated, dried (MgSO$_4$), filtered, and the solvent was evaporated to dryness. The residue (6.4 g) was purified by column chromatography over silica gel (eluent: CH$_2$Cl$_2$/CH$_3$OH 100/0 to 99/1; 15-40 μm). The desired fractions were collected and the solvent was evaporated, yielding 3.09 g (37%) of intermediate (9) (S-configuration).

d) Preparation of Intermediate (10)

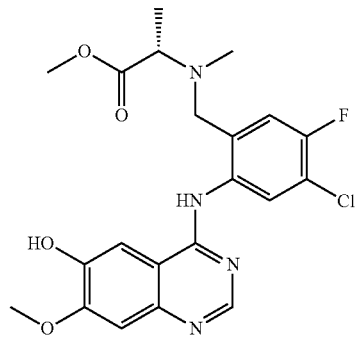 [SMILES: COC(=O)[C@H](C)N(C)Cc1cc(F)c(Cl)cc1Nc1ncnc2cc(OC)c(O)cc12]

A mixture of intermediate (9) (0.0061 mol) in NH$_3$/CH$_3$OH (7N) (20 ml) and CH$_3$OH (100 ml) was stirred at room temperature for 40 hours, then evaporated to dryness. The residue was taken up in CH$_3$CN/DIPE. The precipitate was filtered off and dried, yielding 1.93 g (70%) of intermediate (10) (M.P.: 234° C.; S-configuration).

e) Preparation of Intermediate (11)

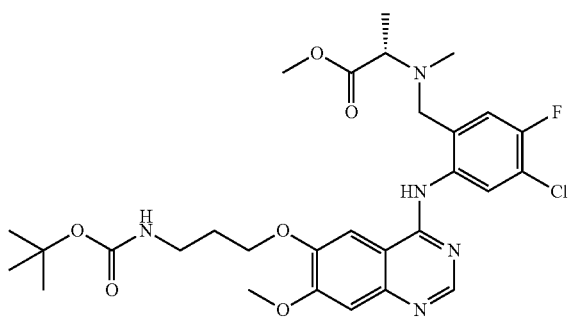 [SMILES: COC(=O)[C@H](C)N(C)Cc1cc(F)c(Cl)cc1Nc1ncnc2cc(OC)c(OCCCNC(=O)OC(C)(C)C)cc12]

Cs$_2$CO$_3$ (0.0063 mol) was added to a solution of intermediate (10) (0.0042 mol) in dry DMF (20 ml). The mixture was stirred at room temperature for 1 hour. A solution of (3-bromopropyl)-1,1-dimethylethyl ester carbamic acid (0.0046 mol) in dry DMF (5 ml) was added. The mixture was stirred at room temperature for 3 hours, poured into H$_2$O and extracted with EtOAc. The organic layer was separated, dried (MgSO$_4$), filtered, and the solvent was evaporated to dryness, yielding: 2.8 g (quantitative yield) of intermediate (11) (S-configuration).

f) Preparation of Intermediate (12)

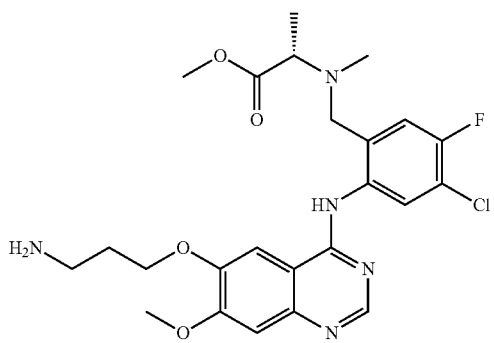 [SMILES: COC(=O)[C@H](C)N(C)Cc1cc(F)c(Cl)cc1Nc1ncnc2cc(OC)c(OCCCN)cc12]

A mixture of intermediate (11) (0.0042 mol) in HCl (aq.) (6N) (20 ml) and dioxane (100 ml) was stirred at 60° C. for 3 hours, then cooled to room temperature and evaporated to dryness. The residue was taken up in ethanol/diethyl ether. The precipitate was filtered under N$_2$ flow and dried in vacuo, yielding 2.24 g (100%) of intermediate (12) as a hydrochloric acid salt (.3.02HCl .1.88H$_2$O; S-configuration; M.P.: 175° C.).

g) Preparation of Intermediate (13)

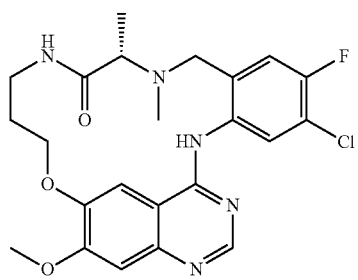 [SMILES: COc1cc2ncnc3c2cc1OCCCNC(=O)[C@H](C)N(C)Cc1cc(F)c(Cl)cc1N3]

Intermediate (12) (0.0018 mol) was added portionwise to a warm solution (50° C.) of EDCI (0.0037 mol), HOBT (0.0037 mol) and triethylamine (0.008 mol) in CH$_2$Cl$_2$/THF (50/50; 1000 ml) over a 3 hour period, under vigorous stirring at 50° C. After evaporation of the solvent, the residue was taken up in K$_2$CO$_3$ (aq.) (10%). The mixture was extracted with CH$_2$Cl$_2$. The organic layer was separated, dried (MgSO$_4$), filtered and the solvent was evaporated to dryness. The residue (1 g) was crystallized from ethanol/DIPE. The precipitate was filtered off and dried. This fraction was crystallized again from CH$_3$CN. The precipitate was filtered off and dried, yielding 0.21 g (24%) of intermediate (13) (M.P.: 270° C.; S-configuration).

h) Preparation of Intermediate (14)

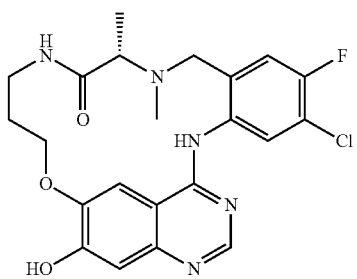 [SMILES: C[C@H]1C(=O)NCCCOc2cc3c(ncnc3cc2O)Nc2cc(Cl)c(F)cc2CN1C]

A mixture of intermediate (13) (0.0001 mol), sodium sulfide (0.001 mol) and lithium chloride (0.0011 mol) in DMF (1 ml) was stirred at room temperature for 5 minutes, then heated in a microwave oven at 90° C. for 15 minutes, poured into saturated NaHCO$_3$ and extracted with diethyl ether three times. The organic layer was washed with saturated NaCl, dried (MgSO$_4$), filtered and the solvent was evaporated to dryness. The residue (1.3 g) was purified by column chromatography over silica gel (eluent: CH$_2$Cl$_2$/CH$_3$OH 100/0 to 90/10; 15-40 µm). The desired fractions were collected and the solvent was evaporated. The residue was crystallized from CH$_3$CN. The precipitate was filtered off and dried, yielding 0.406 g (84%) of intermediate (14) (M.P.: 196° C.; 5-configuration).

i) Preparation of Intermediate (15)

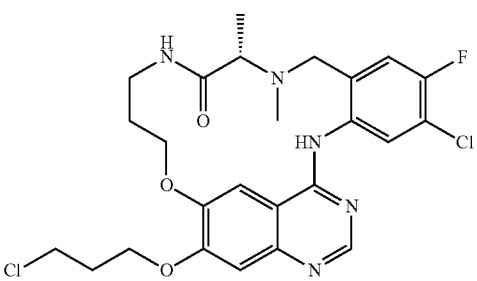 [SMILES: C[C@H]1C(=O)NCCCOc2cc3c(ncnc3cc2OCCCCl)Nc2cc(Cl)c(F)cc2CN1C]

1-Bromo-3-chloropropane (0.0012 mol) was added to a suspension of intermediate (14) (0.0008 mol) and K$_2$CO$_3$ (aq.) (0.0016 mol) in CH$_3$CN/DMF (8 ml). The mixture was stirred and refluxed for 18 hours, then cooled to room temperature, poured into H$_2$O and extracted with EtOAc. The organic layer was separated, dried (MgSO$_4$), filtered and the solvent was evaporated to dryness. The residue (0.85 g) was purified by column chromatography over silica gel (eluent: CH$_2$Cl$_2$/CH$_3$OH 100/0 to 97/3; 15-40 μm). The pure fractions were collected and the solvent was evaporated, yielding 0.24 g (58%) of intermediate (15) (S-configuration).

Example A3 a) Preparation of Intermediate (16)

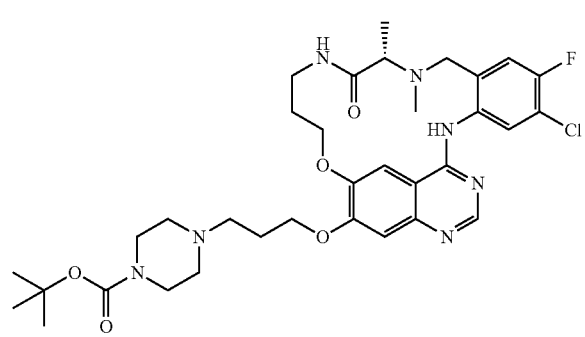 [SMILES: C[C@H]1C(=O)NCCCOc2cc3c(ncnc3cc2OCCCN2CCN(C(=O)OC(C)(C)C)CC2)Nc2cc(Cl)c(F)cc2CN1C]

A mixture of intermediate (15) (0.0005 mol), 1,1-dimethylethyl ester 1-piperazinecarboxylic acid (0.001 mol) and K$_2$CO$_3$ (aq.) (0.0005 mol) in CH$_3$CN (3 ml) was stirred and refluxed overnight. 1,1-Dimethylethyl ester 1-piperazinecarboxylic acid (0.001 mol) and K$_2$CO$_3$ (aq.) (0.0005 mol) were added again. The mixture was stirred and refluxed for 18 hours, cooled to room temperature, poured into H$_2$O and extracted with CH$_2$Cl$_2$. The organic layer was separated, dried (MgSO$_4$), filtered and the solvent was evaporated to dryness. The residue (0.487 g) was purified by column chromatography over kromasil (eluent: CH$_2$Cl$_2$/CH$_3$OH/NH$_4$OH 99/1/0.05 to 90/10/0.5; 5 μm). The pure fractions were collected and the solvent was evaporated, yielding 0.165 g (46%) of intermediate (16) (S-configuration; M.P.: 140° C.).

b) Preparation of Intermediate (17)

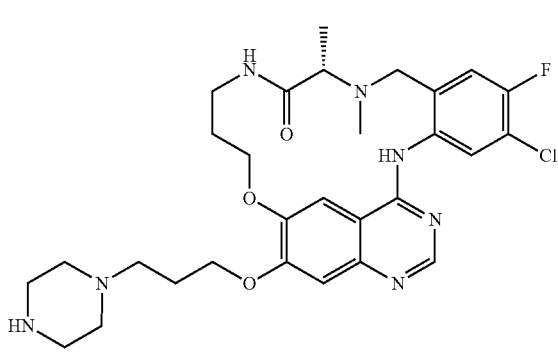 [SMILES: C[C@H]1C(=O)NCCCOc2cc3c(ncnc3cc2OCCCN2CCNCC2)Nc2cc(Cl)c(F)cc2CN1C]

HCl/2-propanol (0.3 ml) was added to a mixture of intermediate (16) (0.0001 mol) in CH$_3$OH (3 ml). The mixture was stirred at room temperature overnight, then stirred at room temperature for 18 extra hours and evaporated to dryness. This hydrochloric acid salt was taken up in K$_2$CO$_3$ (aq.) (10%). The mixture was extracted with CH$_2$Cl$_2$. The organic layer was separated, dried (MgSO$_4$), filtered and the solvent was evaporated to dryness, yielding: 0.095 g (100%) of intermediate (17) (S-configuration).

Example A4 a) Preparation of Intermediate (18)

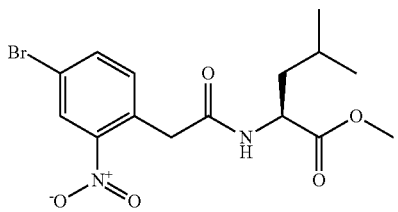

A mixture of 4-bromo-2-nitrobenzeneacetic acid (0.077 mol) and HOBT (0.077 mol) in CH$_2$Cl$_2$ (550 ml) was stirred at room temperature. CDI (0.077 mol) was added and stirring was continued for 10 minutes. Then DIPEA (0.077 mol) was added and the reaction mixture was stirred at room temperature for 30 minutes. L-Leucine methyl ester hydrochloride (0.077 mol) was added at once and the mixture was stirred overnight at room temperature. An extra amount of HOBT (0.077 mol), CDI (0.077 mol) and DIPEA (0.077 mol) was added and the reaction mixture was stirred at room temperature over the weekend. The mixture was quenched with H$_2$O and the layers were separated. The organic layer was washed with saturated K$_2$CO$_3$ (aq.) (1×) and HCl (1N) (1×), then dried (MgSO$_4$), filtered and the solvent was evaporated. The red gum-like product was triturated from 2-propanol. The off-white solid was filtered off and dried, yielding 7.87 g of intermediate (18) (S-configuration).

b) Preparation of Intermediate (19)

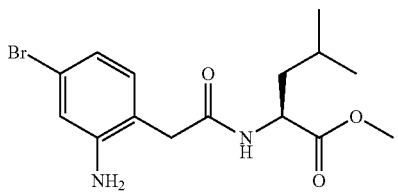

A mixture of intermediate (18) (0.056 mol) in toluene (219 ml) was stirred (mixture (1)). A mixture of NH$_4$Cl (0.283 mol) in H$_2$O (151 ml) was added to mixture (1) and in a next step Fe (0.283 mol) was added. The reaction mixture was refluxed overnight. Then another portion of NH$_4$Cl (0.283 mol) and Fe (0.283 mol) was added and the reaction mixture was refluxed for 1 hour. The mixture was cooled to room temperature and then filtered through dicalite. The layers were separated and the aqueous layer was washed with toluene. The combined organic layers were dried (MgSO$_4$), filtered and the solvent was evaporated, yielding 20.1 g of intermediate (19) (S-configuration).

c) Preparation of Intermediate (20)

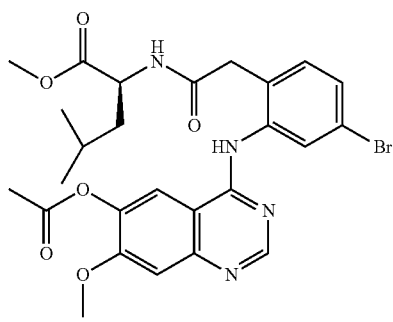 [SMILES: COC(=O)[C@H](CC(C)C)NC(=O)Cc1ccc(Br)cc1Nc1ncnc2cc(OC)c(OC(C)=O)cc12]

A solution of intermediate (19) (0.055 mol) in 2-propanol (200 ml) was heated to 70° C. (solution (1)). A solution of 4-chloro-7-methoxy-6-quinazolinol acetate ester (0.066 mol) in 2-propanol (200 ml) was also heated to 70° C. and this solution was added to solution (1). Stirring at 70° C. was continued for 75 minutes. An extra amount of 4-chloro-7-methoxy-6-quinazolinol acetate ester (0.027 mol) in 2-propanol (100 ml) was added and the mixture was reacted further for 2 hours. The solvent was evaporated and the residue was purified by column chromatography over silica gel (eluent: CH$_2$Cl$_2$/CH$_3$OH 99.5/0.5 till 90/10). The product fractions were collected and the solvent was evaporated, yielding 13.82 g of intermediate (20) (S-configuration).

d) Preparation of Intermediate (21)

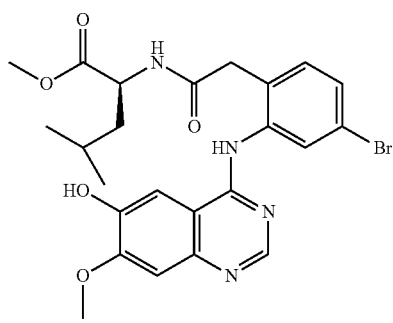 [SMILES: COC(=O)[C@H](CC(C)C)NC(=O)Cc1ccc(Br)cc1Nc1ncnc2cc(OC)c(O)cc12]

A mixture of intermediate (20) (0.081 mol) in CH$_3$OH (400 ml) was stirred at room temperature. NH$_3$/CH$_3$OH (7N) (200 ml) was added and the reaction mixture was stirred at room temperature for 95 minutes. The solvent was evaporated and the residue was triturated from 2-propanol. The pale yellow solid was filtered off and dried, yielding 43 g (99.9%) of intermediate (21) (S-configuration).

e) Preparation of Intermediate (22)

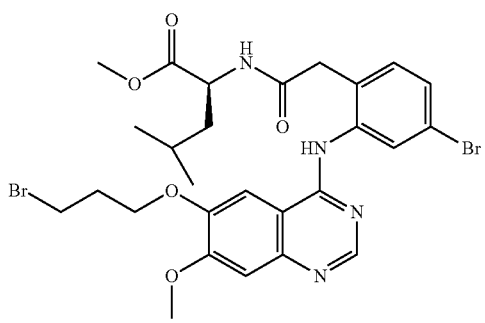 [SMILES: COC(=O)[C@H](CC(C)C)NC(=O)Cc1ccc(Br)cc1Nc1ncnc2cc(OC)c(OCCCBr)cc12]

A mixture of intermediate (21) (0.0113 mol) in DMF (300 ml) was stirred. K$_2$CO$_3$ (aq.) (0.056 mol) was added and the reaction mixture was stirred at room temperature for 35 minutes. Then 1,3-dibromopropane (0.113 mol) was added and the reaction mixture was stirred for 40 hours at room temperature. The reaction mixture was filtered and concentrated under reduced pressure till ~20 ml. The concentrate was poured into H$_2$O and the precipitation was filtered off and dried, yielding 7.16 g (97.1%) of intermediate (22) (S-configuration).

f) Preparation of Intermediate (23)

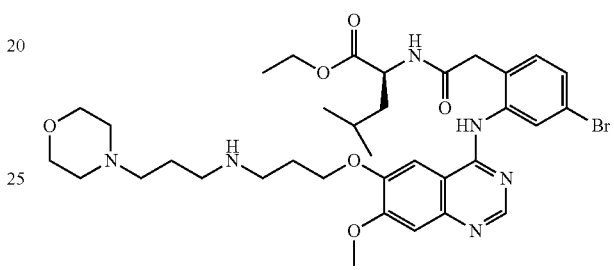

A mixture of intermediate (22) (0.003832 mol) and 4-morpholinepropanamine (0.0383 mol) in ethanol (40 ml) was heated to 100° C. for 1 hour and then purified by high performance liquid chromatography. The organic solvent was evaporated and the water layer was concentrated to ~20 ml. The concentrate was made alkaline with aqueous NaOH (1N) to a pH of ~10 and extracted with EtOAc. The separated organic layer was dried (MgSO$_4$), filtered and the mixture was concentrated, yielding 9.14 g of intermediate (23) (S-configuration).

g) Preparation of Intermediate (24)

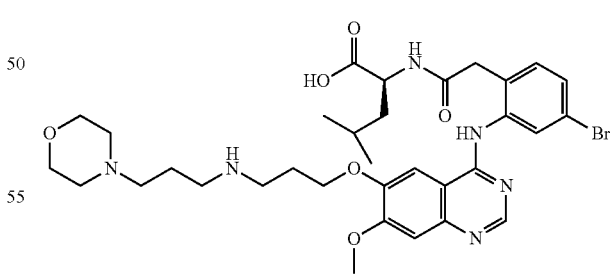

A mixture of intermediate (23) (0.007909 mol) in CH$_3$OH (40 ml) and H$_2$O (4 ml) was stirred at room temperature until dissolution. Lithium hydroxide (0.0395 mol) was added and the reaction mixture was stirred for 85 minutes. The reaction mixture was concentrated and the residue was dried, yielding 5.53 g (99.6%) of intermediate (24) (S-configuration).

h) Preparation of Intermediate (25)

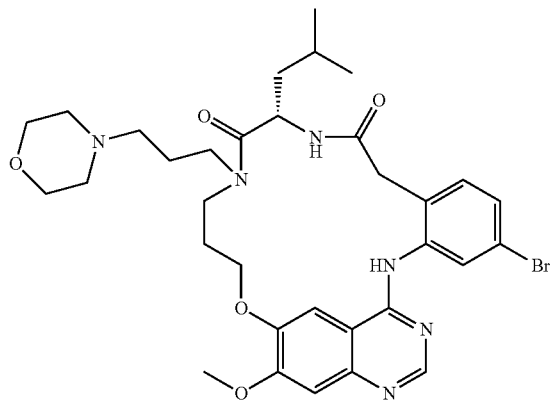 [SMILES: COc1cc2ncnc3c2cc1OCCCN(CCCN1CCOCC1)C(=O)[C@H](CC(C)C)NC(=O)Cc1ccc(Br)cc1N3]

A mixture of HATU (0.002052 mol) and HOAT (0.00008551 mol) in DMA (50 ml) was added dropwise to a mixture of intermediate (24) (0.0007126 mol) and DIPEA (0.002138 mol) in DMA (50 ml). The reaction mixture was stirred overnight. $H_2O$ was added and the mixture was concentrated to ~10 ml. EtOAc was added to the mixture to become a solution. $H_2O$ was added and the two layers were separated. The organic layer was dried ($MgSO_4$), filtered and the solvent was evaporated. The obtained residue was purified by high performance liquid chromatography ($NH_4HCO_3$ buffer). The product fractions were collected, the solvent was evaporated and the residue was dried, yielding intermediate (25) (S-configuration; quantitative yield).

i) Preparation of Intermediate (26)

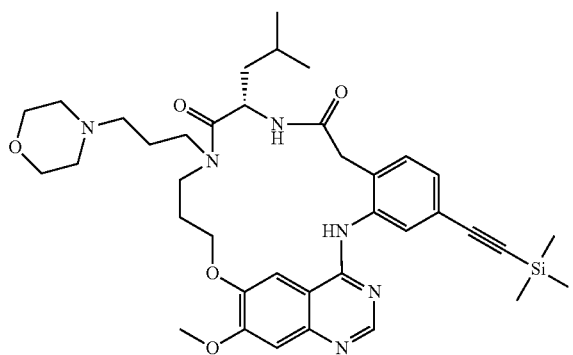 [SMILES: COc1cc2ncnc3c2cc1OCCCN(CCCN1CCOCC1)C(=O)[C@H](CC(C)C)NC(=O)Cc1ccc(C#C[Si](C)(C)C)cc1N3]

A mixture of intermediate (25) (0.0007314 mol) in pyrrolidine (10 ml) was stirred dichlorobis(triphenylphosphine) palladium (0.00003657 mol) and copper iodide (catalytic amount) were added and the reaction mixture was heated to 75° C. Ethynyltrimethylsilane (0.001828 mol) was added and heating was continued for 30 minutes. Then an extra portion of dichlorobis(triphenylphosphine)palladium (0.00003657 mol) and ethynyltrimethylsilane (0.001828 mol) was added and the mixture was reacted for 270 minutes. The reaction mixture was filtered through celite and washed with $CH_3OH$. The solvent was evaporated and the residue was redissolved in EtOAc and washed 2× with $H_2O$. The organic layer was dried ($MgSO_4$), filtered and the solvent was evaporated. The crude residue was redissolved in $CH_3CN$ and MP-TMT resin (0.0003657 mol) was added to scavenge any residual Pd. This mixture was stirred for 36 hours at room temperature and was then filtered. The resin was washed with $CH_3OH$ and the filtrate was evaporated, yielding 0.48 g of intermediate (26) (S-configuration).

Example A5 a) Preparation of Intermediate (27)

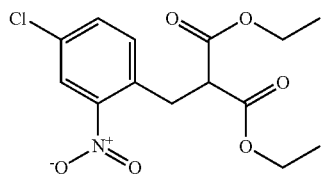

4-Chloro-1-(chloromethyl)-2-nitrobenzene (0.81 mol) and propanedioic acid diethyl ester (0.794 mol) were suspended in hexane (300 ml). $K_2CO_3$ (aq.) (0.81 mol) was added. Then, 18-crown-6 (0.008 mol) was added. The resultant reaction mixture was stirred and refluxed for 30 hours under $N_2$ atmosphere. The reaction mixture was cooled to 20° C. This mixture was extracted with water (750 ml). The layers were separated. The aqueous phase was washed with toluene. The combined organic layers were dried ($Na_2SO_4$), filtered and the solvent was evaporated, yielding 255.8 g of intermediate (27).

b) Preparation of Intermediate (28)

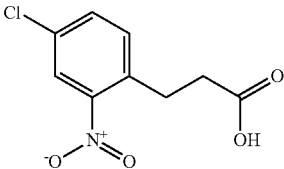

Intermediate (27) (255.8 g, 0.466 mol) was dissolved in acetic acid (1000 ml). A 20% aqueous HCl solution (1000 ml) was added and the resulting reaction mixture was stirred and refluxed for 16 hours. The reaction mixture was cooled to 20° C. and the solvent was evaporated. The residue was suspended in water (500 ml) and treated with a 10% aqueous NaOH solution (500 ml). This mixture was stirred for one hour. This mixture was extracted with diethyl ether (3×500 ml) and then acidified with concentrated HCl resulting in precipitation from the cooled aqueous layer. The precipitate was filtered off and dried, yielding 109 g of intermediate (28) (M.P.: 109-111° C.).

c) Preparation of Intermediate (29)

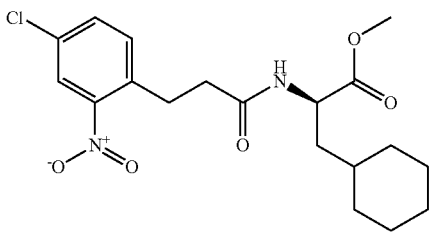

A mixture of intermediate (28) (0.015 mol) and HOBT (0.015 mol) in CH$_2$Cl$_2$ (10 ml) was stirred for 30 minutes at room temperature. CDI (0.015 mol) was added and the reaction mixture was stirred for 30 minutes at room temperature. The resultant solution was added to a mixture of α-aminocyclohexanepropanoic acid methyl ester hydrochloride (0.01875 mol) and diisopropylmethylamine/resin (1 0.05 mol) in CH$_2$Cl$_2$ (70 ml) and the reaction mixture was shaken overnight at room temperature. An excess of scavenger resins (polystyrylmethyl)trimethylammonium bicarbonate and sulfonic acid resin MP (70-90 mesh) were added and the mixture was shaken for 18 hours. The mixture was filtered. The filtrate was concentrated at room temperature, yielding intermediate (29) (S-configuration; quantitative yield).

d) Preparation of Intermediate (30)

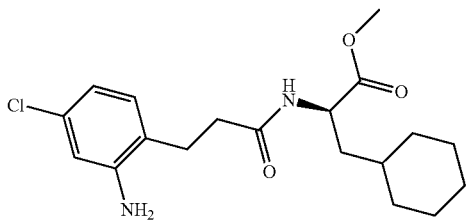 [SMILES: COC(=O)[C@@H](CC1CCCCC1)NC(=O)CCc1ccc(Cl)cc1N]

A mixture of intermediate (29) (0.001 mol) in 2-propanol (20 ml) was hydrogenated with 5% Pt/C (catalytic quantity) as a catalyst in the presence of vanadium oxide (q.s.) and a 4% thiophene solution in DIPE (q.s.). After uptake of H$_2$ (3 equiv), the catalyst was filtered off and the filtrate was evaporated, yielding intermediate (30) (S-configuration; quantitative yield).

e) Preparation of Intermediate (31)

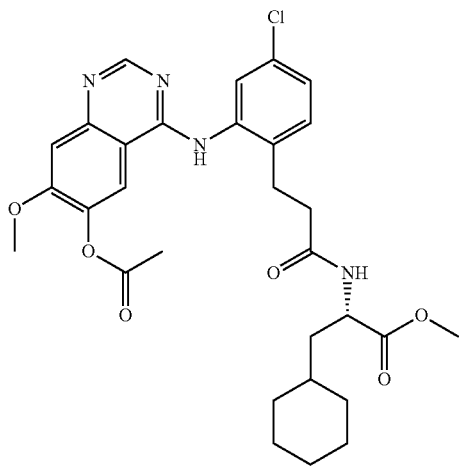 [SMILES: COC(=O)[C@H](CC1CCCCC1)NC(=O)CCc1ccc(Cl)cc1Nc1ncnc2cc(OC)c(OC(C)=O)cc12]

A mixture of 4-chloro-7-methoxy-6-quinazolinol acetate ester (0.001 mol) and intermediate (30) (1 equiv; 0.001 mol) in 2-propanol (25 ml) was stirred for 6 hours at 80° C. The reaction mixture was cooled to room temperature and used as such in next reaction step, yielding intermediate (31) (S-configuration; quantitative yield).

f) Preparation of Intermediate (32)

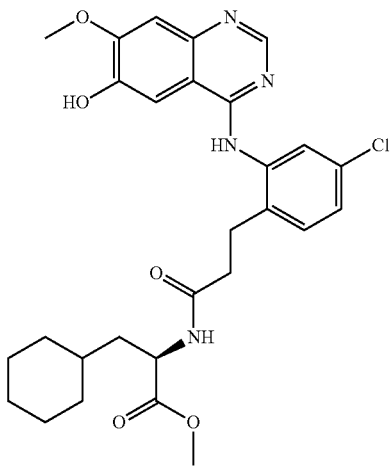 [SMILES: COC(=O)[C@@H](CC1CCCCC1)NC(=O)CCc1ccc(Cl)cc1Nc1ncnc2cc(OC)c(O)cc12]

A mixture of intermediate (31) (0.0010 mol) in 2-propanol (25 ml) and NH$_3$/CH$_3$OH (5 ml) was stirred for 18 hours at room temperature. The solvent was evaporated under reduced pressure. The residue was purified by high-performance liquid chromatography. The product fractions were collected and the solvent was evaporated, yielding intermediate (32) (S-configuration; quantitative yield).

g) Preparation of Intermediate (33)

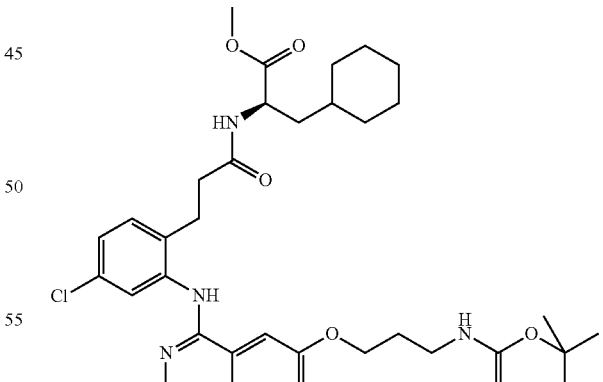

A mixture of intermediate (32) (crude) and Cs$_2$CO$_3$ (5 equiv.) in DMF (5 ml) was stirred for 30 minutes at room temperature. (3-bromopropyl)-1,1-dimethylethyl ester carbamic acid (1.1 equiv.) was added and the reaction mixture was stirred for 18 hours at room temperature. The solvent was evaporated under reduced pressure, yielding intermediate (33) (S-configuration; quantitative yield).

h) Preparation of Intermediate (34)

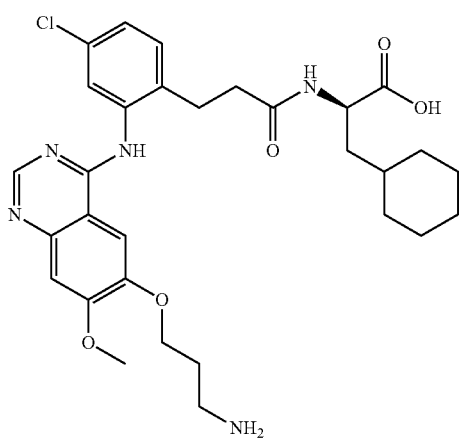 [SMILES: COc1cc2ncnc(Nc3cc(Cl)ccc3CCC(=O)N[C@H](CC3CCCCC3)C(=O)O)c2cc1OCCCN]

A solution of intermediate (33) (crude) in HCl (6N) (2 ml) and dioxane (2 ml) was stirred for 16 hours at 60° C. The solvent was evaporated under reduced pressure, yielding of intermediate (34) (S-configuration; quantitative yield).

Example A6 a) Preparation of Intermediate (35)

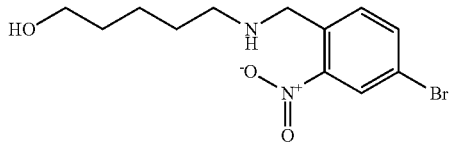

A solution of 4-bromo-2-nitrobenzaldehyde (0.013 mol), 5-amino-1-pentanol (0.013 mol) and titanium(4+) 2-propanol salt (0.014 mol) in ethanol (15 ml) was stirred at room temperature for 1 hour, then the reaction mixture was heated to 50° C. and stirred for 30 minutes. The mixture was cooled to room temperature and NaBH$_4$ (0.013 mol) was added portionwise. The reaction mixture was stirred overnight and then poured onto ice water (50 ml). The resulting mixture was stirred for 20 minutes, the formed precipitate was filtered off (giving Filtrate (I)), washed with H$_2$O and stirred in CH$_2$Cl$_2$ (to dissolve the product and to remove it from the Ti-salt). The mixture was filtered and then the filtrate was dried (MgSO$_4$) and filtered, finally the solvent was evaporated to dryness. Filtrate (I) was evaporated until ethanol was removed and the aqueous concentrate was extracted 2 times with CH$_2$Cl$_2$. The organic layer was separated, dried (MgSO$_4$), filtered off and the solvent was evaporated dry, yielding 3.8 g (93%) of intermediate (35).

b) Preparation of Intermediate (36)

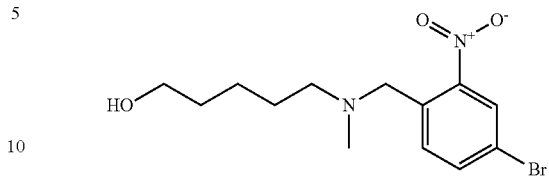

A solution of intermediate (35) (0.0047 mol), formaldehyde (0.025 mol) and titanium(4+) 2-propanol salt (0.0051 mol) in ethanol (150 ml) was heated to 50° C. and stirred for 1 hour, then NaBH$_4$ (0.026 mol) was added portionwise at room temperature. The reaction mixture was stirred overnight and then quenched with water (100 ml). The resulting mixture was stirred for 1 hour; the formed precipitate was filtered off and washed. The organic filtrate was concentrated, then the aqueous concentrate was extracted with CH$_2$Cl$_2$ and dried. The solvent was evaporated dry and the residue was filtered over silica gel (eluent: CH$_2$Cl$_2$/CH$_3$OH from 98/2 to 95/5). The product fractions were collected and the solvent was evaporated dry, yielding 0.5 g of intermediate (36).

c) Preparation of Intermediate (37)

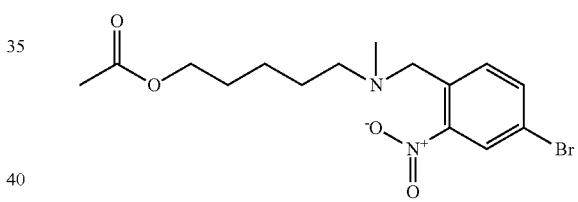

A solution of intermediate (36) (0.0015 mol) and pyridine (0.015 mol) in acetic acid anhydride (8 ml) was stirred overnight at room temperature, then the solvent was evaporated and co-evaporated with toluene, yielding intermediate (37) (quantitative yield).

d) Preparation of Intermediate (38)

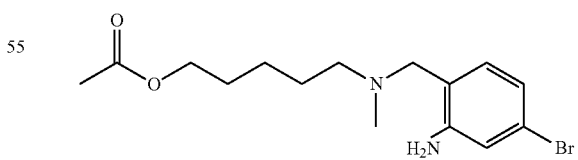

A mixture of intermediate (37) (0.0015 mol) in THF (50 ml) was hydrogenated with 5% Pt/C (0.5 g) as a catalyst in the presence of a 4% thiophene solution in DIPE (0.5 ml). After uptake of H$_2$ (3 equiv.), the catalyst was filtered off and the filtrate was evaporated, yielding 0.5 g of intermediate (38).

e) Preparation of Intermediate (39)

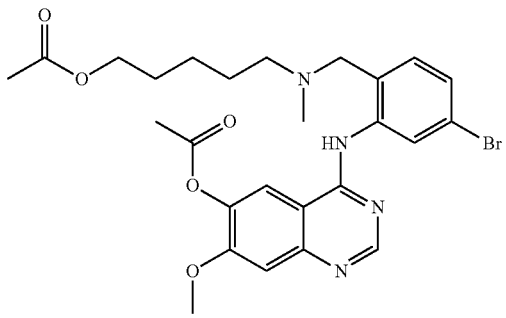 [SMILES: COc1cc2ncnc(Nc3cc(Br)ccc3CN(C)CCCCCOC(C)=O)c2cc1OC(C)=O]

A mixture of intermediate (38) (0.0015 mol) and 4-chloro-7-methoxy-6-quinazolinol acetate ester (0.0015 mol) in 2-propanol (30 ml) was heated to 80° C. and the reaction mixture was stirred for 1 day. The solvent was evaporated under reduced pressure, yielding 0.83 g of intermediate (39).

f) Preparation of Intermediate (40)

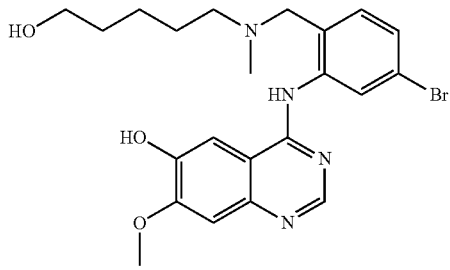 [SMILES: COc1cc2ncnc(Nc3cc(Br)ccc3CN(C)CCCCCO)c2cc1O]

A solution of intermediate (39) (0.0015 mol) in $CH_3OH$ (25 ml) was stirred at room temperature and a solution of $K_2CO_3$ (0.003 mol) in $H_2O$ (2.5 ml) was added, then the reaction mixture was heated to 60° C. and stirred for 18 hours. The solvent was evaporated and $H_2O$ (20 ml) was added, then the mixture was neutralised with acetic acid and the formed precipitate was filtered off. The filtrate was concentrated under reduced pressure and the concentrate was extracted with $CH_2Cl_2$, filtered, then dried ($MgSO_4$) and the mixture was concentrated under reduced pressure, yielding 0.5 g (70%) of intermediate (40).

g) Preparation of Intermediate (41)

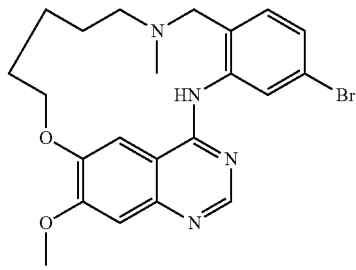 [SMILES: COc1cc2ncnc3c2cc1OCCCCCN(C)Cc1ccc(Br)cc1N3]

A solution of intermediate (40) (0.0011 mol) in THF (50 ml) was stirred at room temperature and tributylphosphine (0.0016 mol) was added, then 1,1'-(azodicarbonyl)bispiperidine (0.0016 mol) was added and the reaction mixture was stirred for 2 hours. The solvent was evaporated until ⅓ of the initial volume. The resulting precipitate was filtered off and washed. The filtrate was evaporated and the residue was purified by high-performance liquid chromatography. The product fractions were collected and the organic solvent was evaporated. The aqueous concentrate was extracted 2 times with $CH_2Cl_2$ and the organic layer was dried ($MgSO_4$). The solvent was evaporated dry and the residue was dried (vacuum) at 50° C., yielding 0.004 g (0.8%) of intermediate (41).

h) Preparation of Intermediate (42)

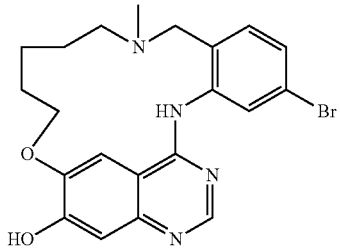 [SMILES: CN1CCCCCOc2cc3c(ncnc3cc2O)Nc2cc(Br)ccc2C1]

A 48% solution of hydrobromide in water (5.5 ml) was added to a suspension of intermediate (41) (0.0058 mol) and potassium iodide (0.044 mol) in DMA (55 ml), stirred at room temperature under $N_2$ flow. The reaction mixture was stirred for 2.5 hours at 130° C. The reaction mixture was poured onto ice water. The layers were separated. The aqueous layer was neutralised with NaOH (1N) and the resulting precipitate was filtered off, then dissolved in $CH_2Cl_2$, washed with water, separated and the organic phase was dried, filtered and the solvent evaporated under reduced pressure. The residue was stirred in water, filtered off, dissolved in THF and the solvent was evaporated (toluene was added and azeotroped on the rotary evaporator), yielding 1.58 g (61%) of intermediate (42).

i) Preparation of Intermediate (43)

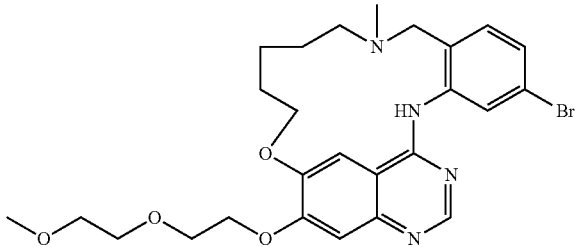 [SMILES: COCCOCCOc1cc2ncnc3c2cc1OCCCCCN(C)Cc1ccc(Br)cc1N3]

Bis(1-methylethyl) ester diazenedicarboxylic acid (0.0158 mol) was added dropwise to a suspension of intermediate (42) (0.007895 mol), 2-(2-methoxyethoxy)ethanol (0.0631 mol) and triphenylphosphine (0.0158 mol) in THF (120 ml), stirred at room temperature. The reaction mixture was stirred at room temperature for 20 minutes. The solvent was evaporated in vacuo. The residue was stirred for 10 minutes in CH₃CN at room temperature. The precipitate was filtered off, washed with CH₃CN and dried, yielding 3.37 g (78%) of intermediate (43).

j) Preparation of Intermediate (44)

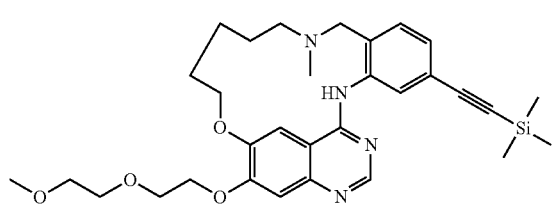

Intermediate (43) (0.0009166 mol) was stirred in pyrrolidine (10 ml). Dichlorobis(triphenylphosphine)palladium (0.00004583 mol) was added, followed by addition of copper iodide (catalytic quantity). The mixture was heated to 70° C. Ethynyltrimethylsilane (0.002292 mol) was added and the reaction mixture was stirred at 70° C. for 4.75 hours. The reaction mixture was cooled to room temperature, filtered through dicalite and the filter residue was washed with CH₃OH. The filtrate was concentrated. The concentrate was redissolved in EtOAc, then partitioned between water and EtOAc. The organic layer was separated, dried (MgSO₄), filtered and the solvent was evaporated. The residue was redissolved in CH₃CN and treated with MP-TMT resin (0.002292 mol) to scavenge any residual Pd. The mixture was stirred slowly over the weekend. The mixture was filtered. The resin was washed with CH₃OH and the filtrate's solvent was evaporated, yielding 0.400 g of intermediate (44).

Example A7 a) Preparation of Intermediate (45)

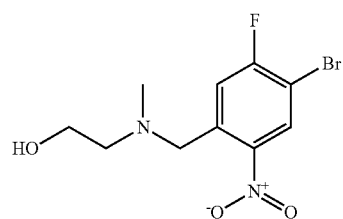

A solution of 2-(methylamino)ethanol (0.077 mol) in CH₂Cl₂ (180 ml) was stirred at room temperature. Tetrakis (2-methyl-2-propanolato)titanate(1-) (0.077 mol) was added, followed by triethylamine (0.077 mol). 4-Bromo-5-fluoro-2-nitrobenzaldehyde (0.077 mol) was added and the mixture was stirred for 90 minutes. NaBH(OAc)₃ (0.0847 mol) was added and the reaction mixture was stirred for 18 hours at room temperature. The mixture was poured into an aqueous NaHCO₃ solution. The precipitate was filtered off. The layers were separated. The organic phase was washed with water (2×), dried (MgSO₄), filtered and the solvent was evaporated. The residue was purified by column chromatography over silica gel (eluent: CH₂Cl₂/CH₃OH 99/1 to 99/2). The desired fractions were collected and the solvent was evaporated, yielding 18 g of intermediate (45).

b) Preparation of Intermediate (46)

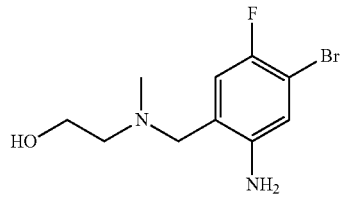

A mixture of intermediate (45) (0.059 mol) in EtOAc (250 ml) was hydrogenated at room temperature and atmospheric pressure with 5% Pt/C (2 g) as a catalyst in the presence of vanadium oxide (0.5 g) and a 4% thiophene solution in DIPE (2 ml). After uptake of H₂ (3 equiv), the catalyst was filtered off and the filtrate was evaporated, yielding intermediate (46) (quantitative yield).

c) Preparation of Intermediate (47)

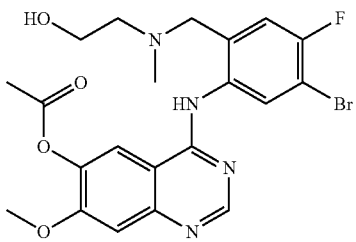 [SMILES: COc1cc2ncnc(Nc3cc(Br)c(F)cc3CN(C)CCO)c2cc1OC(C)=O]

A mixture of intermediate (46) (0.0396 mol) and 4-chloro-7-methoxy-6-quinazolinol acetate ester (0.0396 mol) in 2-propanol (300 ml) was stirred for 1 day at 75° C. More 4-chloro-7-methoxy-6-quinazolinol acetate ester (5 g) was added and the reaction mixture was stirred again for 1 day at 75° C. The solvent was evaporated under reduced pressure, yielding intermediate (47) (quantitative yield).

d) Preparation of Intermediate (48)

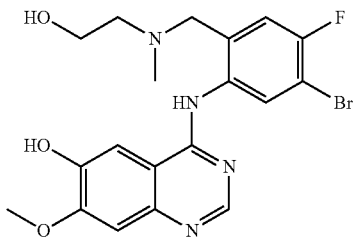 [SMILES: COc1cc2ncnc(Nc3cc(Br)c(F)cc3CN(C)CCO)c2cc1O]

A mixture of intermediate (47) (0.0396 mol) in NH₃/CH₃OH (200 ml) and CH₃OH (100 ml) was stirred overnight at room temperature. The resulting precipitate was filtered off, washed and dried (vacuum, 60° C.), yielding 15.7 g of intermediate (48).

e) Preparation of Intermediate (49)

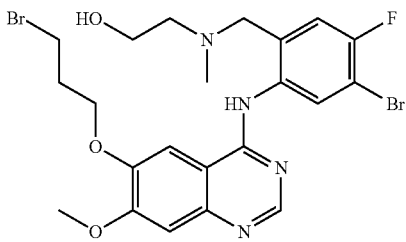 [SMILES: COc1cc2ncnc(Nc3cc(Br)c(F)cc3CN(C)CCO)c2cc1OCCCBr]

A solution of intermediate (48) (0.0347 mol) in DMF (150 ml) was stirred at room temperature and treated with $K_2CO_3$ (aq.) (0.16 mol). The reaction mixture was stirred for 45 minutes at room temperature. 1,3-Dibromopropane (0.31 mol) was added and the reaction mixture was stirred for 2 hours at room temperature. The mixture was poured onto ice/water, stirred for 10 minutes, and the resulting precipitate was filtered off, washed and dried (vacuum, 60° C.). The solid was stirred in DIPE, filtered off, washed, then dried again in vacuo at 60° C., yielding 19.2 g (97%) of intermediate (49).

f) Preparation of Intermediate (50)

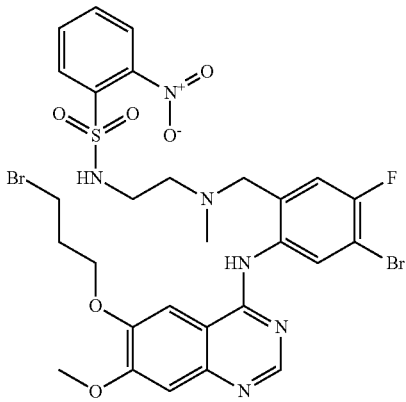 [SMILES: COc1cc2ncnc(Nc3cc(Br)c(F)cc3CN(C)CCNS(=O)(=O)c3ccccc3[N+](=O)[O-])c2cc1OCCCBr]

A solution of intermediate (49) (0.033 mol), 2-nitrobenzenesulfonamide (0.10 mol) and triphenylphosphine (0.0495 mol) in THF (700 ml) was stirred at room temperature. A solution of bis(1-methylethyl) ester diazenedicarboxylic acid (0.0495 mol) in THF (50 ml) was added dropwise and the reaction mixture was stirred overnight. The solvent was evaporated under reduced pressure. The residue was purified by column chromatography over silica gel. The product fractions were collected and the solvent was evaporated, yielding intermediate (50) (quantitative yield).

Example A8 a) Preparation of Intermediate (51)

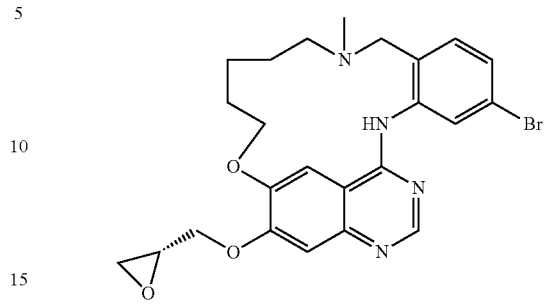

DIAD (0.005 mol) was added dropwise to a mixture of intermediate (42) (0.0017 mol), (2R)-xiranemethanol (0.0105 mol) and triphenylphosphine (0.005 mol) in THF (30 ml), stirred at room temperature for 5 hours. The precipitate was filtered off, washed with THF, and dried, yielding 0.545 g (64%) of intermediate (51) (R-configuration).

Example A9 a) Preparation of Intermediate (52)

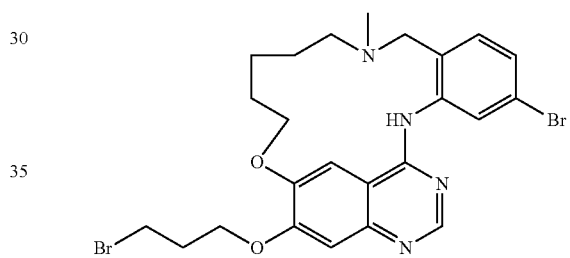

DIAD (0.0003 mol) was added dropwise to a solution of intermediate (42) (0.000138 mol), 3-bromo-1-propanol (0.00055 mol) and triphenylphosphine (0.0003 mol) in THF (2 ml), stirred at room temperature. The reaction mixture was stirred for 1 hour at room temperature. The solvent was evaporated under a gentle flow of $N_2$, yielding intermediate (52) (quantitative yield).

B. Preparation of the Compounds

Example B1

Preparation of Compound (1)

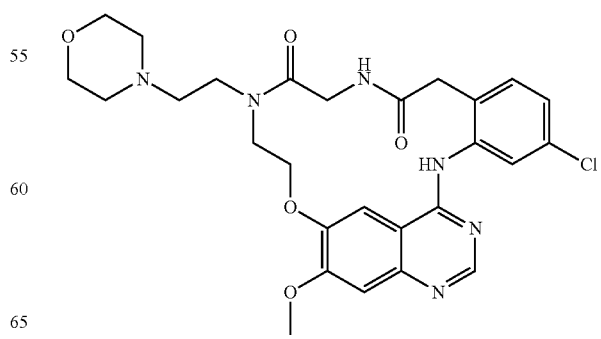

HBTU (0.00195 mol) was added to a stirred solution of intermediate (6) (0.00069 mol) and DIPEA (0.00324 mol) in N,N-dimethylacetamide (250 ml) at room temperature, then the reaction mixture was stirred for 3 hours and the solvent was co-evaporated with toluene under reduced pressure. The obtained residue was purified by reversed-phase high-performance liquid chromatography (eluent 1: NH₄OAc; eluent 2: NH₄HCO₃). The pure product fractions were collected and the solvent was evaporated under reduced pressure. The obtained residue (0.030 g) was crystallised from 2-propanol, then the resulting precipitate was filtered off and dried (vacuum), yielding 0.0165 g of compound (1).

Example B2

Preparation of Compound (2) and Compound (3)

compound (2)

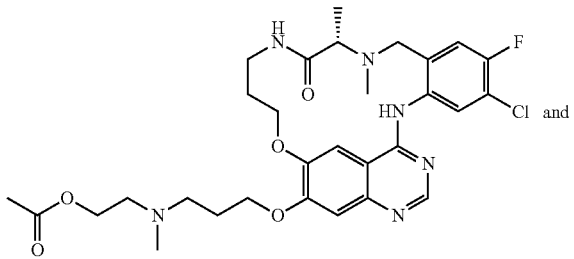

and compound (3)

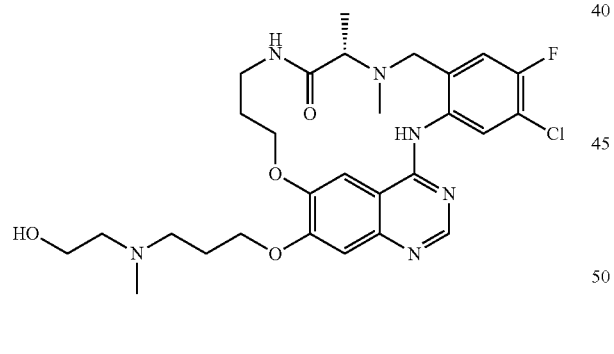

A mixture of intermediate (15) (0.0002 mol), 2-(methylamino)ethanol (0.0005 mol) and K₂CO₃ (aq.) (0.0002 mol) in CH₃CN (1.5 ml) was stirred and refluxed overnight, then cooled to room temperature, poured into H₂O and extracted with CH₂Cl₂. The organic layer was separated, dried (MgSO₄), filtered and the solvent was evaporated to dryness. The residue (0.16 g) was purified by column chromatography over kromasil (eluent: CH₂Cl₂/CH₃OH/NH₄OH 99/1/0.05 to 88/12/1.2; 5 μm). Two fractions were collected and the solvent was evaporated, yielding 0.009 g (6%) of compound (3) (S-configuration) and 0.05 g (31%) of compound (2) (S-configuration).

Example B3

Preparation of Compound (4)

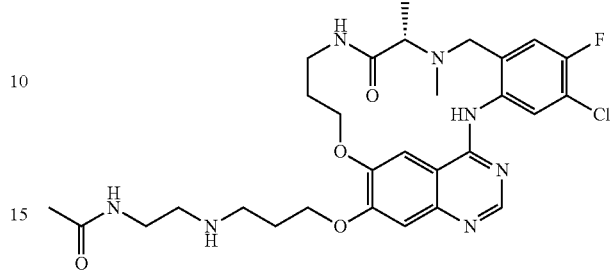

A mixture of intermediate (15) (0.0002 mol), N-(2-aminoethyl)acetamide (0.0005 mol) and K₂CO₃ (aq.) (0.0002 mol) in CH₃CN (1.5 ml) was stirred and refluxed overnight. N-(2-aminoethyl)acetamide and K₂CO₃ (aq.) were added again. The mixture was stirred and refluxed for 5 hours, then cooled to room temperature, poured into H₂O and extracted with CH₂Cl₂. The organic layer was separated, dried (MgSO₄), filtered and the solvent was evaporated to dryness. The residue (0.146 g) was purified by column chromatography over kromasil (eluent: CH₂Cl₂/CH₃OH/NH₄OH 99/1/0.05 to 75/25/1; 5 μm). The pure fractions were collected and the solvent was evaporated. The residue (0.042 g, 27%) was crystallized from diethyl ether. The precipitate was filtered off and dried, yielding 0.034 g (22%) of compound (4) (S-configuration; M.P.: 112° C.).

Example B4

Preparation of Compound (5)

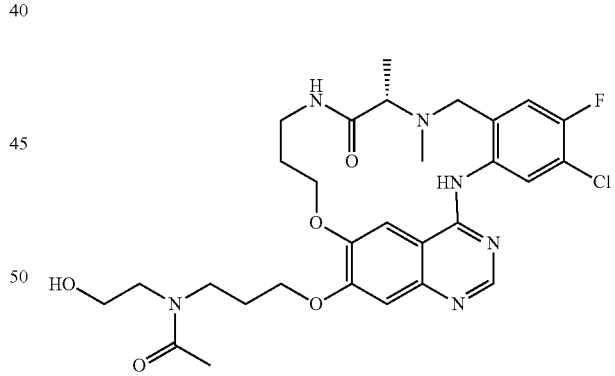

A mixture of intermediate (15) (0.0002 mol), ethanolamine (0.0005 mol) and K₂CO₃ (aq.) (0.0002 mol) in CH₃CN (1.5 ml) was stirred and refluxed overnight. CH₃OH was added. The mixture was stirred at room temperature for 18 hours, poured into H₂O and extracted with EtOAc. The organic layer was separated, dried (MgSO₄), filtered and the solvent was evaporated to dryness. The residue (0.12 g) was purified by column chromatography over kromasil (eluent: CH₂Cl₂/CH₃OH/NH₄OH 96/4/0.4 to 86/4/1.4; 5 μm). The pure fractions were collected and the solvent was evaporated, yielding 0.048 g (33%) of compound (5) (S-configuration).

Example B5

Preparation of Compound (6)

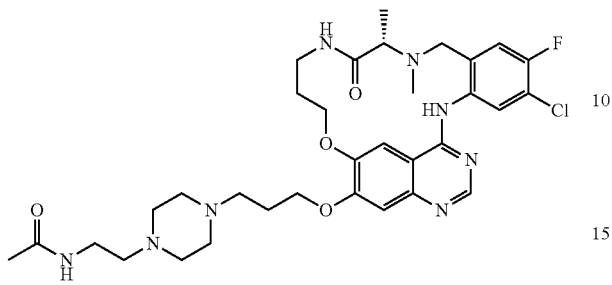

A mixture of intermediate (17) (0.0001 mol), N-(2-chloroethyl)acetamide (0.0001 mol), K$_2$CO$_3$ (aq.) (0.0003 mol) and potassium iodide (0.004 g) in ethanol (3 ml) was stirred and refluxed for 3 days, then cooled to room temperature, poured into H$_2$O and extracted with CH$_2$Cl$_2$. The organic layer was separated, dried (MgSO$_4$), filtered and the solvent was evaporated to dryness. The residue (0.097 g) was purified by column chromatography over kromasil (eluent: CH$_2$Cl$_2$/CH$_3$OH/NH$_4$OH 96/4/0.5 to 90/10/0.5; 5 μm). The pure fractions were collected and the solvent was evaporated. The residue (0.042 g, 42%) was crystallized from CH$_3$CN. The precipitate was filtered off and dried, yielding 0.032 g (32%) of compound (6) (S-configuration; M.P.: 136° C.).

Example B6

Preparation of Compound (7)

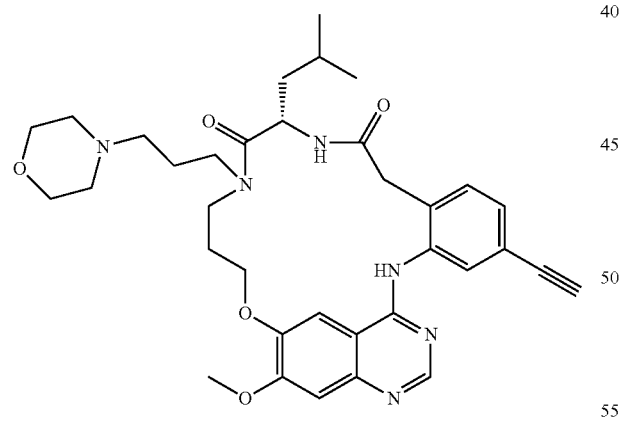

A mixture of intermediate (26) (0.0006848 mol) in a saturated aqueous K$_2$CO$_3$ solution (60 ml) and CH$_3$OH (60 ml) was stirred for 30 minutes at room temperature. The solvent was evaporated and the residue was dissolved in CH$_2$Cl$_2$/H$_2$O. The layers were separated and the organic layer was dried (MgSO$_4$), filtered and the solvent was evaporated. The crude residue was purified by flash column chromatography over silica gel (eluent: CH$_2$Cl$_2$/CH$_3$OH 99/1 till 95/5; column was stripped with CH$_2$Cl$_2$/(CH$_3$OH/NH$_3$) 95/5). The desired fractions were purified again by column chromatography over silica gel (eluent: CH$_2$Cl$_2$/(CH$_3$OH/NH$_3$) 100/0 to 97/3). The product fractions were collected and the solvent was evaporated. The residue was purified by high-performance liquid chromatography (ammonium acetate buffer). The product fractions were collected, the CH$_3$CN was evaporated and the aqueous layer was made alkaline (pH=10). The product was extracted with CH$_2$Cl$_2$. The separated organic layer was dried and the solvent was evaporated, yielding 0.419 g of compound (7) (S-configuration).

Example B7

Preparation of Compound (8)

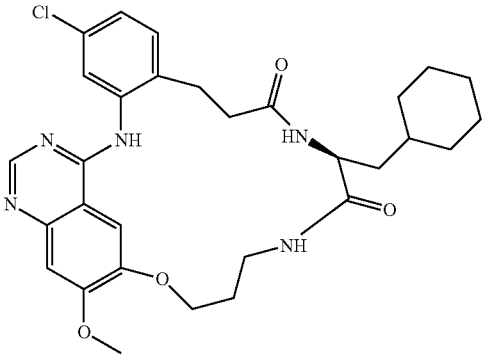 [SMILES: COc1cc2ncnc3c2cc1OCCCNC(=O)[C@H](CC1CCCCC1)NC(=O)CCc1ccc(Cl)cc1N3]

A solution of HBTU (excess) and DIPEA (3 equiv) in DMF (3 ml) was stirred at room temperature. A solution of intermediate (34) (crude) in DMF (2 ml) was added dropwise (Zymark). The resultant reaction mixture was stirred overnight at room temperature. The solvent was evaporated. The residue was purified by high-performance liquid chromatography. The product fractions were collected and the solvent was evaporated, yielding 0.016 g of compound (8) (S-configuration).

Example B8

Preparation of Compound (9)

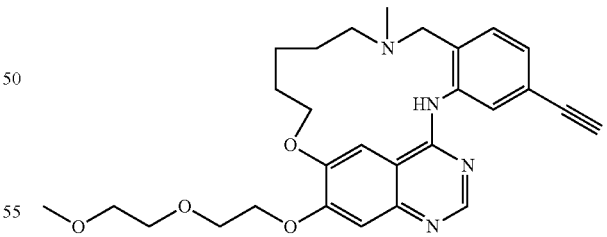

Lithium hydroxide (0.340 g, 0.0081 mol) was added to a mixture of intermediate (44) (0.0006 mol) in CH$_3$OH (25 ml) and H$_2$O (5 ml), stirred at room temperature. The reaction mixture was stirred for one hour at 40° C. The mixture was concentrated under reduced pressure to one fifth of the initial volume. The concentrate was poured into water. The mixture was stirred for 30 minutes at room temperature. The precipitate was filtered off, stirred in THF (20 ml) for one hour, then the precipitate was filtered off again. The solid was dissolved in THF/CH$_3$OH 1/1 (200 ml).

The whole was filtered and the filtrate was evaporated under reduced pressure. The residue was dried, then stirred for one hour in CH₃CN. The precipitate was filtered off and dried, yielding 0.142 g (48%) of compound (9).

Example B9

Preparation of Compound (10)

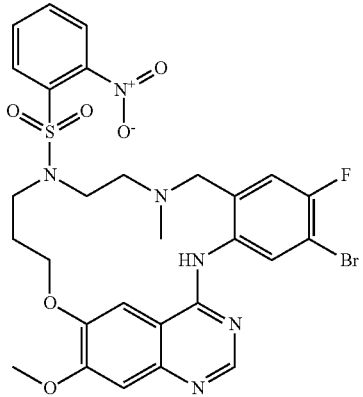 [SMILES: COc1cc2ncnc3c2cc1OCCCN(S(=O)(=O)c1ccccc1[N+](=O)[O-])CCN(C)Cc1cc(F)c(Br)cc1N3]

To a stirred mixture of Cs₂CO₃ (0.018 mol), CH₃CN (100 ml) and N,N,N-tributyl-1-butanaminium iodide (0.0072 mol) was added a solution of intermediate (50) (0.0036 mol) in CH₃CN (300 ml) at 60° C. The reaction mixture was stirred for 4 hours at 60° C. The solvent was evaporated under reduced pressure. The residue was purified by high-performance liquid chromatography. The product fractions were collected and the solvent was evaporated, yielding 1.4 g of compound (10).

Example B10

Preparation of Compound (11)

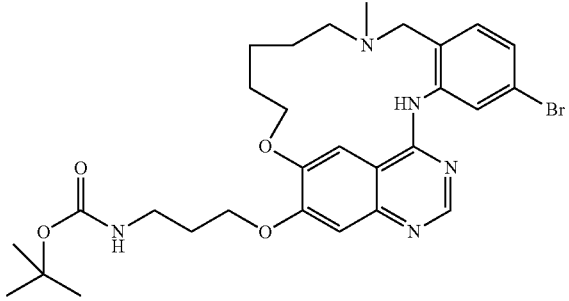 [SMILES: CN1CCCCCOc2cc3c(ncnc3cc2OCCCNC(=O)OC(C)(C)C)Nc2cc(Br)ccc2C1]

A mixture of intermediate (42) (0.0017 mol), (3-hydroxypropyl)-1,1-dimethylethyl ester carbamic acid (0.0041 mol) and triphenylphosphine (0.0038 mol) in THF (20 ml) was stirred at room temperature. DIAD (0.004 mol) was added dropwise and the reaction mixture was stirred for 1 hour at room temperature. The solvent was evaporated and the residue was stirred up in CH₃CN (50 ml). The precipitate was filtered off, washed with CH₃CN and dried, yielding 0.815 g (80%) of compound (11).

Example B11

Preparation of Compound (12)

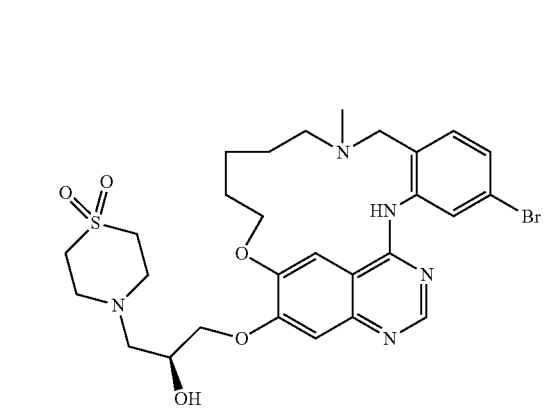 [SMILES: CN1CCCCCOc2cc3c(ncnc3cc2OC[C@@H](O)CN2CCS(=O)(=O)CC2)Nc2cc(Br)ccc2C1]

A mixture of intermediate (51) (0.00032 mol) and 1,1-dioxidethiomorpholine (0.00185 mol) in 2-propanol (2 ml) was stirred for 2 hours at 70° C. DMF (2 ml) was added and the resultant reaction mixture was stirred for 16 hours at 70° C. The reaction mixture was cooled at room temperature slowly. The precipitate was filtered off and dried, yielding 0.108 g (53%) of compound (12) (R-configuration).

Example B12

Preparation of Compound (13)

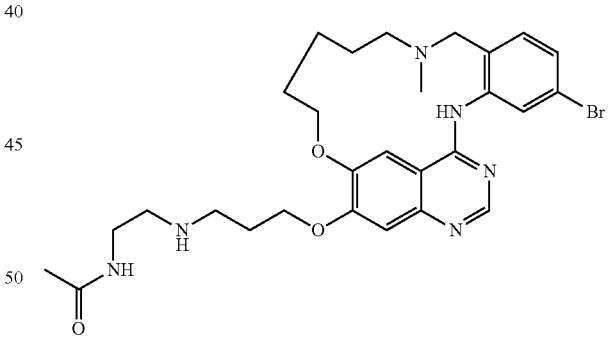

Intermediate (52) (0.003190 mol) was stirred in CH₃CN (20 ml). N-(2-aminoethyl)acetamide (2 ml) was added and the resultant reaction mixture was stirred overnight at room temperature. K₂CO₃ (aq.) (0.009569 mol) was added and the reaction mixture was stirred and refluxed for 2 hours, then cooled to room temperature and the solvent was evaporated in vacuo. Water was added to the residue and this mixture was stirred for 30 minutes at room temperature. The yellow precipitate was filtered off and dried. This fraction was purified by flash column chromatography over a Biotage cartridge (eluent: CH₂Cl₂/(CH₃OH/NH₃) 95/5 up to 80/20). The product fractions were collected and the solvent was evaporated, yielding 0.94 g of compound (13).

Example B13

Preparation of Compound (14)

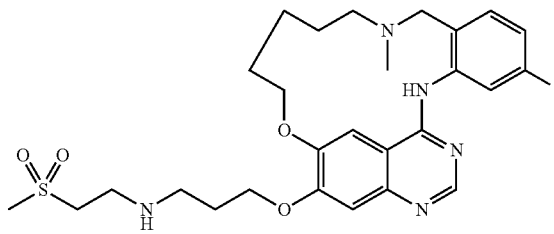

Intermediate (52) (0.003544 mol) was stirred in $CH_3CN$ (20 ml). 2-(Methylsulfonyl)ethanamine hydrochloride (0.007088 mol) was added. $K_2CO_3$ (aq.) (0.0106 mol) was added and the reaction mixture was stirred and refluxed overnight, then cooled to room temperature and the solvent was evaporated in vacuo. Water was added to the residue and this mixture was stirred for 10 minutes at room temperature. The yellow precipitate was filtered off and dried. This fraction was purified by flash column chromatography over a Biotage cartridge (eluent: $CH_2Cl_2/(CH_3OH/NH_3)$ from 100/0 to 94/6). The product fractions were collected and the solvent was evaporated, yielding 1.24 g (58%) of compound (14).

Table F-1 lists the compounds that were prepared according to one of the above Examples. The following abbreviations were used in the tables: M.P. stands for the melting point.

TABLE F-1

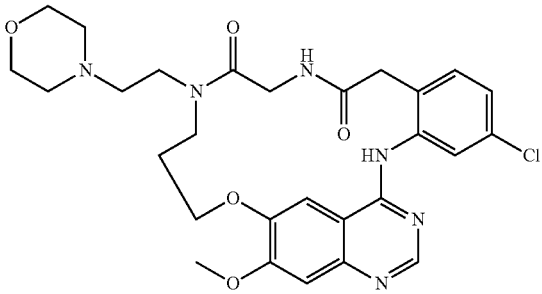 [SMILES: COc1cc2ncnc3c2cc1OCCCN(CCN1CCOCC1)C(=O)CNC(=O)Cc1ccc(Cl)cc1N3]

Co. No. (15); Ex. B1

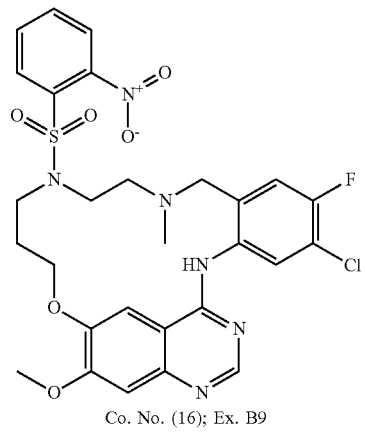

Co. No. (16); Ex. B9

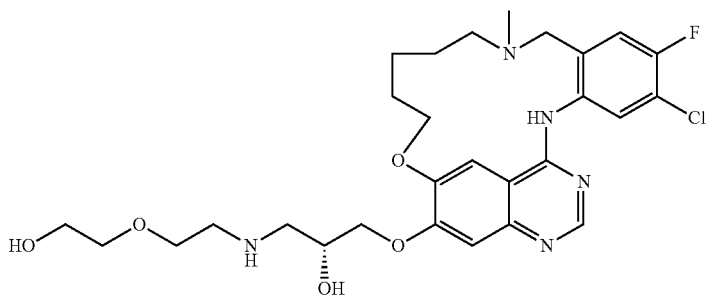 [SMILES: CN1CCCCCOc2cc3c(ncnc3cc2OC[C@H](O)CNCCOCCO)Nc2cc(Cl)c(F)cc2C1]

Co. No. (17); Ex. B11; R-configuration

TABLE F-1-continued
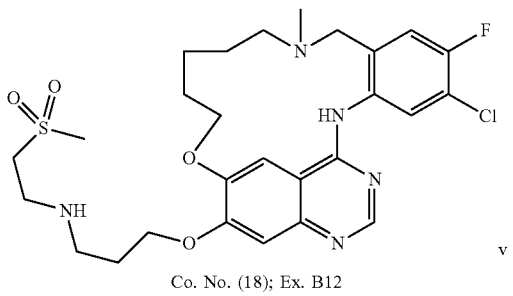
Co. No. (18); Ex. B12
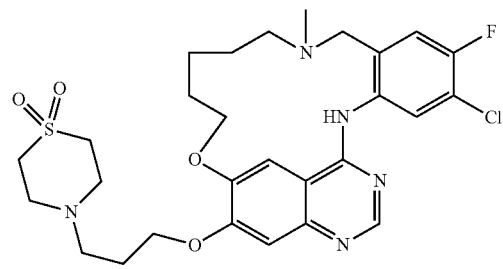 [SMILES: CN1CCCCCOc2cc3c(ncnc3cc2OCCCN2CCS(=O)(=O)CC2)Nc2cc(Cl)c(F)cc2C1]
Co. No. (19); Ex. B12
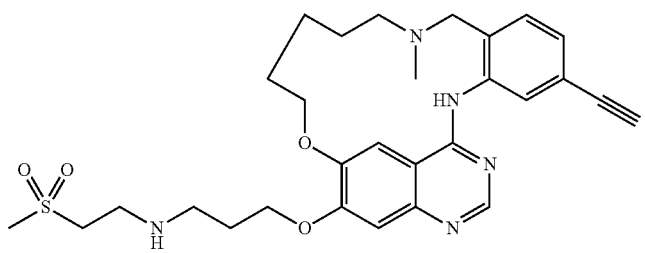 [SMILES: C#Cc1ccc2c(c1)Nc1ncnc3cc(OCCCNCCS(C)(=O)=O)c(cc13)OCCCCCN(C)C2]
Co. No. (20); Ex. B13;
M.P.: 197.7-199.5° C. (decomposition)
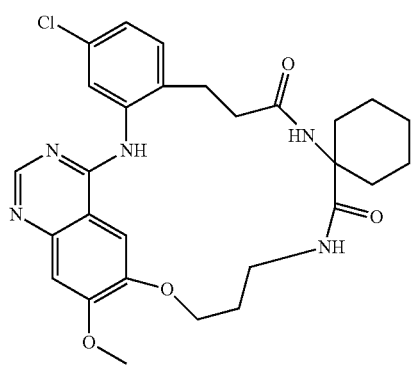 [SMILES: COc1cc2ncnc3c2cc1OCCCNC(=O)C1(CCCCC1)NC(=O)CCc1ccc(Cl)cc1N3]
Co. No. (21); Ex. B6

TABLE F-1-continued

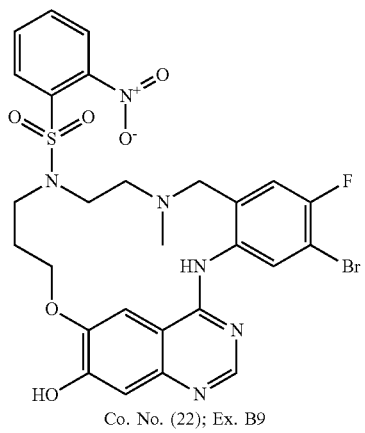

Co. No. (22); Ex. B9

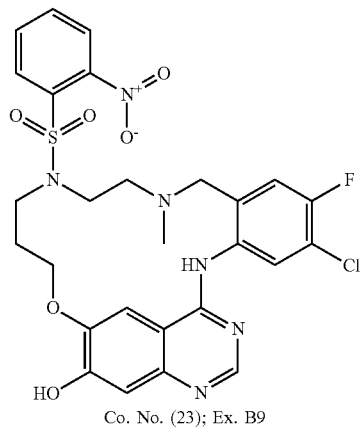

Co. No. (23); Ex. B9

Compound Identification
LCMS-Methods:

The HPLC gradient was supplied by a Waters Alliance HT 2790 system with a column heater set at 40° C. Flow from the column was split to a Waters 996 photodiode array (PDA) detector and a Waters-Micromass ZQ mass spectrometer with an electrospray ionization source operated in positive and negative ionization mode.

Method 1:

Reversed phase HPLC was carried out on a Xterra MS C18 column (3.5 mm, 4.6×100 mm) with a flow rate of 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 50% B and 50% C in 6.5 minutes, to 100% B in 1 minute, 100% B for 1 minute and reequilibrate with 100% A for 1.5 minutes. An injection volume of 10 uL was used.

Method 2:

Reversed phase HPLC was carried out on a Chromolith (4.6×25 mm) with a flow rate of 3 ml/min. Three mobile phases (mobile phase A 95% 25 mM ammoniumacetate+5% acetonitrile; mobile phase B: acetonitrile; mobile phase C: methanol) were employed to run a gradient condition from 96% A to 2% B and 2% C in 0.9 minutes, to 49% B and 49% C in 0.3 minute, 100% B for 0.2 minute. An injection volume of 2 uL was used.

Method 3:

Reversed phase HPLC was carried out on a Xterra MS C18 column (3.5 mm, 4.6×100 mm) with a flow rate of 1.6 ml/min. Two mobile phases (mobile phase A methanol/H2O; mobile phase B 0.1% formic acid) were employed to run a gradient condition from 100% B to 5% B 12 minutes. An injection volume of 10 uL was used.

Method 4:

Reversed phase HPLC was carried out on a Xterra MS C18 column (3.5 mm, 4.6×100 mm) with a flow rate of 1.6 ml/min. Three mobile phases (mobile phase A 95% 25 mM ammonium acetate+5% acetonitrile; mobile phase B: acetonitrile; mobile phase C: methanol) were employed to run a gradient condition from 100% A to 30% A, 35% B; 35% C in 3 minutes to 50% B and 50% C in 3.5 minutes, to 100% B in 0.5 minute. An injection volume of 10 uL was used.

Method 5:

Reversed phase HPLC was carried out on a Kromasil C18 column (3.5 mm, 4.6×100 mm) with a flow rate of 1 ml/min. Three mobile phases (mobile phase A ammonium acetate; mobile phase B: acetonitrile; mobile phase C: formic acid) were employed to run a gradient condition from 30% A, 40% B, 30% C for 1 minute to 100% B for 5 minutes. An injection volume of 10 uL was used.

TABLE retention time (RT in minutes) and molecular weight as the MH+

| Comp. No. | Rt | MW(MH+) | LC/GC/MS Method |
|---|---|---|---|
| Int. 35 | 3.84 | 317 | 1 |
| Int. 41 | 1.24 | 457 | 1 |

TABLE-continued retention time (RT in minutes) and molecular weight as the MH+

| Comp. No. | Rt | MW(MH+) | LC/GC/MS Method |
|---|---|---|---|
| Int. 40 | 6.01 | 475 | 1 |
| Int. 1 | 3.99 | 271 | 1 |
| Int. 2 | 5.31 | 487 | 1 |
| Int. 22 | 10.12 | 652 | 1 |
| Int. 25 | 9.62 | 684 | 1 |

TABLE-continued retention time (RT in minutes) and molecular weight as the MH+

| Comp. No. | Rt | MW(MH+) | LC/GC/MS Method |
|---|---|---|---|
| 10 | 6.24 | 675 | 1 |
| 16 | 6.21 | 631 | 1 |
| 22 | 5.92 | 661 | 1 |
| 23 | 5.89 | 617 | 1 |
| 17 | 8.48 | 578 | 1 |
| Int. 39 | 6.32 | 559 | 1 |
| Int. 37 | 6.47 | 373 | 1 |
| Int. 36 | 5.53 | 331 | 1 |
| Int. 3 | 4.62 | 445 | 1 |
| Int. 4 | 5.63 | 551 | 1 |
| Int. 5 | 4.39 | 601 | 1 |
| Int. 23 | 8.26 | 729 | 1 |
| Int. 21 | 1 | 531 | 2 |
| Int. 43 | 1.2 | 545 | 2 |
| Int. 42 | 1.16 | 443 | 2 |
| Int. 44 | 1.29 | 563 | 2 |
| Int. 49 | 1.12 | 573 | 2 |
| Int. 47 | 1.03 | 493 | 2 |
| 11 | 1.27 | 600 | 2 |
| 12 | 1.13 | 634 | 2 |
| Int. 51 | 1.2 | 499 | 2 |
| 14 | 1.18 | 606 | 2 |
| Int. 45 | 1.13 | 307 | 2 |
| 19 | 1.17 | 592 | 2 |
| 18 | 1.17 | 580 | 2 |
| Int. 20 | 1.05 | 575 | 2 |
| Int. 52 | 1.27 | 565 | 2 |
| Int. 48 | 0.98 | 451 | 2 |
| 20 | 7.41 | 551 | 3 |
| 8 | 9.24 | 566 | 3 |
| 21 | 8.11 | 538 | 3 |
| 13 | 6.43 | 585 | 4 |
| Int. 12 | 6.57 | 490 | 5 |
| Int. 13 | 8.62 | 474 | 5 |
| Int. 10 | 4.95 | 449 | 5 |
| Int. 15 | 6.32 | 536 | 5 |
| Int. 17 | 4.88 | 586 | 5 |

C. Pharmacological Examples

C1 Kinase Profiling

The in vitro inhibition of a panel of kinases was assessed using the glass-fiber filter technology as described by Davies, S. P. et al., Biochem J. (2000), 351; p. 95-105.

In the glass-fiber filter technology the activity of the kinase of interest is measured using an appropriate substrate that is incubated with the aforementioned kinase protein in the presence of ($^{33}$P) radiolabeled ATP. ($^{33}$P) Phosporylation of the substrate is subsequently measured as radioactivity bound on a glassfiber-filter.

DETAILED DESCRIPTION

All kinases are pre-diluted to a 10× working concentration prior to addition into the assay. The composition of the dilution buffer for each kinase is detailed below.

| Buffer Composition | Kinase(s) |
|---|---|
| 50 mM Tris pH 7.5, 0.1 mM EGTA, 0.1 mM Na$_3$VO$_4$, 0.1% β-mercaptoethanol, 1 mg/ml BSA | Blk, Fyn, Lck, Lyn |
| 20 mM MOPS pH 7.0, 1 mM EDTA, 0.1% β-mercaptoethanol, 0.01% Brij-35, 5% glycerol, 1 mg/ml BSA | Abl, Bmx, EGFR, Fes, Fgr, Fms, Flt1, CDK5/p35, CDK6/cyclinD3, ErbB4, cSRC, Ret, Yes, Hck |

All substrates are dissolved and diluted to working stocks in de-ionised water.

Abl Human

In a final reaction volume of 25 μl, Abl (h) (5-10 mU) is incubated with 8 mM MOPS pH 7.0, 0.2 mM EDTA, 50 μM EAIYAAPFAKKK, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a P30 filtermat and washed three times for 5 minutes in 75 mM phosphoric acid and once in methanol prior to drying and scintillation counting.

Blk Mouse

In a final reaction volume of 25 μl, Blk (m) (5-10 mU) is incubated with 50 mM Tris pH 7.5, 0.1 mM EGTA, 0.1 mM Na3VO4, 0.1% β-mercaptoethanol, 0.1 mg/ml poly(Glu, Tyr) 4:1, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a Filtermat A and washed three times for 5 minutes in 75 mM phosphoric acid and once in methanol prior to drying and scintillation counting.

Bmx Human

In a final reaction volume of 25 μl, Bmx (h) (5-10 mU) is incubated with 8 mM MOPS pH 7.0, 0.2 mM EDTA, 0.1 mg/ml poly(Glu, Tyr) 4:1, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a Filtermat A and washed three times for 5 minutes in 75 mM phosphoric acid and once in methanol prior to drying and scintillation counting.

CDK5/p35 Human

In a final reaction volume of 25 μl, CDK5/p35 human (5-10 mU) is incubated with 8 mM MOPS pH 7.0, 0.2 mM EDTA, 0.1 mg/ml histone H1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

CDK6/CyclinD3 Human

In a final reaction volume of 25 µl, CDK6/cyclinD3 human (5-10 mU) is incubated with 8 mM MOPS pH 7.0, 0.2 mM EDTA, 0.1 mg/ml histone H1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

cSRC Human

In a final reaction volume of 25 µl, cSRC (h) (5-10 mU) is incubated with 8 mM MOPS pH 7.0, 0.2 mM EDTA, 250 µM KVEKIGEGTYGVVYK (Cdc2 peptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution.

10 µl of the reaction is then spotted onto a P30 filtermat and washed three times for 5 minutes in 75 mM phosphoric acid and once in methanol prior to drying and scintillation counting.

EGFR Human

In a final reaction volume of 25 µl, EGFR (h) (5-10 mU) is incubated with 8 mM MOPS pH 7.0, 0.2 mM EDTA, 10 mM MnCl2, 0.1 mg/ml poly(Glu, Tyr) 4:1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a Filtermat A and washed three times for 5 minutes in 75 mM phosphoric acid and once in methanol prior to drying and scintillation counting.

ErbB4 Human

In a final reaction volume of 25 µl, ErbB4 (h) (5-10 mU) is incubated with 8 mM MOPS pH 7.0, 0.2 mM EDTA, 10 mM MnCl2, 0.1 mg/ml poly(Glu, Tyr) 4:1, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a Filtermat A and washed three times for 5 minutes in 75 mM phosphoric acid and once in methanol prior to drying and scintillation counting.

Fgr Human

In a final reaction volume of 25 µl, Fgr human (5-10 mU) is incubated with 8 mM MOPS pH 7.0, 0.2 mM EDTA, 0.1 mg/ml poly(Glu, Tyr) 4:1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a Filtermat A and washed three times for 5 minutes in 75 mM phosphoric acid and once in methanol prior to drying and scintillation counting.

Fyn Human

In a final reaction volume of 25 µl, Fyn human (5-10 mU) is incubated with 50 mM Tris pH 7.5, 0.1 mM EGTA, 0.1 mM Na$_3$VO$_4$, 250 µM KVEKIGEGTYGVVYK (Cdc2 peptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

Lck Human

In a final reaction volume of 25 µl, Lck (h) (5-10 mU) is incubated with 50 mM Tris pH 7.5, 0.1 mM EGTA, 0.1 mM Na3VO4, 250 µM KVEKIGEGTYGVVYK (Cdc2 peptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution.

10 µl of the reaction is then spotted onto a P30 filtermat and washed three times for 5 minutes in 75 mM phosphoric acid and once in methanol prior to drying and scintillation counting.

Lyn Human

In a final reaction volume of 25 µl, Lyn (h) (5-10 mU) is incubated with 50 mM Tris pH 7.5, 0.1 mM EGTA, 0.1 mM Na3VO4, 0.1% β-mercaptoethanol, 0.1 mg/ml poly(Glu, Tyr) 4:1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a Filtermat A and washed three times for 5 minutes in 75 mM phosphoric acid and once in methanol prior to drying and scintillation counting.

Ret Human

In a final reaction volume of 25 µl, Ret human (5-10 mU) is incubated with 8 mM MOPS pH 7.0, 0.2 mM EDTA, 250 µM KKKSPGEYVNIEFG, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

Yes Human

In a final reaction volume of 25 µl, Yes (h) (5-10 mU) is incubated with 8 mM MOPS pH 7.0, 0.2 mM EDTA, 0.1 mg/ml poly(Glu, Tyr) 4:1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a Filtermat A and washed three times for 5 minutes in 75 mM phosphoric acid and once in methanol prior to drying and scintillation counting.

Flt1 Human

In a final reaction volume of 25 µl, Flt1 human (5-10 mU) is incubated with 8 mM MOPS pH 7.0, 0.2 mM EDTA, 250 µM KKKSPGEYVNIEFG, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

Hck Human

In a final reaction volume of 25 µl, Hck human (5-10 mU) is incubated with 8 mM MOPS pH 7.0, 0.2 mM EDTA, 250 µM KVEKIGEGTYGVVYK (Cdc2 peptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

The following tables provides the scores for the compounds according to the invention, obtained at a test concentration of $10^{-6}$ M using the above mentioned kinase assays. Score 1=10-30% inhibition, Score 2=30-60% inhibition, Score 3=60-80% inhibition and Score 4=>80% inhibition.

| Compound No | Abl | CDK5/p35 | CDK6/cyclinD3 | cSRC | EGFR | Fgr |
|---|---|---|---|---|---|---|
| Int. 43 | 3 | | 1 | 4 | 4 | 2 |
| 1 | | | | 3 | 4 | |
| 15 | 4 | 1 | | 2 | 4 | |
| Int. 25 | 1 | | | 2 | 4 | |
| 8 | 1 | | | 4 | 4 | |
| 11 | | | | 3 | 4 | 1 |
| 12 | | | | 4 | 4 | 3 |
| 13 | | | | 4 | 4 | 4 |
| 14 | | | | 4 | 4 | 3 |
| 20 | | | | 4 | 4 | |
| 19 | | | | 4 | 4 | 3 |
| 2 | | | | 4 | 4 | 1 |
| 4 | | | | 4 | 4 | |
| Int. 16 | | | | 4 | 4 | 1 |
| 5 | | | | 4 | 4 | 1 |
| 6 | 4 | | | 4 | 4 | |
| 17 | 4 | | | 4 | 4 | |
| 18 | 4 | | | 4 | 4 | |

| Compound No | Fyn | Lck | Lyn | Ret | Yes | Flt1 |
|---|---|---|---|---|---|---|
| 43 | 4 | 4 | 4 | 4 | 4 | 3 |
| 1 | | 1 | 2 | | 2 | |
| 15 | 2 | 2 | 3 | 1 | 3 | 1 |
| Int. 25 | 2 | 3 | 3 | 2 | 4 | 1 |
| 8 | 3 | 4 | | 4 | 4 | |
| 11 | 3 | | 2 | 4 | 4 | 2 |
| 12 | 4 | 4 | 4 | 4 | 4 | 3 |
| 13 | | 4 | 4 | 4 | 4 | 4 |
| 14 | | 4 | 4 | 4 | 4 | 4 |
| 20 | | 4 | 4 | 4 | 4 | 4 |
| 19 | 4 | 4 | | 4 | 4 | 4 |
| 2 | 4 | 4 | | 4 | 4 | 2 |
| 4 | 3 | 4 | | 4 | 4 | 2 |
| Int. 16 | 4 | 4 | 4 | 4 | | 3 |
| 5 | 3 | 3 | 4 | 3 | 4 | 2 |
| 6 | 4 | 4 | 4 | | 4 | |
| 17 | 4 | 4 | 4 | | 4 | |
| 18 | 4 | 4 | 4 | | 4 | |

| Compound No | Blk | Bmx | ErbB4 |
|---|---|---|---|
| 43 | 3 | — | 1 |
| 1 | 2 | | |
| 15 | 2 | | 1 |
| Int. 25 | 2 | | 2 |
| 8 | | | 3 |
| 11 | 2 | 1 | 1 |
| 12 | 4 | 2 | 3 |
| 13 | 4 | 3 | 4 |
| 14 | 4 | 2 | 4 |
| 20 | 4 | 3 | 4 |
| 19 | 4 | 3 | 3 |
| 2 | 4 | 2 | 2 |
| 4 | 4 | 2 | 2 |
| Int. 16 | 4 | 2 | 1 |
| 5 | 4 | 2 | 1 |
| 6 | | 2 | 3 |
| 17 | | 3 | 4 |
| 18 | | 2 | 4 |

D. Composition Examples

The following formulations exemplify typical pharmaceutical compositions suitable for systemic administration to animal and human subjects in accordance with the present invention.

"Active ingredient" (A.I.) as used throughout these examples relates to a compound of formula (I) or a pharmaceutically acceptable addition salt thereof.

Example D.1

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinyl-pyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10.000 tablets, each comprising 10 mg of the active ingredient.

Coating

To a solution of methyl cellulose (10 g) in denaturated ethanol (75 ml) there was added a solution of ethyl cellulose (5 g) in DCM (150 ml). Then there were added DCM (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the whole was homogenated. The tablet cores were coated with the thus obtained mixture in a coating apparatus.

The invention claimed is:
1. A compound having the formula

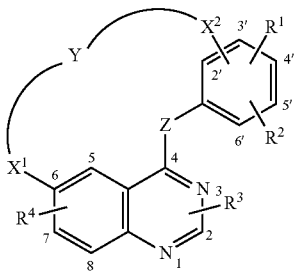

(I)

the N-oxide forms, the pharmaceutically acceptable addition salts and the stereochemically isomeric forms thereof, wherein Z represents NH;
Y represents —$C_{3-9}$alkyl-, —$C_{2-9}$alkenyl-, —$C_{1-5}$alkyl-oxy-$C_{1-5}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-6}$alkyl-NH—CO—, —NH—CO—$C_{1-6}$alkyl-, —CO—$C_{1-7}$alkyl-, —$C_{1-7}$alkyl-CO—, $C_{1-6}$alkyl—CO—$C_{1-6}$alkyl, —$C_{1-2}$alkyl-$NR^{23}$—CO—$CR^{16}R^{17}$—NH—, —$C_{1-2}$alkyl-CO—NH—$CR^{18}R^{19}$—CO—, —$C_{1-2}$alkyl-CO—$NR^{20}$—$C_{1-3}$alkyl-CO—, —$C_{1-2}$alkyl-$NR^{21}$—$CH_2$—CO—NH—$C_{1-3}$alkyl-, —$NR^{22}$—CO—$C_{1-3}$alkyl-NH—, —$C_{1-3}$alkyl-NH—CO—$Het^{20}$-, $C_{1-2}$alkyl-CO—$Het^{21}$-CO—, or -$Het^{22}$-$CH_2$—CO—NH—$C_{1-3}$alkyl-;

$X^1$ represents O, —O—$C_{1-2}$alkyl-, —O—N=CH—, $NR^{11}$ or —$NR^{11}$—$C_{1-2}$alkyl-;

$X^2$ represents a direct bond, $C_{1-2}$alkyl, O, —O—$C_{1-2}$alkyl-, CO, —CO—$C_{1-2}$alkyl-, —O—N=CH—, $NR^{12}$ or $NR^{12}$—$C_{1-2}$alkyl-;

$R^1$ represents hydrogen, cyano, halo or hydroxy;

$R^2$ represents hydrogen, cyano, halo, hydroxy, hydroxycarbonyl-, $C_{1-4}$alkyloxycarbonyl-, $Het^{16}$-carbonyl-, $C_{1-4}$alkyl-, $C_{2-6}$alkynyl-, $Ar^5$, $Het^1$ or dihydroxyborane;

$R^3$ represents hydrogen, cyano, halo, hydroxy, formyl, $C_{1-6}$alkoxy-, $C_{1-6}$alkyl-, $C_{1-6}$alkoxy- substituted with halo, or $R^3$ represents $C_{1-4}$alkyl substituted with one or where possible two or more substituents selected from hydroxy or halo;

$R^4$ represents $Ar^4$—$C_{1-4}$alkyloxy-, $C_{1-4}$alkyloxy- or $R^4$ represents $C_{1-4}$alkyloxy substituted with one or where possible two or more substituents selected from hydroxy-, halo, $C_{1-4}$alkyloxy-, $C_{1-4}$alkyloxy-$C_{1-4}$alkyloxy-, $NR^{37}R^{38}$-carbonyloxy-, $Het^5$-carbonyloxy-, $NR^7R^8$, $NR^9R^{10}$-carbonyl-, $Het^3$-carbonyl-, $Het^{13}$-oxy- or $Het^2$-;

$R^7$ represents hydrogen, hydroxy-$C_{1-4}$alkyl- or $C_{1-4}$alkyl;

$R^8$ represents $C_{3-6}$cycloalkyl; $Het^6$-carbonyl-; $Het^7$-aminocarbonyl-; $Het^8$;

Het⁹-oxycarbonyl-; Het¹⁰-sulfonyl-; $C_{1-4}$alkyloxycarbonyl;

mono- or di($C_{1-4}$alkyl)aminocarbonyl-; mono- or di($C_{1-4}$alkyl)aminocarbonyl substituted with $C_{1-4}$alkylsulfonyl-; or $C_{1-4}$alkylcarbonyl optionally substituted with one or more substituents selected from $C_{1-4}$alkylsulfonyl, hydroxy- and $C_{1-4}$alkyloxy-; or $R^8$ represents $C_{1-4}$alkyl substituted with one or more substituents selected from $C_{1-4}$alkylsulfonyl-, $NR^{25}R^{26}$, aminocarbonyloxy-, $C_{1-4}$alkylcarbonyloxy-, aminocarbonyl-, hydroxy-$C_{1-4}$alkyloxy-, $C_{1-4}$alkyloxy-$C_{1-4}$alkyloxy-, and Het¹¹;

$R^9$ represents hydrogen or $C_{1-4}$alkyl-;

$R^{10}$ represents Het⁴ or $C_{1-4}$alkyl- substituted with $C_{1-4}$alkylsulfonyl-;

$R^{11}$ represents hydrogen, $C_{1-4}$alkyl- or $C_{1-4}$alkyl-oxycarbonyl-;

$R^{12}$ represents hydrogen, $C_{1-4}$alkyl-, $C_{1-6}$alkyloxycarbonyl- or $C_{1-6}$alkyloxycarbonyl-substituted with phenyl;

$R^{13}$ represents hydrogen, Het¹⁴-$C_{1-4}$alkyl, $C_{1-6}$alkyloxycarbonyl optionally substituted with phenyl or $R^{13}$ represents Ar⁶-sulfonyl or Het²⁴-$C_{1-4}$alkylcarbonyl;

$R^{14}$ and $R^{15}$ are each independently selected from hydrogen, $C_{1-4}$alkyl, Het¹⁵-$C_{1-4}$alkyl- or $C_{1-4}$alkyloxy$C_{1-4}$ alkyl-;

$R^{16}$ and $R^{17}$ each independently represents hydrogen, $C_{1-4}$alkyl or $C_{1-4}$alkyl substituted with hydroxy-, $C_{3-6}$cycloalkyl or phenyl; or $R^{16}$ and $R^{17}$ taken together with the carbon atom to which they are attached form a $C_{3-6}$cycloalkyl;

$R^{18}$ represents hydrogen or $C_{1-4}$alkyl optionally substituted with hydroxy or phenyl;

$R^{19}$ represents hydrogen or $C_{1-4}$alkyl;

$R^{20}$ represents hydrogen or $C_{1-4}$alkyl;

$R^{21}$ represents hydrogen, $C_{1-4}$alkyl, Het²³-$C_{1-4}$alkylcarbonyl- or $R^{21}$ represents mono- or di($C_{1-4}$alkyl)amino-$C_{1-4}$alkyl-carbonyl- optionally substituted with hydroxy, pyrimidinyl, dimethylamine or $C_{1-4}$alkyloxy;

$R^{22}$ represents hydrogen or $C_{1-4}$alkyl optionally substituted with hydroxy or $C_{1-4}$alkyloxy;

$R^{23}$ represents $C_{1-4}$alkyl optionally substituted with hydroxy-, $C_{1-4}$alkyloxy- or Het²⁵; $R^{23}$ may also represent hydrogen when $R^{16}$ and $R^{17}$ taken together with the carbon atom to which they are attached form a $C_{3-6}$cycloalkyl;

$R^{25}$ and $R^{26}$ each independently represent hydrogen, $C_{1-4}$alkyl, $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

$R^{27}$ and $R^{28}$ each independently represent hydrogen, $C_{1-4}$alkyl, $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-; or for those compounds of formula (I) wherein Het² represents a heterocycle selected from morpholinyl, piperazinyl, piperidinyl, pyrrolidinyl or thiomorpholinyl substituted with $NR^{27}R^{28}$—$C_{1-4}$alkyl said $R^{27}$ and $R^{28}$ each independently represent $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

$R^{29}$ and $R^{30}$ each independently represent hydrogen, aminosulfonyl, aminocarbonyl, mono- or di($C_{1-4}$alkyl)aminocarbonyl-, mono- or di($C_{1-4}$alkyl)aminosulfonyl-, or $C_{1-4}$alkyl- optionally substituted with one or more substituents selected from $NR^{31}R^{32}$, $C_{1-4}$alkylsulfonyl, aminocarbonyloxy-, hydroxy-, $C_{1-4}$alkyloxy-, aminocarbonyl- and mono- or di($C_{1-4}$alkyl)aminocarbonyl-, or $C_{1-4}$alkyloxycarbonyl optionally substituted with one or more substituents selected from hydroxy, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-;

$R^{31}$ and $R^{32}$ each independently represent hydrogen, $C_{1-4}$alkyl, $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

$R^{33}$ represents hydrogen or $C_{1-4}$alkyl;

$R^{34}$ represents $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

$R^{35}$ represents hydrogen or $C_{1-4}$alkyl;

$R^{36}$ represents $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

$R^{37}$ and $R^{38}$ each independently represent hydrogen, $C_{1-4}$alkyl, $C_{1-4}$alkylsulfonyl-, Het¹² or $C_{1-4}$alkyl substituted with one or more substituents selected from $C_{1-4}$alkylsulfonyl-, hydroxy- and $C_{1-4}$alkyloxy-;

$R^{39}$ and $R^{40}$ each independently represent aminosulfonyl, aminocarbonyl, mono- or di($C_{1-4}$alkyl)aminocarbonyl-, mono- or di($C_{1-4}$alkyl)aminosulfonyl-, or $C_{1-4}$alkyl- substituted with one or more substituents selected from $NR^{31}R^{32}$, $C_{1-4}$alkylsulfonyl, aminocarbonyloxy-, hydroxy-, $C_{1-4}$alkyloxy-, aminocarbonyl- and mono- or di($C_{1-4}$alkyl)aminocarbonyl-, or $C_{1-4}$alkyloxycarbonyl optionally substituted with one or more substituents selected from hydroxy, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-;

Het¹ represents thiazolyl or 2-bora-1,3-dioxolanyl wherein said Het¹ is optionally substituted with one or where possible two, three, four or more substituents selected from amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl- mono- or di($C_{1-4}$alkyl)amino- or amino-carbonyl-;

Het² represents a heterocycle selected from tetrahydropyranyl, tetrahydrofuranyl, furanyl, 1,1-dioxothiomorpholinyl, piperazininonyl, tetrahydro-1,1-dioxido-2H-thiopyranyl, piperidinonyl, azetidinyl or 2-azetidinonyl wherein said Het² is optionally substituted with one or where possible two or more substituents selected from hydroxy, amino, $NR^{29}R^{30}$, aminocarbonyl, mono- or di($C_{1-4}$alkyl)aminocarbonyl, $C_{1-4}$alkylsulfonyl or C$_{1-4}$alkyl- optionally substituted with one or more substituents selected from NR$^{27}$R$^{28}$, C$_{1-4}$alkylsulfonyl, aminocarbonyloxy-, aminocarbonyl- and mono- or di(C$_{1-4}$alkyl)aminocarbonyl-, or C$_{1-4}$alkyloxy- optionally substituted with C$_{1-4}$alkyloxy-, or C$_{1-4}$alkyloxycarbonyl optionally substituted with one or more substituents selected from hydroxy, C$_{1-4}$alkyloxy- and C$_{1-4}$alkylsulfonyl-, or C$_{1-4}$alkylcarbonyl optionally substituted with one or more substituents selected from hydroxy-, C$_{1-4}$alkyloxy- and C$_{1-4}$alkylsulfonyl-; or Het$^2$ represents a heterocycle selected from morpholinyl, piperazinyl, piperidinyl, pyrrolidinyl, thiomorpholinyl or 1,1-dioxothiomorpholinyl wherein said Het$^2$ is optionally substituted with one or where possible two or more substituents selected from C$_{1-4}$alkyl- optionally substituted with one or more substituents selected from NR$^{27}$R$^{28}$, C$_{1-4}$alkylsulfonyl, aminocarbonyloxy-, aminocarbonyl- and mono- or di(C$_{1-4}$alkyl)aminocarbonyl-, or C$_{1-4}$alkyloxy- optionally substituted with C$_{1-4}$alkyloxy-, or C$_{1-4}$alkyloxycarbonyl optionally substituted with one or more substituents selected from hydroxy, C$_{1-4}$alkyloxy- and C$_{1-4}$alkylsulfonyl-, or C$_{1-4}$alkylcarbonyl optionally substituted with one or more substituents selected from hydroxy-, C$_{1-4}$alkyloxy- and C$_{1-4}$alkylsulfonyl-;

Het$^3$ represents a heterocycle selected from tetrahydropyranyl, tetrahydrofuranyl, furanyl, 1,1-dioxothiomorpholinyl, piperazininonyl, tetrahydro-1,1-dioxido-2H-thiopyranyl, piperidinonyl, azetidinyl or 2-azetidinonyl wherein said Het$^3$ is optionally substituted with one or where possible two or more substituents hydroxy-, amino, C$_{1-4}$alkyl-, C$_{3-6}$cycloalkyl-C$_{1-4}$alkyl-, aminosulfonyl-, mono- or di(C$_{1-4}$alkyl)aminosulfonyl-, amino-C$_{1-4}$alkyl-, Mono- or di(C$_{1-4}$alkyl) amino-C$_{1-4}$alkyl, NR$^{35}$R$^{36}$, C$_{1-4}$alkyl-sulfonyl-C$_{1-4}$alkyl- or C$_{1-4}$alkyloxy- optionally substituted with C$_{1-4}$alkyloxy- or hydroxy; or Het$^3$ represents a heterocycle selected from morpholinyl, piperazinyl, piperidinyl, furanyl or pyrrolidinyl wherein said Het$^3$ is substituted with one or where possible two or more substituents selected from NR$^{35}$R$^{36}$, C$_{1-4}$alkyl-sulfonyl-C$_{1-4}$alkyl- or C$_{1-4}$alkyloxy- optionally substituted with C$_{1-4}$alkyloxy- or hydroxy;

Het$^4$ represents a heterocycle selected from morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said Het$^4$ is substituted with one or where possible two or more substituents selected from C$_{1-4}$alkyl-sulfonyl-C$_{1-4}$alkyl-, C$_{1-4}$alkyloxy- optionally substituted with C$_{1-4}$alkyloxy- or hydroxy;

Het$^5$ represents a heterocycle selected from furanyl, piperazinyl, 1,1-dioxothiomorpholinyl, piperazininonyl, piperidinyl, tetrahydro-1,1-dioxido-2H-thiopyranyl, piperidinonyl, morpholinyl or pyrrolidinyl wherein said Het$^5$ is optionally substituted with hydroxy, amino, mono- or di(C$_{1-4}$alkyl)-amino-, C$_{1-4}$alkyl, Het$^6$ and Het$^7$ each independently represents a heterocycle selected from piperazinyl, piperidinyl or pyrrolidinyl wherein said heterocycles are optionally substituted with one or more substituents selected from hydroxy-, amino, hydroxy-C$_{1-4}$alkyl-, C$_{1-4}$alkyloxy-C$_{1-4}$alkyl- and C$_{1-4}$alkyl-;

Het$^8$ represents a heterocycle selected from tetrahydropyranyl, tetrahydrofuranyl, 1,1-dioxothiomorpholinyl, piperazininonyl, tetrahydro-1,1-dioxido-2H-thiopyranyl, piperidinonyl, azetidinyl or 2-azetidinonyl wherein said Het$^8$ is optionally substituted with aminosulfonyl, aminocarbonyl, mono- or di(C$_{1-4}$alkyl)aminocarbonyl-, mono- or di(C$_{1-4}$alkyl)aminosulfonyl-, or C$_{1-4}$alkyl- optionally substituted with one or more substituents selected from amino, mono- or di(C$_{1-4}$alkyl)amino-, NR$^{33}$R$^{34}$, C$_{1-4}$alkylsulfonyl, aminocarbonyloxy-, hydroxy-, C$_{1-4}$alkyloxy-, aminocarbonyl- and mono- or di(C$_{1-4}$alkyl)aminocarbonyl-, or C$_{1-4}$alkyloxycarbonyl optionally substituted with one or more substituents selected from hydroxy, C$_{1-4}$alkyloxy- and C$_{1-4}$alkylsulfonyl-, or C$_{1-4}$alkylcarbonyl optionally substituted with one or more substituents selected from hydroxy-, C$_{1-4}$alkyloxy- and C$_{1-4}$alkylsulfonyl-; or Het$^8$ represents a heterocycle selected from furanyl, piperidinyl or piperazinyl wherein said Het$^8$ is substituted with aminocarbonyl, mono- or di(C$_{1-4}$alkyl)aminocarbonyl-, mono- or di(C$_{1-4}$alkyl)aminosulfonyl-, or C$_{1-4}$alkyl- substituted with one or more substituents selected from NR$^{33}$R$^{34}$, C$_{1-4}$alkylsulfonyl, aminocarbonyloxy-, hydroxy-, C$_{1-4}$alkyloxy-, aminocarbonyl- and mono- or di(C$_{1-4}$alkyl)aminocarbonyl-, or C$_{1-4}$alkyloxycarbonyl optionally substituted with one or more substituents selected from hydroxy, C$_{1-4}$alkyloxy- and C$_{1-4}$alkylsulfonyl-, or C$_{1-4}$alkylcarbonyl optionally substituted with one or more substituents selected from hydroxy-, C$_{1-4}$alkyloxy- and C$_{1-4}$alkylsulfonyl-;

Het$^9$ and Het$^{10}$ each independently represents a heterocycle selected from piperazinyl, piperidinyl or pyrrolidinyl wherein said heterocycles are optionally substituted with one or more substituents selected from hydroxy-, amino, hydroxy-C$_{1-4}$alkyl-, C$_{1-4}$alkyloxy-C$_{1-4}$alkyl- and C$_{1-4}$alkyl;

Het$^{11}$ represents 2-imidazolidinonyl- or

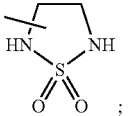

Het$^{12}$ represents a heterocycle selected from morpholinyl, piperazinyl, piperidinyl or pyrrolidinyl wherein said Het$^{12}$ is optionally substituted with one or where possible two or more substituents selected from hydroxy, amino or C$_{1-4}$alkyl-;

Het$^{13}$ represents a heterocycle selected from furanyl, piperazinyl, 1,1-dioxothiomorpholinyl, piperazininonyl, piperidinyl, tetrahydro-1,1-dioxido-2H-thiopyranyl, piperidinonyl, morpholinyl, piperazinyl or pyrrolidinyl;

Het$^{14}$ and Het$^{15}$ each independently represent a heterocycle selected from morpholinyl, piperazinyl, piperidinyl or pyrrolidinyl wherein said Het$^{14}$ and Het$^{15}$ are optionally substituted with one or where possible two or more substituents selected from hydroxy, amino or $C_{1-4}$alkyl;

$Het^{16}$ represents a heterocycle selected from piperidinyl or pyrrolidinyl;

$Het^{20}$ represents pyrrolidinyl, 2-pyrrolidinonyl, piperidinyl or hydroxy-pyrrolidinyl;

$Het^{21}$ represents pyrrolidinyl or hydroxy-pyrrolidinyl;

$Het^{22}$ represents pyrrolidinyl, piperazinyl or piperidinyl;

$Het^{23}$ and $Het^{25}$ each independently represents a heterocycle selected from morpholinyl, pyrrolidinyl, piperazinyl or piperidinyl wherein said $Het^{23}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{24}$ represents morpholinyl, pyrrolidinyl, piperazinyl or piperidinyl;

$Ar^4$, $Ar^5$ or $Ar^6$ each independently represent phenyl optionally substituted with nitro, cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl;

further characterised in that either

Y represents —$C_{1-2}$alkyl-$NR^{23}$—CO—$CR^{16}R^{17}$—NH—;

$Het^1$ represents 2-bora-1,3-dioxolanyl optionally substituted with one or where possible two, three, four or more substituents selected from amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl- mono- or di($C_{1-4}$alkyl) amino- or amino-carbonyl-;

$R^{13}$ represents $C_{1-6}$alkyloxycarbonyl optionally substituted with phenyl or $R^{13}$ represents $Ar^6$-sulfonyl or $Het^{24}$-$C_{1-4}$alkylcarbonyl; or $R^4$ represents $C_{1-4}$alkyloxy substituted with at least one substituent selected from $C_{1-4}$alkyloxy-$C_{1-4}$alkyloxy-, $NR^{37}R^{38}$-carbonyloxy-, $Het^5$-carbonyloxy-, $NR^7R^8$, $NR^9R^{10}$-carbonyl-, $Het^3$-carbonyl-, $Het^{13}$-oxy- or $Het^2$-; wherein $R^8$ represents $Het^7$-aminocarbonyl-; $Het^9$-oxycarbonyl-; $Het^{10}$-sulfonyl-; $C_{1-4}$alkyloxycarbonyl; mono- or di($C_{1-4}$alkyl)aminocarbonyl-; mono- or di($C_{1-4}$alkyl)aminocarbonyl substituted with $C_{1-4}$alkylsulfonyl-; or $C_{1-4}$alkylcarbonyl optionally substituted with one or more substituents selected from $C_{1-4}$alkylsulfonyl, hydroxy- and $C_{1-4}$alkyloxy-; or $R^8$ represents $C_{1-4}$alkyl substituted with one or more substituents selected from hydroxy $C_{1-4}$alkylsulfonyl-, alkylsulfonyl-, aminocarbonyloxy-, $C_{1-4}$alkylcarbonyloxy-, aminocarbonyl-, $C_{1-4}$alkyloxy-$C_{1-4}$alkyloxy-, and $Het^{11}$; and $Het^2$ represents a heterocycle selected from morpholinyl, piperazinyl, piperidinyl, pyrrolidinyl or thiomorpholinyl said $Het^2$ substituted with one or where possible two or more substituents selected from $C_{1-4}$alkyl- substituted with one or more substituents selected from $NR^{27}R^{28}$, $C_{1-4}$alkylsulfonyl, aminocarbonyloxy-, aminocarbonyl- and mono- or di($C_{1-4}$alkyl)aminocarbonyl-; or $C_{1-4}$alkyloxy- optionally substituted with $C_{1-4}$alkyloxy-; or $C_{1-4}$alkyloxycarbonyl optionally substituted with one or more substituents selected from hydroxy, $C_{1-4}$alkyloxy- and $C_{1-4}$alkylsulfonyl-; or $C_{1-4}$alkylcarbonyl optionally substituted with one or more substituents selected from hydroxy-, $C_{1-4}$alkyloxy- and $C_{1-4}$alkylsulfonyl-; or $Het^2$ represents 1,1-dioxothiomorpholinyl optionally substituted with $C_{1-4}$alkyl-optionally substituted with one or more substituents selected from $NR^{27}R^{28}$, $C_{1-4}$alkylsulfonyl, aminocarbonyloxy-, aminocarbonyl- and mono- or di($C_{1-4}$alkyl)aminocarbonyl-; or $C_{1-4}$alkyloxy- optionally substituted with $C_{1-4}$alkyloxy-; or $C_{1-4}$alkyloxycarbonyl optionally substituted with one or more substituents selected from hydroxy, $C_{1-4}$alkyloxy- and $C_{1-4}$alkylsulfonyl-; or $C_{1-4}$alkylcarbonyl optionally substituted with one or more substituents selected from hydroxy-, $C_{1-4}$alkyloxy- and $C_{1-4}$alkylsulfonyl-.

2. A compound according to claim 1 wherein;

Z represents NH;

Y represents —$C_{3-9}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-6}$alkyl—CO—NH—, —$C_{1-6}$alkyl-NH—CO—, —$C_{1-2}$alkyl-$NR^{23}$—CO—$CR^{16}R^{17}$—NH—, —$C_{1-2}$alkyl-$NR^{21}$—$CH_2$—CO—NH—$C_{1-3}$alkyl or $C_{1-3}$alkyl-NH—CO-$Het^{20}$-;

$X^1$ represents O, —O—$C_{1-2}$alkyl-, $NR^{11}$, or —$NR^{11}$—$C_{1-2}$alkyl-;

$X^2$ represents a direct bond, —$C_{1-2}$alkyl-, CO—$C_{1-2}$alkyl or $NR^{12}$—$C_{1-2}$alkyl-;

$R^1$ represents hydrogen, cyano, halo or hydroxy;

$R^2$ represents hydrogen, halo, cyano, $C_{2-6}$alkynyl, hydroxy, hydroxycarbonyl, $C_{1-4}$alkyloxycarbonyl- or $Het^1$;

$R^3$ represents hydrogen, cyano, halo, hydroxy, formyl, $C_{1-6}$alkyloxy or $C_{1-6}$alkyloxy- substituted with halo;

$R^4$ represents $Ar^4$—$C_{1-4}$alkyloxy, $C_{1-4}$alkyloxy-, or $C_{1-4}$alkyloxy- substituted with one or where possible two or more substituents selected from hydroxy, $C_{1-4}$alkyloxy-, $C_{1-4}$alkyloxy-$C_{1-4}$alkyloxy, $NR^7R^8$ or $Het^2$;

$R^7$ represents hydrogen, hydroxy$C_{1-4}$alkyl- or $C_{1-4}$alkyl;

$R^8$ represents $C_{1-4}$alkyloxycarbonyl or $C_{1-4}$alkyl- substituted with one or more substituents selected from $C_{1-4}$alkylsulfonyl-, $C_{1-4}$alkylcarbonyloxy or $NR^{25}R^{26}$;

$R^{11}$ represents hydrogen, $C_{1-4}$alkyloxycarbonyl or $C_{1-4}$alkyl;

$R^{12}$ represents hydrogen or $C_{1-4}$alkyl;

$R^{13}$ represents $C_{1-6}$alkyloxycarbonyl optionally substituted with phenyl or $R^{13}$ represents $Ar^6$-sulfonyl or $Het^{24}$-$C_{1-4}$alkylcarbonyl;

$R^{14}$ and $R^{15}$ each independently represent hydrogen or $C_{1-4}$alkyl;

$R^{16}$ and $R^{17}$ each independently represent hydrogen or $C_{1-4}$alkyl optionally substituted with $C_{3-6}$cycloalkyl or $R^{16}$ and $R^{17}$ taken together with the carbon atom to which they are attached form a $C_{3-6}$cycloalkyl;

$R^{21}$ represents hydrogen;

$R^{23}$ represents $C_{1-4}$alkyl optionally substituted with hydroxy-, $C_{1-4}$alkyloxy- or $Het^{25}$; $R^{23}$ may also represent hydrogen when $R^{16}$ and $R^{17}$ taken together with the carbon atom to which they are attached form a $C_{3-6}$cycloalkyl;

$R^{25}$ and $R^{26}$ each independently represent hydrogen, $C_{1-4}$alkyl, $C_{1-4}$alkylsulfonyl, $C_{1-4}$alkyloxycarbonyl or $C_{1-4}$alkylcarbonyl;

$R^{27}$ and $R^{28}$ each independently represent hydrogen, $C_{1-4}$alkyl, $C_{1-4}$alkylsulfonyl, $C_{1-4}$alkyloxycarbonyl or $C_{1-4}$alkylcarbonyl;

$Het^1$ represents 2-bora-1,3-dioxolanyl- optionally substituted with one or where possible two, three, four or more substituents selected from amino, $C_{1-4}$alkyl, hydroxy-$C_{1-4}$alkyl-, phenyl, phenyl-$C_{1-4}$alkyl, $C_{1-4}$alkyloxy$C_{1-4}$alkyl-, mono- or di($C_{1-4}$alkyl)amino- or aminocarbonyl-;

$Het^2$ represents 1,1-dioxothiomorpholinyl optionally substituted with $C_{1-4}$alkyloxycarbonyl or $C_{1-4}$alkyl-$NR^{27}R^{28}$; or $Het^2$ represents piperidinyl or piperazinyl substituted with $C_{1-4}$alkyloxycarbonyl or —$C_{1-4}$alkyl-$NR^{27}R^{28}$;

$Het^{20}$ represents pyrrolidinyl, 2-pyrrolidinonyl, piperidinyl or hydroxy-pyrrolidinyl;

$Het^{25}$ represents a heterocycle selected from morpholinyl or piperazinyl wherein said heterocycle is optionally substituted with $C_{1-4}$alkyl, hydroxy-$C_{1-4}$alkyl, $C_{1-4}$alkyloxy-$C_{1-4}$alkyl or polyhydroxy-$C_{1-4}$alkyl; or $Ar^4$, $Ar^5$ or $Ar^6$ each independently represents phenyl optionally substituted with nitro, cyano, hydroxy, hydroxy$C_{1-4}$alkyl, $C_{1-4}$alkyl or $C_{1-4}$alkyloxy;

further characterised in that either
Y represents —$C_{1-2}$alkyl-$NR^{23}$—CO—$CR^{16}R^{17}$—NH—; or
$R^4$ represents $C_{1-4}$alkyloxy substituted with at least one substituent selected from $C_{1-4}$alkyloxy-$C_{1-4}$alkyloxy-, $NR^7R^8$ or $Het^2$.

3. A pharmaceutical composition comprising a pharmaceutically acceptable carrier and, as active ingredient, an effective kinase inhibitory amount of a compound as described in claim 1.

4. A compound according to claim 2 wherein;
Z represents NH;
Y represents —$C_{3-9}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-6}$alkyl-CO—NH—, —$C_{1-6}$alkyl-NH—CO—, —$C_{1-2}$alkyl-$NR^{23}$—CO—$CR^{16}R^{17}$—NH—, —$C_{1-2}$alkyl-$NR^{21}$—$CH_2$—CO—NH—$C_{1-3}$alkyl- or $C_{1-3}$alkyl-NH—CO-$Het^{20}$-;
$X^1$ represents O, —O—$C_{1-2}$alkyl-, $NR^{11}$, or —$NR^{11}$—$C_{1-2}$ alkyl-;
$X^2$ represents a direct bond, —$C_{1-2}$alkyl-, CO—$C_{1-2}$alkyl or $NR^{12}$—$C_{1-2}$alkyl-;
$R^1$ represents hydrogen or halo;
$R^2$ represents hydrogen, halo, $C_{2-6}$alkynyl, cyano or $Het^1$;
$R^3$ represents hydrogen;
$R^4$ represents $Ar^4$—$C_{1-4}$alkyloxy, $C_{1-4}$alkyloxy-, or $C_{1-4}$alkyloxy- substituted with one or where possible two or more substituents selected from hydroxy, $C_{1-4}$alkyloxy-, $C_{1-4}$alkyloxy-$C_{1-4}$alkyloxy, $NR^7R^8$ or $Het^2$;
$R^7$ represents hydrogen or $C_{1-4}$alkyl;
$R^8$ represents $C_{1-4}$alkyloxycarbonyl or $C_{1-4}$alkyl- substituted with one or more substituents selected from $C_{1-4}$alkylsulfonyl-, $C_{1-4}$alkylcarbonyloxy or $NR^{25}R^{26}$;
$R^{11}$ represents hydrogen or $C_{1-4}$alkyl;
$R^{12}$ represents hydrogen or $C_{1-4}$alkyl;
$R^{13}$ represents $Ar^6$-sulfonyl or $C_{1-6}$alkyloxycarbonyl optionally substituted with phenyl;
$R^{14}$ and $R^{15}$ represent hydrogen;
$R^{16}$ and $R^{17}$ each independently represent hydrogen or $C_{1-4}$alkyl optionally substituted with $C_{3-6}$cycloalkyl or $R^{16}$ and $R^{17}$ taken together with the carbon atom to which they are attached form a $C_{3-6}$cycloalkyl;
$R^{21}$ represents hydrogen;

$R^{23}$ represents $C_{1-4}$alkyl optionally substituted with hydroxy-, $C_{1-4}$alkyloxy- or $Het^{25}$; $R^{23}$ may also represent hydrogen when $R^{16}$ and $R^{17}$ taken together with the carbon atom to which they are attached form a $C_{3-6}$cycloalkyl;
$R^{25}$ and $R^{26}$ each independently represent hydrogen or $C_{1-4}$alkylcarbonyl;
$R^{27}$ and $R^{28}$ each independently represent hydrogen or $C_{1-4}$alkylcarbonyl;
$Het^1$ represents 2-bora-1,3-dioxolanyl-;
$Het^2$ represents 1,1-dioxothiomorpholinyl, piperidinyl or piperazinyl wherein said $Het^2$ is optionally substituted with $C_{1-4}$alkyloxycarbonyl or —$C_{1-4}$alkyl-$NR^{27}R^{28}$;
$Het^{20}$ represents pyrrolidinyl;
$Het^{25}$ represents a heterocycle selected from morpholinyl or piperazinyl wherein said heterocycle is optionally substituted with $C_{1-4}$alkyl, hydroxy-$C_{1-4}$alkyl, $C_{1-4}$alkyloxy-$C_{1-4}$alkyl or polyhydroxy-$C_{1-4}$alkyl;
$Ar^4$ represents phenyl;
$Ar^5$ represents phenyl; or
$Ar^6$ represents phenyl optionally substituted with nitro;
further characterised in that either
Y represents —$C_{1-2}$alkyl-$NR^{23}$—CO—$CR^{16}R^{17}$—NH—; or
$R^4$ represents $C_{1-4}$alkyloxy substituted with at least one substituent selected from $C_{1-4}$alkyloxy-$C_{1-4}$alkyloxy-, $NR^7R^8$ or $Het^2$.

5. A compound according to claim 2 wherein;
Z represents NH;
Y represents —$C_{3-9}$alkyl-,—$C_{1-5}$alkyl-$NR^{13}$—$C_{1-5}$alkyl-, —$C_{1-5}$alkyl-$NR^{14}$—CO—$C_{1-5}$alkyl-, —$C_{1-2}$alkyl-$NR^{21}$—$H_2$—CO—NH—$C_{1-3}$alkyl- or —$C_{1-2}$alkyl-$NR^{23}$—CO—$CR^{16}R^{17}$—NH—;
$X^1$ represents O or —O—$C_{1-2}$alkyl-;
$X^2$ represents a direct bond, $C_{1-2}$alkyl, —CO—$C_{1-2}$alkyl or $NR^{12}$—$C_{1-2}$alkyl;
$R^1$ represents hydrogen or halo;
$R^2$ represents halo, acetylene or $Het^1$;
$R^4$ represents $Ar^4$—$C_{1-4}$alkyloxy-, $C_{1-4}$alkyloxy- or $C_{1-4}$alkyloxy substituted with one or where possible two or more substituents selected from $Het^2$, $NR^7R^8$, hydroxy and $C_{1-4}$alkyloxy—$C_{1-4}$alkylox-;
$R^7$ represents hydrogen or $C_{1-4}$alkyl;
$R^8$ represents $C_{1-4}$alkyl substituted with $NR^{25}R^{26}$ or $C_{1-4}$alkylsulfonyl;
$R^{12}$ represents hydrogen or $C_{1-4}$alkyl-;
$R^{13}$ represents $Ar^6$-sulfonyl or $C_{1-6}$alkyloxycarbonyl optionally substituted with phenyl;
$R^{16}$ and $R^{17}$ represents hydrogen, $C_{1-4}$alkyl or $R^{16}$ and $R^{17}$ taken together with the carbon atom to which they are attached from a $C_{3-6}$cycloalkyl;
$R^{23}$ represents hydrogen or $C_{1-4}$alkyl;
$R^{25}$ and $R^{26}$ each independently represent hydrogen or $C_{1-4}$alkylcarbonyl;
$R^{27}$ and $R^{28}$ each independently represent hydrogen or $C_{1-4}$alkylcarbonyl;
$Het^1$ represents 2-bora-1,3-dioxolanyl;
$Het^2$ represents piperidinyl, piperazinyl, morpholinyl, thiomorpholinyl or 1,1-dioxothiomorpholinyl wherein said $Het^2$ is optionally substituted with $C_{1-4}$alkyloxycarbonyl or $NR^{27}R^{28}$—$C_{1-4}$alkyl;
$Ar^4$ represents phenyl;
$Ar^5$ represents phenyl; or
$Ar^6$ represents phenyl optionally substituted with nitro.

6. A compound according to claim 2 wherein;
Z represents NH;
Y represents —$C_{3-9}$alkyl-,—$C_{1-5}$alkyl-$NR^{13}$—$C_{1-5}$alkyl- or —$C_{1-2}$alkyl-$NR^{23}$—CO—$CR^{16}R^{17}$—NH—;
$X^1$ represents O; $X^2$ represents a direct bond or $NR^{12}$—$C_{1-2}$alkyl-;
$R^1$ represents hydrogen; $R^2$ represents halo or $Het^1$; $R^3$ represents hydrogen;
$R^4$ represents $Ar^4$—$C_{1-4}$alkyloxy-, $C_{1-4}$alkyloxy- or $C_{1-4}$alkyloxy substituted with $C_{1-4}$alkyloxy-$C_{1-4}$alkyloxy-;
$R^{12}$ represents hydrogen or $C_{1-4}$alkyl-;
$R^{13}$ represents $Ar^6$-sulfonyl or $C_{1-6}$alkyloxycarbonyl optionally substituted with phenyl;
$R^{16}$ and $R^{17}$ taken together with the carbon atom to which they are attached from a $C_{3-6}$cycloalkyl;
$R^{23}$ represents hydrogen or $C_{1-4}$alkyl;
$Het^1$ represents 2-bora-1,3-dioxolanyl;
$Ar^4$ represents phenyl; $Ar^5$ represents phenyl;
$Ar^6$ represents phenyl optionally substituted with nitro.

7. A compound according to claim 2 wherein $X^2$ substituent is at position 2', the $R^1$ substituent represents hydrogen or halo and is at position 4', the $R^2$ substituent represents halo and is at position 5', the $R^3$ substituent is at position 2 and the $R^4$ substituent at position 7 of the structure of formula (I).

8. A compound according to claim 1 wherein;
Z represents NH;
Y represents —$C_{3-9}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-6}$alkyl-CO—NH—, —$C_{1-6}$alkyl-NH—CO—, —$C_{1-2}$alkyl-$NR^{23}$—CO—$CR^{16}R^{17}$—NH—, —$C_{1-2}$alkyl-$NR^{21}$—$CH_2$—CO—NH—$C_{1-3}$alkyl or $C_{1-3}$alkyl-NH—CO-$Het^{20}$-;
$X^1$ represents a O, —O—$C_{1-2}$alkyl-, $NR^{11}$, or —$NR^{11}$—$C_{1-2}$alkyl-;
$X^2$ represents a direct bond, —$C_{1-2}$alkyl-, CO—$C_{1-2}$alkyl or $NR^{12}$—$C_{1-2}$alkyl-;
$R^1$ represents hydrogen or halo;
$R^2$ represents hydrogen, halo, $C_{2-6}$alkynyl, cyano or $Het^1$;
$R^3$ represents hydrogen;
$R^4$ represents $Ar^4$—$C_{1-4}$alkyloxy, $C_{1-4}$alkyloxy-, or $C_{1-4}$alkyloxy- substituted with one or where possible two or more substituents selected from hydroxy, $C_{1-4}$alkyloxy-, $C_{1-4}$alkyloxy-$C_{1-4}$alkyloxy, $NR^7R^8$ or $Het^2$;
$R^7$ represents hydrogen or $C_{1-4}$alkyl;
$R^8$ represents $C_{1-4}$alkyloxycarbonyl or $C_{1-4}$alkyl- substituted with one or more substituents selected from $C_{1-4}$alkylsulfonyl-, $C_{1-4}$alkylcarbonyloxy or $NR^{25}R^{26}$;
$R^{11}$ represents hydrogen or $C_{1-4}$alkyl;
$R^{12}$ represents hydrogen or $C_{1-4}$alkyl;
$R^{13}$ represents $Ar^6$-sulfonyl or $C_{1-6}$alkyloxycarbonyl optionally substituted with phenyl;
$R^{14}$ and $R^{15}$ represent hydrogen;
$R^{16}$ and $R^{17}$ each independently represent hydrogen or $C_{1-4}$alkyl optionally substituted with $C_{3-6}$cycloalkyl or $R^{16}$ and $R^{17}$ taken together with the carbon atom to which they are attached form a $C_{3-6}$cycloalkyl;
$R^{21}$ represents hydrogen;
$R^{23}$ represents $C_{1-4}$alkyl optionally substituted with hydroxy-, $C_{1-4}$alkyloxy- or $Het^{25}$; $R^{23}$ may also represent hydrogen when $R^{16}$ and $R^{17}$ taken together with the carbon atom to which they are attached form a $C_{3-6}$cycloalkyl;
$R^{25}$ and $R^{26}$ each independently represent hydrogen or $C_{1-4}$alkylcarbonyl;
$R^{27}$ and $R^{28}$ each independently represent hydrogen or $C_{1-4}$alkylcarbonyl;
$Het^1$ represents 2-bora-1,3-dioxolanyl-;
$Het^2$ represents 1,1-dioxothiomorpholinyl, piperidinyl or piperazinyl wherein said $Het^2$ is optionally substituted with $C_{1-4}$alkyloxycarbonyl or —$C_{1-4}$alkyl-$NR^{27}R^{28}$;
$Het^{20}$ represents pyrrolidinyl;
$Het^{25}$ represents a heterocycle selected from morpholinyl or piperazinyl wherein said heterocycle is optionally substituted with $C_{1-4}$alkyl, hydroxy-$C_{1-4}$alkyl, $C_{1-4}$alkyloxy-$C_{1-4}$alkyl or polyhydroxy-$C_{1-4}$alkyl;
$Ar^4$ represents phenyl;
$Ar^5$ represents phenyl; or
$Ar^6$ represents phenyl optionally substituted with nitro;
further characterised in that either
Y represents —$C_{1-2}$alkyl-$NR^{23}$—CO—$CR^{16}R^{17}$—NH—; or
$R^4$ represents $C_{1-4}$alkyloxy substituted with at least one substituent selected from $C_{1-4}$alkyloxy-$C_{1-4}$alkyloxy-, $NR^7R^8$ or $Het^2$.

9. A compound according to claim 8 wherein;
Z represents NH;
Y represents —$C_{3-9}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-2}$alkyl-$NR^{21}$—$H_2$—CO—NH—$C_{1-3}$alkyl- or —$C_{1-2}$alkyl-$NR^{23}$—CO—$CR^{16}R^{17}$—NH—;
$X^1$ represents O or —O—$C_{1-2}$alkyl-;
$X^2$ represents a direct bond, $C_{1-2}$alkyl, —CO—$C_{1-2}$alkyl or $NR^{12}$—$C_{1-2}$alkyl;
$R^1$ represents hydrogen or halo;
$R^2$ represents halo, acetylene or $Het^1$;
$R^3$ represents hydrogen;
$R^4$ represents $Ar^4$—$C_{1-4}$alkyloxy-, $C_{1-4}$alkyloxy- or $C_{1-4}$alkyloxy substituted with one or where possible two or more substituents selected from $Het^2$, $NR^7R^8$, hydroxy and $C_{1-4}$alkyloxy-$C_{14}$alkyloxy-;
$R^7$ represents hydrogen or $C_{1-4}$alkyl;
$R^8$ represents $C_{1-4}$alkyl substituted with $NR^{25}R^{26}$ or $C_{1-4}$alkylsulfonyl;
$R^{12}$ represents hydrogen or $C_{1-4}$alkyl-;
$R^{13}$ represents $Ar^6$-sulfonyl or $C_{1-6}$alkyloxycarbonyl optionally substituted with phenyl;
$R^{16}$ and $R^{17}$ represents hydrogen, $C_{1-4}$alkyl or le and $R^{17}$ taken together with the carbon atom to which they are attached from a $C_{3-6}$cycloalkyl;
$R^{23}$ represents hydrogen or $C_{1-4}$alkyl;
$R^{25}$ and $R^{26}$ each independently represent hydrogen or $C_{1-4}$alkylcarbonyl;
$R^{27}$ and $R^{28}$ each independently represent hydrogen or $C_{1-4}$alkylcarbonyl;
$Het^1$ represents 2-bora-1,3-dioxolanyl;
$Het^2$ represents piperidinyl, piperazinyl, morpholinyl, thiomorpholinyl or 1,1-dioxothiomorpholinyl wherein said $Het^2$ is optionally substituted with $C_{1-4}$alkyloxycarbonyl or $NR^{27}R^{28}$—$C_{1-4}$alkyl;
$Ar^4$ represents phenyl;
$Ar^5$ represents phenyl; or
$Ar^6$ represents phenyl optionally substituted with nitro.

10. A compound according to claim 8 wherein;
Z represents NH;
Y represents —$C_{3-9}$alkyl-,—$C_{1-5}$alkyl-$NR^{13}$—$C_{1-5}$alkyl- or —$C_{1-2}$alkyl-$NR^{23}$—CO—$CR^{16}R^{17}$—NH—;
$X^1$ represents O; $X^2$ represents a direct bond or $NR^{12}$—$C_{1-2}$alkyl-;
$R^1$ represents hydrogen; $R^2$ represents halo or $Het^1$; $R^3$ represents hydrogen;
$R^4$ represents $Ar^4$—$C_{1-4}$alkyloxy-, $C_{1-4}$alkyloxy- or $C_{1-4}$alkyloxy substituted with $C_4$alkyloxy —$C_{1-4}$alkyloxy-;

$R^{12}$ represents hydrogen or $C_{1-4}$alkyl-;

$R^{13}$ represents $Ar^6$-sulfonyl or $C_{1-6}$alkyloxycarbonyl optionally substituted with phenyl;

$R^{16}$ and $R^{17}$ taken together with the carbon atom to which they are attached from a $C_{3-6}$cycloalkyl;

$R^{23}$ represents hydrogen or $C_{1-4}$alkyl;

$Het^1$ represents 2-bora-1,3-dioxolanyl;

$Ar^4$ represents phenyl; $Ar^5$ represents phenyl;

$Ar^6$ represents phenyl optionally substituted with nitro.

11. A compound according to claim 3 wherein $X^2$ substituent is at position 2', the $R^1$ substituent represents hydrogen or halo and is at position 4', the $R^2$ substituent represents halo and is at position 5', the $R^3$ substituent is at position 2 and the $R^4$ substituent at position 7 of the structure of formula (I).

12. A pharmaceutical composition comprising a pharmaceutically acceptable carrier and, as active ingredient, an effective kinase inhibitory amount of a compound as described in claim 8.

13. A compound according to claim 1 wherein;

Z represents NH;

Y represents —$C_{3-9}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-2}$alkyl-$NR^{21}$—H$_2$—CO—NH—$C_{1-3}$alkyl- or —$C_{1-2}$alkyl-$NR^{23}$—CO—$CR^{16}R^{17}$—NH—;

$X^1$ represents O or —O—$C_{1-2}$alkyl-;

$X^2$ represents a direct bond, $C_{1-2}$alkyl, —CO—$C_{1-2}$alkyl or $NR^{12}$—$C_{1-2}$alkyl;

$R^1$ represents hydrogen or halo;

$R^2$ represents halo, acetylene or $Het^1$;

$R^3$ represents hydrogen;

$R^4$ represents $Ar^4$—$C_{1-4}$alkyloxy-, $C_{1-4}$alkyloxy- or $C_{1-4}$alkyloxy substituted with one or where possible two or more substituents selected from $Het^2$, $NR^7R^8$, hydroxy and $C_{1-4}$alkyloxy-$C_{1-4}$alkylox-;

$R^7$ represents hydrogen or $C_{1-4}$alkyl;

$R^8$ represents $C_{1-4}$alkyl substituted with $NR^{25}R^{26}$ or $C_{1-4}$alkylsulfonyl;

$R^{12}$ represents hydrogen or $C_{1-4}$alkyl-;

$R^{13}$ represents $Ar^6$-sulfonyl or $C_{1-6}$alkyloxycarbonyl optionally substituted with phenyl;

$R^{16}$ and $R^{17}$ represents hydrogen, $C_{1-4}$alkyl or $R^{16}$ and $R^{17}$ taken together with the carbon atom to which they are attached from a $C_{3-6}$cycloalkyl;

$R^{23}$ represents hydrogen or $C_{1-4}$alkyl;

$R^{25}$ and $R^{26}$ each independently represent hydrogen or $C_{1-4}$alkylcarbonyl;

$R^{27}$ and $R^{28}$ each independently represent hydrogen or $C_{1-4}$alkylcarbonyl;

$Het^1$ represents 2-bora-1,3-dioxolanyl;

$Het^2$ represents piperidinyl, piperazinyl, morpholinyl, thiomorpholinyl or 1,1-dioxothiomorpholinyl wherein said $Het^2$ is optionally substituted with $C_{1-4}$alkyloxycarbonyl or $NR^{27}R^{28}$—$C_{1-4}$alkyl;

$Ar^4$ represents phenyl;

$Ar^5$ represents phenyl; or $Ar^6$ represents phenyl optionally substituted with nitro.

14. A compound according to claim 4 wherein $X^2$ substituent is at position 2', the $R^1$ substituent represents hydrogen or halo and is at position 4', the $R^2$ substituent represents halo and is at position 5', the $R^3$ substituent is at position 2 and the $R^4$ substituent at position 7 of the structure of formula (I).

15. A pharmaceutical composition comprising a pharmaceutically acceptable carrier and, as active ingredient, an effective kinase inhibitory amount of a compound as described in claim 13.

16. A compound according to claim 1 wherein;

Z represents NH;

Y represents —$C_{3-9}$alkyl-, —$C_{1-5}$alkyl-$NR^{13}$—$C_{1-5}$alkyl- or —$C_{1-2}$alkyl-$NR^{23}$—CO—$CR^{16}R^{17}$—NH—;

$X^1$ represents O; $X^2$ represents a direct bond or $NR^{12}$—$C_{1-2}$alkyl-;

$R^1$ represents hydrogen; $R^2$ represents halo or $Het^1$; $R^3$ represents hydrogen;

$R^4$ represents $Ar^4$—$C_{1-4}$alkyloxy-, $C_{1-4}$alkyloxy- or $C_{1-4}$alkyloxy substituted with $C_{1-4}$alkyloxy-$C_{1-4}$alkyloxy-;

$R^{12}$ represents hydrogen or $C_{1-4}$alkyl-;

$R^{13}$ represents $Ar^6$-sulfonyl or $C_{1-6}$alkyloxycarbonyl optionally substituted with phenyl;

$R^{16}$ and $R^{17}$ taken together with the carbon atom to which they are attached from a $C_{3-6}$cycloalkyl;

$R^{23}$ represents hydrogen or $C_{1-4}$alkyl;

$Het^1$ represents 2-bora-1,3-dioxolanyl;

$Ar^4$ represents phenyl; $Ar^5$ represents phenyl;

$Ar^6$ represents phenyl optionally substituted with nitro.

17. A compound according to claim 16 wherein $X^2$ substituent is at position 2', the $R^1$ substituent represents hydrogen or halo and is at position 4', the $R^2$ substituent represents halo and is at position 5', the $R^3$ substituent is at position 2 and the $R^4$ substituent at position 7 of the structure of formula (I).

18. A pharmaceutical composition comprising a pharmaceutically acceptable carrier and, as active ingredient, an effective kinase inhibitory amount of a compound as described in claim 2.

19. A pharmaceutical composition comprising a pharmaceutically acceptable carrier and, as active ingredient, an effective kinase inhibitory amount of a compound as described in claim 16.

20. A compound according to claim 1 wherein $X^2$ substituent is at position 2', the $R^1$ substituent represents hydrogen or halo and is at position 4', the $R^2$ substituent represents halo and is at position 5', the $R^3$ substituent is at position 2 and the $R^4$ substituent at position 7 of the structure of formula (I).

21. A pharmaceutical composition comprising a pharmaceutically acceptable carrier and, as active ingredient, an effective kinase inhibitory amount of a compound as described in claim 20.

22. A compound according to claim 1, wherein

Z represents NH;

Y represents —$C_{3-9}$alkyl-,—$C_{1-5}$alkyl-$NR^{13}$—$C_{1-5}$alkyl-, —$C_{1-2}$alkyl-$NR^{21}$—CH$_2$—CO-NH—$C_{1-3}$alkyl-, $C_{1-6}$alkyl-NH—CO— or .$C_{1-2}$alkyl-; $NR^{23}$—CO—$CR^{16}R^{17}$—NH—;

$X^1$ represents O or —O—$C_{1-2}$alkyl-;

$X^2$ represents a direct bond, $C_{1-2}$alkyl, —CO—$C_{1-2}$alkyl or $NR^{12}$—$C_{1-2}$alkyl $R^1$ represents hydrogen, cyano or halo;

$R^2$ represents halo, $C_{2-6}$alkynyl, cyano or $Het^1$;

$R^3$ represents hydrogen;

$R^4$ represents $Ar^4$—$C_{1-4}$alkyloxy-, $C_{1-4}$alkyloxy- or $C_{1-4}$alkyloxy substituted with one or where possible two or more substituents selected from $Het^2$, $NR^7R^8$, hydroxy and $C_{1-4}$alkyloxy-$C_{1-4}$alkyloxy-;

$R^7$ represents hydrogen, hydroxy-$C_{1-4}$alkyl- or $C_{1-4}$alkyl;

$R^8$ represents $C_{1-4}$alkylcarbonyl , $C_{1-4}$alkyloxycarbonyl or $C_{1-4}$alkyl substituted with hydroxy-$C_{1-4}$alkyloxy-, $NR^{25}R^{26}$, $C_{1-4}$alkylcarbonyloxy- or $C_{1-4}$alkylsulfonyl;

$R^{12}$ represents hydrogen or $C_{1-4}$alkyl-;

$R^{13}$ represents $Ar^6$-sulfonyl or $C_{1-6}$alkyloxycarbonyl optionally substituted with phenyl;

$R^{16}$ and $R^{17}$ each independently represents hydrogen, $C_{1-4}$alkyl or $R^{16}$ and $R^{17}$ taken together with the carbon atom to which they are attached from a $C_{3-6}$cycloalkyl;

$R^{23}$ represents $C_{1-4}$alkyl optionally substituted with Het$^{25}$;

$R^{23}$ may also represent hydrogen when $R^{16}$ and $R^{17}$ taken together with the carbon atom to which they are attached form a $C_{3-6}$cycloalkyl;

$R^{25}$ and $R^{26}$ each independently represent hydrogen or $C_{1-4}$alkylcarbonyl;

$R^{27}$ and $R^{28}$ each independently represent hydrogen or $C_{1-4}$alkylcarbonyl;

Het$^{1}$ represents 2-bora-1,3-dioxolanyl;

Het$^{2}$ represents piperidinyl, piperazinyl, morpholinyl, thiomorpholinyl or 1,1-dioxothiomorpholinyl wherein said Het$^{2}$ is optionally substituted with $C_{1-4}$alkyloxycarbonyl or NR$^{27}$R$^{28}$—$C_{1-4}$alkyl;

Het$^{25}$ represents morpholinyl;

Ar$^{4}$ represents phenyl;

Ar$^{5}$ represents phenyl;

Ar$^{6}$ represents phenyl optionally substituted with nitro.

23. A compound according to claim 1, wherein

Z represents NH;

Y represents —$C_{3-9}$alkyl-, —$C_{2-9}$alkenyl-, —$C_{1-5}$alkyl-oxy-$C_{1-5}$alkyl-, —$C_{1-5}$alkyl-NR$^{13}$—$C_{1-5}$alkyl-, —$C_{1-5}$alkyl-NR$^{14}$—CO—$C_{1-5}$alkyl-, —$C_{1-6}$alkyl-NH—CO—, —NH—CO—$C_{1-6}$alkyl-, —CO—$C_{1-7}$alkyl-CO—, $C_{1-6}$alkyl-CO—$C_{1-6}$alkyl, —$C_{1-2}$alkyl-NR$^{23}$—CO—CR$^{16}$R$^{17}$—NH—, —$C_{1-2}$alkyl—CO—NH—CR$^{18}$R$^{19}$—CO—, —$C_{1-2}$alkyl-CO—NR$^{20}$—$C_{1-3}$alkyl-NR$^{21}$—CH$_2$—CO—NH—$C_{1-3}$alkyl-, —NR$^{22}$—CO—$C_{1-3}$alkyl-NH—, —$C_{1-3}$alkyl-NH—CO-Het$^{20}$—, $C_{1-2}$alkyl-CO-Het$^{21}$—CO—, or -Het$^{22}$—CH$_2$—CO-NH—$C_{1-3}$alkyl-, $X^1$ represents O, —O—$C_{1-2}$alkyl-, —O—N=CH—, NR$^{11}$ or —NR$^{11}$—$C_{1-2}$alkyl-, $X^2$ represents a direct bond, $C_{1-2}$alkyl, O, —O—$C_{1-2}$alkyl-, CO, —CO—$C_{1-2}$alkyl-, —O—N=CH—, NR$^{12}$ or NR$^{12}$—$C_{1-2}$alkyl-;

$R^1$ represents hydrogen, cyano, halo or hydroxy;

$R^2$ represents hydrogen, cyano, halo, hydroxy, hydroxycarbonyl-, $C_{1-4}$alkyloxycarbonyl-, Het$^{16}$-carbonyl-, $C_{1-4}$alkyl-, $C_{2-6}$alkynyl-, Ar$^5$, Het$^1$ or dihydroxyborane;

$R^3$ represents hydrogen, cyano, halo, hydroxy, formyl, $C_{1-6}$alkoxy-, $C_{1-6}$alkyl-, $C_{1-6}$alkoxy- substituted with halo, or $R^3$ represents $C_{1-4}$alkyl substituted with one or where possible two or more substituents selected from hydroxy or halo;

$R^4$ represents Ar$^4$—$C_{1-4}$alkyloxy-, $C_{1-4}$alkyloxy- or $R^4$ represents $C_{1-4}$alkyloxy substituted with one or where possible two or more substituents selected from hydroxy-, halo, $C_{1-4}$alkyloxy-, $C_{1-4}$alkyloxy-$C_{1-4}$alkyloxy-, NR$^{37}$R$^{38}$-carbonyloxy-, Het$^5$-carbonyloxy-, NR$^7$R$^8$, NR$^9$R$^{10}$-carbonyl-, Het$^3$-carbonyl-, Het$^{13}$-oxy- or Het$^2$-;

$R^7$ represents hydrogen or $C_{1-4}$alkyl;

$R^8$ represents $C_{3-6}$cycloalkyl, Het$^6$-carbonyl-, Het$^7$-aminocarbonyl-, Het$^8$, Het$^9$-oxycarbonyl-, Het$^{10}$-sulfonyl-, mono- or di($C_{1-4}$alkyl)aminocarbonyl-, mono- or di($C_{1-4}$alkyl)aminocarbonyl substituted with $C_{1-4}$alkylsulfonyl-, or $C_{1-4}$alkylcarbonyl optionally substituted with one or more substituents selected from $C_{1-4}$alkylsulfonyl, hydroxy- and $C_{1-4}$alkyloxy-, or $R^8$ represents $C_{1-4}$alkyl substituted with one or more substituents selected from $C_{1-4}$alkylsulfonyl-, NR$^{25}$R$^{26}$, aminocarbonyloxy-, aminocarbonyl-, $C_{1-4}$alyloxy-$C_{1-4}$alkyloxy-, and Het$^{11}$;

$R^9$ represents hydrogen or $C_{1-4}$alkyl-;

$R^{10}$ represents Het$^4$ or $C_{1-4}$alkyl- substituted with $C_{1-4}$alkylsulfonyl-;

$R^{11}$ represents hydrogen, $C_{14}$alkyl- or $C_{14}$alkyl-oxy-carbonyl-;

$R^{12}$ represents hydrogen, $C_{1-4}$alkyl-, $C_{1-6}$alkyloxycarbonyl- or $C_{1-6}$alkyloxycarbonyl- substituted with phenyl;

$R^{13}$ represents hydrogen, Het$^{14}$—$C_{1-4}$alkyl, $C_{1-6}$alkyloxycarbonyl optionally substituted with phenyl or $R^{13}$ represents Ar$^6$-sulfonyl or Het$^{24}$—$C_{1-4}$alkylcarbonyl;

$R^{14}$ and $R^{15}$ are each independently selected from hydrogen, $C_{14}$alkyl, Het$^{15}$—$C_{1-4}$alkyl- or $C_{1-4}$alkyloxy$C_{1-4}$alkyl-;

$R^{16}$ and $R^{17}$ each independently represents hydrogen, $C_{1-4}$alkyl or $C_{1-4}$alalkyl substituted with hydroxy- or phenyl; or $R^{16}$ and $R^{17}$ taken together with the carbon atom to which they are attached form a $C_{3-6}$cycloalkyl;

$R^{18}$ represents hydrogen or $C_{1-4}$alkyl optionally substituted with hydroxy or phenyl;

$R^{19}$ represents hydrogen or $C_{1-4}$alkyl;

$R^{20}$ represents hydrogen or $C_{1-4}$alkyl;

$R^{21}$ represents hydrogen, $C_{1-4}$alkyl, Het$^{23}$—$C_{1-4}$alkylcarbonyl- or $R^{21}$ represents mono- or di($C_{1-4}$alkyl)amino-$C_{1-4}$alkylcarbonyl- optionally substituted with hydroxy, pyrimidinyl, dimethylamine or $C_{1-4}$alkyloxy;

$R^{22}$ represents hydrogen or $C_{1-4}$alkyl optionally substituted with hydroxy or $C_{1-4}$alkyloxy;

$R^{23}$ represents $C_{1-4}$alkyl optionally substituted with hydroxy-, $C_{1-4}$alkyloxy- or Het$^{23}$; $R^{23}$ may also represent hydrogen when $R^{16}$ and $R^{17}$ taken together with the carbon atom to which they are attached form a $C_{3-6}$cycloalkyl;

$R^{25}$ and $R^{26}$ each independently represent hydrogen, $C_{1-4}$alkyl, $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

$R^{27}$ and $R^{28}$ each independently represent hydrogen, $C_{1-4}$alkyl, $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

$R^{29}$ and $R^{3o}$ each independently represent hydrogen, aminosulfonyl, aminocarbonyl, mono- or di($C_{1-4}$alkyl)aminocarbonyl-, mono- or di($C_{1-4}$alkyl)aminosulfonyl-, or $C_{1-4}$alkyl- optionally substituted with one or more substituents selected from NR$^{31}$R$^{32}$, $C_{1-4}$alkylsulfonyl, aminocarbonyloxy-, hydroxy-, $C_{1-4}$alkyloxy-, aminocarbonyl- and mono- or di($C_{1-4}$alkyl)aminocarbonyl-, or $C_{1-4}$alkyloxycarbonyl optionally substituted with one or more substituents selected from hydroxy, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-;

$R^{31}$ and $R^{32}$ each independently represent hydrogen, $C_{1-4}$alkyl, $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

$R^{33}$ represents hydrogen or $C_{1-4}$alkyl;

$R^{34}$ represents $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

$R^{35}$ represents hydrogen or $C_{1-4}$alkyl;

$R^{36}$ represents $C_{1-4}$alkylsulfonyl-, aminocarbonyl-, mono- or di($C_{1-4}$alkyl)aminocarbonyl-, $C_{1-4}$alkylcarbonyl-, $C_{1-4}$alkyloxycarbonyl- or $C_{1-4}$alkyl substituted with one or more substituents selected from $C_{1-4}$alkylsulfonyl-, hydroxy- and $C_{1-4}$alkyloxy-;

$R^{37}$ and $R^{38}$ each independently represent hydrogen, $C_{1-4}$alkyl, $C_{1-4}$alkylsulfonyl-, Het$^{12}$ or $C_{1-4}$alkyl substituted with one or more substituents selected from $C_{1-4}$alkylsulfonyl-, hydroxy- and $C_{1-4}$alkyloxy-;

$R^{39}$ and $R^{4o}$ each independently represent aminosulfonyl, aminocarbonyl,
  mono- or di($C_{1-4}$alkyl)aminocarbonyl-, mono- or di($C_{1-4}$alkyl)aminosulfonyl-,
  or
  $C_{1-4}$alkyl- substituted with one or more substituents selected from NR$^{31}$R$^{32}$, $C_{1-4}$alkylsulfonyl, aminocarbonyloxy-, hydroxy-, $C_{1-4}$alkyloxy-, aminocarbonyl- and mono- or di($C_{1-4}$alkyl)aminocarbonyl-,
  or $C_{1-4}$alkyloxycarbonyl optionally substituted with one or more substituents selected from hydroxy, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-;

Het$^{1}$ represents thiazolyl or 2-bora-1,3-dioxolanyl wherein said Het$^{1}$ is optionally substituted with one or where possible two, three, four or more substituents selected from amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-, mono- or di($C_{1-4}$alkyl)amino- or amino-carbonyl-;

Het$^{2}$ represents a heterocycle selected from tetrahydropyranyl, tetrahydrofuranyl, furanyl, 1,1-dioxothiomorpholinyl, piperazininonyl, tetrahydro-1,1-dioxido-2H-thiopyranyl, piperidinonyl, azetidinyl or 2-azetidinonyl wherein said Het$^{2}$ is optionally substituted with one or where possible two or more substituents selected from hydroxy, amino, NR$^{29}$R$^{30}$, aminocarbonyl, mono- or di($C_{1-4}$alkyl)aminocarbonyl, $C_{1-4}$alkylsulfonyl or
  $C_{1-4}$alkyl- optionally substituted with one or more substituents selected from NR$^{27}$ R$^{28}$, $C_{1-4}$alkylsulfonyl, aminocarbonyloxy-, aminocarbonyl- and mono- or di($C_{1-4}$alkyl)aminocarbonyl-, or
  $C_{1-4}$alkyloxy- optionally substituted with $C_{1-4}$alkyloxy-, or
  $C_{1-4}$alkyloxycarbonyl optionally substituted with one or more substituents selected from hydroxy, $C_{1-4}$alkyloxy- and $C_{1-4}$alkylsulfonyl-, or
  $C_{1-4}$alkylcarbonyl optionally substituted with one or more substituents selected from hydroxy-, $C_{1-4}$alkyloxy- and $C_{1-4}$alkylsulfonyl-; or Het$^{2}$ represents a heterocycle selected from morpholinyl, piperazinyl, piperidinyl or pyrrolidinyl wherein said morpholinyl, piperazinyl, piperidinyl or pyrrolidinyl are optionally substituted with one or where possible two or more substituents selected from
  $C_{1-4}$alkyl- optionally substituted with one or more substituents selected from NR$^{27}$R$^{28}$,$C_{1-4}$alkylsulfonyl, aminocarbonyloxy-, aminocarbonyl- and mono- or di($C_{1-4}$alkyl)aminocarbonyl-, or
  $C_{1-4}$alkyloxy- optionally substituted with $C_{1-4}$alkyloxy-, or
  $C_{1-4}$alkyloxycarbonyl optionally substituted with one or more substituents selected from hydroxy, $C_{1-4}$alkyloxy- and $C_{1-4}$alkylsulfonyl-, or
  $C_{1-4}$alkylcarbonyl optionally substituted with one or more substituents selected from hydroxy-, $C_{1-4}$alkyloxy- and $C_{1-4}$alkylsulfonyl-;

Het$^{3}$ represents a heterocycle selected from tetrahydropyranyl, tetrahydrofuranyl, furanyl, 1,1-dioxothiomorpholinyl, piperazininonyl, tetrahydro-1,1-dioxido-2H-thiopyranyl, piperidinonyl, azetidinyl or 2-azetidinonyl wherein said Het$^{3}$ is optionally substituted with one or where possible two or more substituents hydroxy-, amino, $C_{1-4}$ alkyl-, $C_{3-6}$cycloalkyl-, aminosulfonyl-, mono- or di($C_{1-4}$alkyl)aminosulfonyl-, amino-$C_{1-4}$alkyl-, Mono- or di($C_{1-4}$alkyl)amino-$C_{1-4}$alkyl, NR$^{35}$R$^{36}$, $C_{1-4}$alkyl-sulfonyl-$C_{1-4}$alkyl- or $C_{1-4}$alkyloxy- optionally substituted with $C_{1-4}$alkyloxy- or hydroxy; or Het$^{3}$ represents a heterocycle selected from morpholinyl, piperazinyl, piperidinyl or pyrrolidinyl wherein said Het$^{3}$ is optionally substituted with one or where possible two or more substituents selected from NR$^{35}$R$^{36}$, $C_{1-4}$alkyl-sulfonyl -$C_{1-4}$alkyl- or $C_{1-4}$alkyloxy- optionally substituted with $C_{1-4}$alkyloxy- or hydroxy;

Het$^{4}$ represents a heterocycle selected from morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said Het$^{4}$ is substituted with one or where possible two or more substituents selected from $C_{1-4}$alkyl-sulfonyl -$C_{1-4}$alkyl-, $C_{1-4}$alkyloxy- optionally substituted with $C_{1-4}$alkyloxy- or hydroxy;

Het$^{5}$ represents a heterocycle selected from furanyl, piperazinyl, 1,1-dioxothiomorpholinyl, piperazininonyl, piperidinyl, tetrahydro-1,1-dioxido-2H-thiopyranyl, piperidinonyl, morpholinyl or pyrrolidinyl wherein said Het$^{5}$ is optionally substituted with hydroxy, amino, mono- or di($C_{1-4}$alkyl)-amino-, $C_{1-4}$alkyl, Het$^{6}$ and Het$^{1}$ each independently represents a heterocycle selected from piperazinyl, piperidinyl or pyrrolidinyl wherein said heterocycles are optionally substituted with one or more substituents selected from hydroxy-, amino-, hydroxy-$C_{1-4}$alkyl-, $C_{1-4}$alkyloxy-$C_{1-4}$alkyl- and $C_{1-4}$alkyl-;

Het$^{8}$ represents a heterocycle selected from tetrahydropyranyl, tetrahydrofuranyl, 1,1-dioxothiomorpholinyl, piperazininonyl, tetrahydro-1,1-dioxido-2H-thiopyranyl, piperidinonyl, azetidinyl or 2-azetidinonyl wherein said Het$^{8}$ is optionally substituted with aminosulfonyl, aminocarbonyl,
  mono- or di($C_{1-4}$alkyl)aminocarbonyl-, mono- or di($C_{1-4}$alkyl)aminosulfonyl-,
  or
  $C_{1-4}$alkyl- optionally substituted with one or more substituents selected from amino, mono- or di($C_{1-4}$alkyl)amino-, NR$^{33}$R$^{34}$, $C_{1-4}$alkylsulfonyl, aminocarbonyloxy-, hydroxy-, $C_{1-4}$alkyloxy-, aminocarbonyl- and mono- or di($C_{1-4}$alkyl)aminocarbonyl-, or
  $C_{1-4}$alkyloxycarbonyl optionally substituted with one or more substituents selected from hydroxy-, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-; or $Het^8$ represents a heterocycle selected from furanyl, piperidinyl or piperazinyl wherein said $Het^8$ is substituted with aminocarbonyl,
  mono- or di($C_{1-4}$alkyl)aminocarbonyl-, mono- or di($C_{1-4}$alkyl)aminosulfonyl-,
  or
  $C_{1-4}$alkyl- substituted with one or more substituents selected from $NR^{33}R^{34}$, $C_{1-4}$alkylsulfonyl, aminocarbonyloxy-, hydroxy-, $C_{1-4}$alkyloxy-, aminocarbonyl- and mono- or di($C_{1-4}$alkyl)aminocarbonyl-, or $C_{1-4}$alkyloxycarbonyl optionally substituted with one or more substituents selected from hydroxy-, $C_{1-4}$alkyloxy- and $C_{1-4}$alkylsulfonyl-, or $C_{1-4}$alkylcarbonyl optionally substituted with one or more substituents selected from hydroxy-, $C_{1-4}$alkyloxy- and $C_{1-4}$alkylsulfonyl-;

$Het^9$ and $Het^{10}$ each independently represents a heterocycle selected from piperazinyl, piperidinyl or pyrrolidinyl wherein said heterocycles are optionally substituted with one or more substituents selected from hydroxy-, amino, hydroxy-$C_{1-4}$alkyl-, $C_{1-4}$alkyloxy-$C_{1-4}$alkyl- and $C_{1-4}$alkyl-;

$Het^{11}$ represents 2-imidazolidinonyl- or

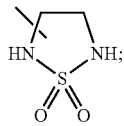

$Het^{12}$ represents a heterocycle selected from morpholinyl, piperazinyl, piperidinyl or pyrrolidinyl wherein said $Het^{12}$ is optionally substituted with one or where possible two or more substituents selected from hydroxy-, amino or $C_{1-4}$alkyl-;

$Het^{13}$ represents a heterocycle selected from furanyl, piperazinyl, 1,1-dioxothiomorpholinyl, piperazininonyl, piperidinyl, tetrahydro-1,1-dioxido-2H-thiopyranyl, piperidinonyl, morpholinyl, piperazinyl or pyrrolidinyl $Het^{16}$ represents a heterocycle selected from piperidinyl or pyrrolidinyl;

$Het^{20}$ represents pyrrolidinyl, 2-pyrrolidinonyl, piperidinyl or hydroxy-pyrrolidinyl or hydroxy-pyrrolidinyl;

$Het^{21}$ represents pyrrolidinyl or hydroxy-pyrrolidinyl;

$Het^{22}$ represents pyrrolidinyl, piperazinyl or piperidinyl;

$Het^{23}$ represents a heterocycle selected from morpholinyl, pyrrolidinyl, piperazinyl or piperidinyl wherein said $Het^{23}$ is optionally substituted with one or where possible two or more substituents selected from $C_{1-4}$alkyl, $C_{3-6}$cycloalkyl, hydroxyl
  -$C_{1-4}$alkyl-, $C_{1-4}$alkyloxy$C_{1-4}$alkyl or polyhydroxy-$C_{1-4}$ alkyl-;

$Ar^4$, $Ar^5$ or $Ar^6$ each independently represent phenyl optionally substituted with nitro, cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl.

24. A compound according to any one of claims 1 to 20, 4-9, 7-17, 22 and 23 wherein $R^{16}$ and $R^{17}$ are other than hydrogen.

25. A pharmaceutical composition comprising a pharmaceutically acceptable carrier and, as active ingredient, an effective kinase inhibitory amount of a compound as described in claim 24.

* * * * *